United States Patent
Richardson et al.

(10) Patent No.: US 12,233,162 B2
(45) Date of Patent: Feb. 25, 2025

(54) METHOD FOR PREPARING LIPOSOMES

(71) Applicant: The University of Greenwich, Greenwich (GB)

(72) Inventors: Simon Richardson, Greenwhich (GB); Benedita Feron, Greenwich (GB)

(73) Assignee: The University of Greenwich (GB)

( * ) Notice: Subject to any disclaimer, the term of this patent is extended or adjusted under 35 U.S.C. 154(b) by 996 days.

(21) Appl. No.: 17/266,904

(22) PCT Filed: Aug. 9, 2019

(86) PCT No.: PCT/GB2019/052239
§ 371 (c)(1),
(2) Date: Feb. 8, 2021

(87) PCT Pub. No.: WO2020/030923
PCT Pub. Date: Feb. 13, 2020

(65) Prior Publication Data
US 2021/0338584 A1 Nov. 4, 2021

(30) Foreign Application Priority Data

Aug. 9, 2018 (GB) ..................... 1812992

(51) Int. Cl.
| | | |
|---|---|---|
| *A61K 9/127* | (2006.01) | |
| *A61K 9/1271* | (2025.01) | |
| *A61K 9/1277* | (2025.01) | |
| *A61K 31/7105* | (2006.01) | |
| *A61K 38/46* | (2006.01) | |
| *A61P 31/14* | (2006.01) | |
| *C12N 9/12* | (2006.01) | |
| *C12N 15/113* | (2010.01) | |

(52) U.S. Cl.
CPC .......... *A61K 9/1277* (2013.01); *A61K 9/1271* (2013.01); *A61K 31/7105* (2013.01); *A61K 38/465* (2013.01); *A61P 31/14* (2018.01); *C12N 9/12* (2013.01); *C12N 15/113* (2013.01); *C07K 2319/00* (2013.01); *C12N 2310/14* (2013.01); *C12N 2320/32* (2013.01)

(58) Field of Classification Search
None
See application file for complete search history.

(56) References Cited

U.S. PATENT DOCUMENTS

2015/0275229 A1    10/2015    Meadow, Jr.

FOREIGN PATENT DOCUMENTS

| WO | 2012096926 A2 | 7/2012 | |
|---|---|---|---|
| WO | 2013138427 | 9/2013 | |
| WO | 2014203008 | 12/2014 | |
| WO | WO-2014203008 A1 * | 12/2014 | ............ A61P 31/12 |
| WO | 2015002956 | 1/2015 | |
| WO | 2016187717 | 12/2016 | |
| WO | 2018015535 | 1/2018 | |

OTHER PUBLICATIONS

Movahedi et al. "Stimuli-responsive liposomes for the delivery of nucleic acid therapeutics." Nanomedicine: Nanotechnology, Biology and Medicine. vol. 11, Issue 6 (2015): 1575-1584. doi: 10.1016/j.nano.2015.03.006 (Year: 2015).*

Abrami et al., "Hijacking Multivesicular Bodies ENables Long-Term and Exosome-5 Mediated Long-Distance Action of Anthrax Toxin", Cell Reports, Nov. 1, 2013, vol. 5, No. 4.

Dyer et al., "Disarmed anthrax toxin delivers antisense oligonucleotides and siRNA with high efgfgiciency and low toxicity", Journal of Controlled Release, vol. 220, Nov. 9, 2015, pp. 316-328.

Rabideau et al., "Delivery of Non-Native Cargo into Mammalian Cells Using Anthrax Lethal Toxin", ACS Chemical Biology, vol. 11, No. 6, May 2, 2016, pp. 1490-1501.

Shorter et al., "The potential of toxin-based drug delivery systems for enhanced nucleic acid therapeutic delivery", Expert Opinion on Drug Delivery, vol. 14, No. 5, Sep. 7, 2016, pp. 685-696.

* cited by examiner

*Primary Examiner* — Allison M Fox
(74) *Attorney, Agent, or Firm* — FisherBroyles, LLP; Adam K. Whiting; Adelaide K. Leitzel

(57) ABSTRACT

The invention relates to liposomes, methods of producing liposomes, and methods of loading cell-derived liposomes with cargo molecules. The invention extends to such liposomes per se, and to the use of these liposomes as cellular delivery systems for the delivery of biologically and therapeutically active payload molecules, such as small molecules, RNAi molecules (e.g. siRNA), bioactive proteins, genome editing tools (e.g. Cas9) and drugs into cells for treating a range of disorders. The liposomes may also be used in a range of diagnostic and theranostic applications. The invention extends to pharmaceutical compositions comprising such liposomes, including populations of extracellular vesicles (EV), exosomes and to fusion proteins.

16 Claims, 12 Drawing Sheets

Specification includes a Sequence Listing.

Panel A

Cell Mask (Cy5)-labeled exosomes | Texas Red

Panel B

Cell Mask (Cy5)-labeled exosomes | Texas Red

METHOD FOR PREPARING LIPOSOMES

CROSS-REFERENCE

This application is a 371 National Stage filing and claims the benefit under 35 U.S.C. § 120 to International Application No. PCT/GB2019/052239, filed Aug. 9, 2019, which claims priority to Great Britain Application No. 1812992.4, filed Aug. 9, 2018, each of which is incorporated herein by reference in its entirety.

The present invention relates to liposomes, and particularly, although not exclusively, to methods of producing liposomes, and methods of loading cell-derived liposomes with cargo molecules. The invention extends to such liposomes per se, and to the use of these liposomes as cellular delivery systems for the stealth delivery of biologically and therapeutically active payload molecules, such as small molecules, RNAi molecules (e.g. siRNA), antisense oligonucleotides (ASOs), bioactive proteins, genome editing tools (e.g. a nuclease, such as Cas9) and drugs into cells for treating a range of disorders. The liposomes may also be used in a range of diagnostic and theranostic applications. The invention extends to pharmaceutical compositions comprising such liposomes, including populations of extracellular vesicles (EV) and to fusion proteins.

Synthetic, nanoscale, advanced drug delivery systems for the targeted, subcellular delivery and controlled release of both small molecules and high molecular weight therapeutics have been documented [1]. They non-exhaustively incorporate nano-particulate systems, liposomes, hydrogels, emulsions, micelles and soluble polymer based drug delivery technology [1]. Recently, the possibility of using biological systems, recombining discreet protein domains that have evolved to perform specific tasks (i.e. facilitating the delivery of therapeutics), has received attention [2]. These efforts include the use of protein toxin-derived material to navigate the intracellular endomembrane system in order to achieve the targeted delivery of large, membrane impervious molecules, such as antisense oligonucleotides (ASO) [2]. This is useful as without a means of crossing intracellular compartmental barriers, the bioavailability of these reagents (ASOs) is limited [2].

Proteins such as anthrax toxin (Atx) have evolved to subvert the endomembrane system to access the cytosol. This is done via a back-fusion event between intraluminal vesicles (ILVs), within a multivesicular endosome (MVE)/multivesicular body (MVB), and the limiting membrane of the MVE/MVB during an apoptosis-linked gene 2-interacting protein X (ALIX) dependent process [3&4].

The PA oligomer (pore) component of Atx is reported in the literature to be a cation selective pore [6], responsible for the movement of oedema factor (EF) and lethal factor (LF) from the lumen of the MVE/MVB to the lumen of the ILV. Further, both EF and LF need to undergo a molten-globular transition (i.e. unfold) in order to move through the $PA63_n$ oligomer [7]. It has further been published that CAS9 should not transit through the PA pore [8]. Additionally, there is only circumstantial, indirect evidence that pore translocation has occurred during the delivery of siRNA or ASOs [2], as there has always been the possibility (especially given the high concentrations of PA83 protein used), that translocation was occurring either across the limiting membrane of the MVE/MVB [3] or that the MVE/MVB limiting membrane was rupturing.

When the catalytic subunits of LF (i.e. domains II-IV) were removed from LF, the resulting non-toxic LF truncation (LFn) has been shown to help facilitate the movement of selective cargoes fused to it over the PA pore into the cytosol [2]. The use of PA83 and LFn-GAL4 to deliver ASOs or PA83::LFn-PKR to deliver siRNA into the cytosol of cells has been previously reported [2].

The PA83:LFn-GAL4 or PA83::LFn-PKR mediated nucleocytosolic delivery of nucleic acids (and proteins) falls short of ideal for several reasons. The first is that using this system systemically, i.e. after i.v. administration, exposes the cargo and the drug delivery system to the bodies' defences. As components of this delivery technology are known to be immunogenic (i.e. PA83 and LFn) [11], there is likely to be a limit to the plasma residence time of these constructs if repeated doses are required. Secondly, there is also the possibility of the destruction of the protein delivery system or its cargo whilst in transit to the target cells after systemic administration. In addition, there exists little scope for the targeted delivery to specific populations of cells, as the expression of the receptors responsible for internalisation of PA83 has been shown to be nearly ubiquitous [12]. Finally, the possibility of limited PK-PD, driven by the charge of polyanions such as ASOs i.e. their rapid removal from the plasma pool by the cells of the reticuloendothelial system, should also be considered [13].

Given that wild type LF has been documented within both ILVs and liposomes (e.g. exosomes), and it is known that ILVs can be secreted from cells as liposomes after the release of ER stored calcium [5], it has been reasoned by the inventors that recombinant LF could also be trapped or loaded into liposomes. Further, the use of an ionophore (e.g. ionomycin) results in the release of ER calcium on demand, triggering the exocytosis of ILVs, as liposomes. Consequently, ionomycin was used to temporally capture ILVs containing cargo, from cells that were previously treated with the Atx derived delivery system. This then allowed for the isolation of cargo loaded liposomes secreted into the cell culture media.

The present invention is seeking to address one or more problems inherent in the prior art.

The inventors have developed a novel methodology for loading intraluminal vesicles (or liposomes), which can then be collected as exosomes, containing membrane impervious (therapeutic) cargo material. This strategy imparts "stealth" qualities upon the cargo entrapped within the lumen of the vesicle, shielding it from the immune system and protecting it from destruction via enzymes associated with serum or other bodily fluids. The liposomes described herein can shield intraluminal content from enzymatic destruction and the immune response, and are often referred to as a naturally occurring, paracrine transport system that protects antigenic or enzymatically labile material in transit. It also has the capacity for cell or tissue targeting.

Hence, in a first aspect of the invention, there is provided a method of preparing a liposome, the method comprising contacting at least one cell with: (i) a pore-forming protein, or a pore-forming domain or a variant or fragment thereof; and (ii) a shuttle protein, optionally attached to a bioactive payload molecule, wherein the pore-forming protein, or the pore-forming domain or the variant or fragment thereof creates a pore through a phospholipid bilayer of the at least one cell, and the shuttle protein interacts with the pore-forming protein, or the pore-forming domain or the variant or fragment thereof, and is internalised into the cell to thereby produce a liposome, optionally loaded with a bioactive payload molecule.

Advantageously, the inventors have demonstrated that the method of the first aspect enables the efficient production of a liposome (also referred to herein as an "exosome"), which comprises an inner lumen surrounded or encapsulated by an outer phospholipid bilayer. FIG. 7 shows an embodiment of the method of the invention. As shown in FIG. 1, the inventors have discovered that a labelled shuttle protein, preferably a fluorophore covalently conjugated to the shuttle protein, most preferably Texas Red-labelled LFn-PKR, can, in the presence of the pore-forming protein, PA83, associate with intraluminal vesicles within a CD63 positive, membrane-delimited structure. Furthermore, these intraluminal vesicles can be isolated, as shown in FIG. 2 and FIG. 5. In some embodiments, the liposomes can be successfully loaded with a bioactive payload or cargo molecule and can then be taken up by target cells (e.g. the cells of a patient suffering from a certain condition). The bioactive payload or cargo molecules can produce efficacious biological or therapeutic results (e.g. see FIG. 6). Hence, the inventors have envisaged a therapeutic application for the liposomes. The inventors have also shown that a bioactive payload molecule can be coupled to the shuttle protein, and FIG. 3 provides clear evidence that the isolated liposomes contain the bioactive payload molecules labelled with the fluorophore, Texas Red. In FIG. 3, the bioactive payload molecule is a nuclease protein, Cas9, and, in FIG. 4, the payload molecule is a small molecule, such as Texas Red.

The methods of the invention may be carried out in vitro, in vivo, or ex vivo. In a preferred embodiment, the method further comprises isolating the liposome from the cell. The shuttle protein may not be attached to a bioactive payload molecule. However, in a preferred embodiment, the shuttle protein is attached to a bioactive payload molecule, either covalently or non-covalently.

The inventors have also demonstrated that the pore-forming protein and shuttle protein can be used to successfully load the liposome with pharmacologically active siRNA, as shown in FIG. 6. The method of the invention can be used to load and deliver biologically active cargo compounds into liposomes, which can be isolated and used to transfer the cargo from one population of cells to another. In view of these data, therefore, it is clear that the liposomes produced by the method of the first aspect can be used, therapeutically, to treat a wide range of disorders, depending on which bioactive payload molecule is being carried.

According to a second aspect, there is provided a liposome obtained, or obtainable by, the method of the first aspect.

According to a third second aspect, there is provided a liposome comprising a phospholipid bilayer surrounding a lumen, a pore-forming protein, or a pore-forming domain or a variant or a fragment thereof, and a shuttle protein.

It is also envisaged that the liposome of the invention may be used in therapy, including treating, preventing, or ameliorating a condition, or in diagnostics.

Therefore, according to a fourth aspect, there is provided the liposome according to either the second or third aspect, for use in therapy or diagnosis.

According to a fifth aspect, there is provided the liposome according to either the second or third aspect, for use in treating, preventing, or ameliorating a disease.

According to a sixth aspect, there is provided a method of treating, preventing or ameliorating a disease in a subject, the method comprising administering, to a subject in need of such treatment, a therapeutically effective amount of the liposome according to either the second or third aspect.

Specifically, the inventors envisage that the liposome may be useful in the treatment of FMO5-regulated obesity or male pattern baldness. Thus, in one preferred embodiment, the disease to be treated is obesity, more preferably FMO5-regulated obesity. In another preferred embodiment, the disease to be treated is prostaglandin-D2-regulated. The prostaglandin-D2-regulated disease may be selected from a group consisting of: androgenetic alopecia (AGA); acne; rosacea; and prostate cancer.

In another preferred embodiment, the liposome may be useful in treatment as a prophylactic. The liposomes may be used for, but not limited to, the treatment of: Zika fever (or Zika virus disease), Ebola virus disease, Acquired immunodeficiency syndrome (human immunodeficiency virus), Stat3-responsive cancer, P53-deficient cancer, virally-mediated cervical cancer (i.e. human papilloma virus), familial hypercholesterolemia, Duchene muscular dystrophy, spinal muscular atrophy, Crohn's disease, and various Inflammatory diseases especially those of the bowel implicated in the overexpression of intracellular adhesion molecule-1 (ICAM-1).

According to a seventh aspect, there is provided a method of diagnosing a disease in a subject, the method comprises obtaining a biological sample from a test subject, and using the cells in the sample to produce liposomes using the method of the first aspect loaded with a diagnostic compound.

In one embodiment, this would comprise loading a theranostic compound into the liposome that could report the presence or absence of a disease though the interaction of the liposomal cargo with a disease marker with the diseased cell.

In another embodiment, and as demonstrated in example 8, liposomes which are not derived from patient cells (e.g. cultured mesenchymal stem cell-derived liposomes) are loaded with a theranostic compound. In yet another embodiment, liposomes derived not from patients but from cell lines are used as therapeutics by loading them with another cargo. In one embodiment, a disease may be treated non-patient derived liposomes. In one embodiment, the non-patient derived liposomes are derived from non-patient cells. In another embodiment the non-patient derived liposomes are derived from stem cells.

The resulting liposomes may then be administered to a patient without adverse immunological effects, i.e. as a "stealth" therapy.

According to an eighth aspect, there is provided a kit comprising the liposome according to either the second or third aspect, and instructions for use.

The liposome may comprise a vesicle, which may be an extracellular vesicle (EV) or an intracellular vesicle, or an intraluminal vesicle (ILV). Most preferably, the liposome comprises an exosome. It will be appreciated by the skilled person that, although the lipid structures referred to herein are largely extracellular, the invention should also be considered to cover substantially intracellular lipid bilayer structures, such as lysosomes, endosomes and other intracellular lipid bilayer structures, both eukaryotic and prokaryotic, and the vesicles therein. It will be further appreciated that the invention also covers artificial lipid bilayer structures, such as artificial vesicles, artificial liposomes and other artificial lipid bilayer structures.

In one embodiment, the liposome has an average diameter of between 10 nm and 500 nm. The dimensions of the liposome can be measured, for example, using small-angle neutron scattering [2]. In a preferred embodiment, the liposome has an average diameter of between 20 nm and 400 nm. In a more preferred embodiment, the liposome has an average diameter of between 30 nm and 300 nm. In a still more preferred embodiment, the liposome has an average diameter of between 40 nm and 200 nm. In a still more preferred embodiment, the liposome has an average diameter of between 50 nm and 150 nm. In a most preferred embodiment, the liposome has an average diameter of between 60 nm and 120 nm.

In a preferred embodiment, the liposome comprises a phospholipid bilayer with a pore-forming protein, or a pore-forming domain or a variant or fragment thereof within the phospholipid bilayer. The pore-forming protein, or a pore-forming domain or a variant or fragment thereof may fully extend across the width of the phospholipid bilayer, or it may only extend partially across the width of the phospholipid bilayer. The pore-forming protein, or a pore-forming domain or a variant or fragment thereof may extend into the lumen of the cell and/or it may extend into the extracellular space of the cell. The pore-forming protein, or a pore-forming domain or a variant or fragment thereof may only extend across the phospholipid bilayer and does not extend into the lumen of the cell and/or the extracellular space of the cell.

Preferably, the cell used in the method of the first aspect comprises a biological cell. Preferably, the cell comprises a mammalian cell, which is most preferably a human cell. Most preferably, the cell comprises a cell obtained from a subject being treated. For example, the cell may be an unhealthy cell obtained from the subject, e.g. collected from a biopsy. Alternatively, the cell comprises a cell obtained from a stem cell line. The stem cell line may be a mesenchymal cell line.

In one non-limiting example, healthy cells may be collected from the target tissue and expanded in culture prior to being used for the production of liposome (e.g. an exosome) that is loaded with a therapeutic compound appropriate to treating the clinical condition in question. This will minimise the possibility of the liposome being recognised as "non-self" by the body. There is also the possibility of treating the liposome to remove any residual antigenic material that may be left from the process of loading it with the therapeutic. In one embodiment, the collected cells may comprise healthy cells. In an alternative non-limiting example, the collected cells may not comprise healthy cells.

Preferably, the pore-forming protein, or the pore-forming domain or the variant or fragment thereof comprises, or is derived from, a non-toxic protein. In one embodiment, the pore-forming protein, or the pore-forming domain or the variant or fragment thereof is Ricin.

In a preferred embodiment the pore-forming protein, or the pore-forming domain or the variant or fragment thereof is derived from *B. anthracis*. In a preferred embodiment, the pore-forming protein is *B. anthracis* virulence factor Protective Antigen (PA). In one embodiment, the pore-forming protein is *B. anthracis* PA83. In one embodiment, the *B. anthracis* PA83 has an amino acid sequence, which is provided herein as SEQ ID No: 1, as follows:

[SEQ ID No: 1]
MRGSHHHHHHGSEVKQENRLLNESESSSQGLLGYYFSDLNFQAPMVVTS

STTGDLSIPSSELENIPSENQYFQSAIWSGFIKVKKSDEYTFATSADNH

VTMWVDDQEVINKASNSNKIRLEKGRLYQIKIQYQRENPTEKGLDFKLY

WTDSQNKKEVISSDNLQLPELKQKSSNSRKKRSTSAGPTVPDRDNDGIP

DSLEVEGYTVDVKNKRTFLSPWISNIHEKKGLTKYKSSPEKWSTASDPY

SDFEKVTGRIDKNVSPEARHPLVAAYPIVHVDMENIILSKNEDQSTQNT

DSQTRTISKNTSTSRTHTSEVHGNAEVHASFEDIGGSVSAGFSNSNSST

VAIDHSLSLAGERTWAETMGLNTADTARLNANIRYVNTGTAPIYNVLPI

TSLVLGKNQTLATIKAKENQLSQILAPNNYYPSKNLAPIALNAQDDFSS

TPITMNYNQFLELEKTKQLRLDTDQVYGNIATYNFENGRVRVDTGSNWS

EVLPQIQETTARIIFNGKDLNLVERRIAAVNPSDPLETTKPDMILKEAL

KIAFGFNEPNGNLQYQGKDITEFDFNFDQQTSQNIKNQLAELNATNIYT

VLDKIKLNAKMNILIRDKRFHYDRNNIAVGADESVVKEAHREVINSSTE

GLLLNIDKDIRKILSGYIVEIEDTEGLKEVINDRYDMLNISSLRQDGKT

FIDFKKYNDKLPLYISNPNYKVNVYAVTKENTIINPSENGDTSTNGIKK

ILIFSKKGYEIG

Thus, preferably the pore-forming protein, or the pore-forming domain or the variant or fragment thereof, comprises or consists of an amino acid sequence substantially as set out in SEQ ID No: 1, or a variant or fragment thereof.

In one preferred embodiment, the *B. anthracis* PA83 comprises a PA83 variant (referred to herein as "MRSG-6His-PA83"), which has an amino acid sequence, which is provided herein as SEQ ID No: 2, as follows:

[SEQ ID No: 2]
MRGSHHHHHHGSEVKQENRLLNESESSSQGLLGYYFSDLNFQAPMVVTS

STTGDLSIPSSELENIPSENQYFQSAIWSGFIKVKKSDEYTFATSADNH

VTMWVDDQEVINKASNSNKIRLEKGRLYQIKIQYQRENPTEKGLDFKLY

WTDSQNKKEVISSDNLQLPELKQKSSNSRKKRSTSAGPTVPDRDNDGIP

DSLEVEGYTVDVKNKRTFLSPWISNIHEKKGLTKYKSSPEKWSTASDPY

SDFEKVTGRIDKNVSPEARHPLVAAYPIVHVDMENIILSKNEDQSTQNT

DSQTRTISKNTSTSRTHTSEVHGNAEVHASFEDIGGSVSAGFSNSNSST

VAIDHSLSLAGERTWAETMGLNTADTARLNANIRYVNTGTAPIYNVLPT

TSLVLGKNQTLATIKAKENQLSQILAPNNYYPSKNLAPIALNAQDDFSS

TPITMNYNQFLELEKTKQLRLDTDQVYGNIATYNFENGRVRVDTGSNWS

EVLPQIQETTARIIFNGKDLNLVERRIAAVNPSDPLETTKPDMTLKEAL

KIAFGENEPNGNLQYQGKDITEEDFNEDQQTSQNIKNQLAELNATNIYT

VLDKIKLNAKMNILIRDKRFHYDRNNIAVGADESVVKEAHREVINSSTE

GLLLNIDKDIRKILSGYIVEIEDTEGLKEVINDRYDMLNISSLRQDGKT

FIDFKKYNDKLPLYISNPNYKVNVYAVTKENTIINPSENGDTSTNGIKK

ILIFSKKGYEIG

Thus, preferably the pore-forming protein, or the pore-forming domain or the variant or fragment thereof, comprises or consists of an amino acid sequence substantially as set out in SEQ ID No: 2, or a variant or fragment thereof.

It will be appreciated by the skilled person that the PA83 variant according to SEQ ID No: 2 comprises an N-terminal tagged variant whereby the tag comprises MRSG-6H and has an amino acid sequence, which is provided herein as SEQ ID No: 3, as follows:

[SEQ ID No: 3]
MRGSHHHHHH

An alternative protein tag comprising 6His is provided herein as SEQ ID No: 4, as follows:

[SEQ ID No: 4]
HHHHHH

It will be appreciated by the skilled person that the MRSG-6His and 6-His tags, as set out in SEQ ID No: 3 and SEQ ID No: 4, may be added to the N-terminus or C-terminus of any protein described herein, and it will be understood that such a disclosure protects both the tagged and untagged protein variants.

It will be appreciated that the pore-forming protein may comprise a single performing domain or subunit, which may form into an oligomer, such as B. anthracis PA63. Therefore, in another preferred embodiment, the pore-forming protein is B. anthracis PA63. In one embodiment, the B. anthracis PA63 has an amino acid sequence, which is provided herein as SEQ ID No: 5, as follows:

[SEQ ID No: 5]
STSAGPTVPDRDNDGIPDSLEVEGYTVDVKNKRTFLSPWISNIHEKKGLTK
YKSSPEKWSTASDPYSDFEKVTGRIDKNVSPEARHPLVAAYPIVHVDMENI
ILSKNEDQSTQNTDSQTRTISKNTSTSRTHTSEVHGNAEVHASFFDIGGSV
SAGFSNSNSSTVAIDHSLSLAGERTWAETMGLNTADTARLNANIRYVNTGT
APIYNVLPTTSLVLGKNQTLATIKAKENQLSQILAPNNYYPSKNLAPIALN
AQDDFSSTPITMNYNQFLELEKTKQLRLDTDQVYGNIATYNFENGRVRVDT
GSNWSEVLPQIQETTARIIFNGKDLNLVERRIAAVNPSDPLETTKPDMTLK
EALKIAFGFNEPNGNLQYQGKDITEFDFNEDQQTSQNIKNQLAELNATNIY
TVLDKIKLNAKMNILIRDKRFHYDRNNIAVGADESVVKEAHREVINSSTEG
LLLNIDKDIRKILSGYIVEIEDTEGLKEVINDRYDMLNISSLRQDGKTFID
EKKYNDKLPLYISNPNYKVNVYAVTKENTIINPSENGDTSTNGIKKILIFS
KKGYEIG

Thus, preferably the pore-forming protein, or the pore-forming domain or the variant or fragment thereof, comprises or consists of an amino acid sequence substantially as set out in SEQ ID No: 5, or a variant or fragment thereof.

It will also be appreciated that in some cases, the pore-forming protein, or the pore-forming domain or the variant or fragment thereof may comprise a fragment of the pore-forming protein. For example, the pore forming protein may be truncated or digested to leave only a pore-forming fragment, e.g. by an enzyme. Therefore, in one embodiment, the pore-forming protein is a fragment is of B. anthracis PA83 whereby the extra-cellular domain has been enzymatically removed. In another embodiment, the pore-forming protein is a fragment of 15 B. anthracis PA63, whereby the extra-cellular domain has been enzymatically removed. It will be appreciated by the skilled person that both of these protein fragments will have an amino acid sequence, which is provided herein as SEQ ID No: 6, as follows:

[SEQ ID No: 6]
VHVDMENIILSKNEDQSTQNTDSQTRTISKNTSTSRTHTSEVHGNAEVHAS
FFDIGGSVSAGFSNSNSSTVAIDHSLSLAGERTWAETMGLNTADTARLNAN
IRYVNT

Thus, preferably the pore-forming protein, or the pore-forming domain or the variant or fragment thereof, comprises or consists of an amino acid sequence substantially as set out in SEQ ID No: 6, or a variant or fragment thereof.

It will be further appreciated that, in some cases, the pore-forming protein, or the pore-forming domain or the variant or fragment thereof may comprise a mutant or a variant of the pore-forming protein, for example, where one or more residues of the native protein have been modified.

Therefore, in a further embodiment, the pore-forming protein is a B. anthracis PA83 D512K mutant and has an amino acid sequence, which is provided herein as SEQ ID No: 7, as follows:

[SEQ ID No: 7]
MRGSHHHHHHGSEVKQENRLLNESESSSQGLLGYYFSDLNFQAPMVVTSST
TGDLSIPSSELENIPSENQYFQSAIWSGFIKVKKSDEYTFATSADNHVTMW
VDDQEVINKASNSNKIRLEKGRLYQIKIQYQRENPTEKGLDFKLYWTDSQN
KKEVISSDNLQLPELKQKSSNSRKKRSTSAGPTVPDRDNDGIPDSLEVEGY
TVDVKNKRTFLSPWISNIHEKKGLTKYKSSPEKWSTASDPYSDFEKVTGRI
DKNVSPEARHPLVAAYPIVHVDMENIILSKNEDQSTQNTDSQTRTISKNTS
TSRTHTSEVHGNAEVHASFEDIGGSVSAGFSNSNSSTVAIDHSLSLAGERT
WAETMGLNTADTARLNANIRYVNTGTAPIYNVLPTTSLVLGKNQTLATIKA
KENQLSQILAPNNYYPSKNLAPIALNAQDDFSSTPITMNYNQFLELEKTKQ
LRLDTDQVYGNIATYNFENGRVRVDTGSNWSEVLPQIQETTARIIFNGKDL
NLVERRIAAVNPSKPLETTKPDMTLKEALKIAFGFNEPNGNLQYQGKDITE
FDFNFDQQTSQNIKNQLAELNATNIYTVLDKIKLNAKMNILIRDKRFHYDR
NNIAVGADESVVKEAHREVINSSTEGLLLNIDKDIRKILSGYIVEIEDTEG
LKEVINDRYDMLNISSLRQDGKTFIDFKKYNDKLPLYISNPNYKVNVYAVT
KENTIINPSENGDTSTNGIKKILIFSKKGYEIG

Thus, preferably the pore-forming protein, or the pore-forming domain or the variant or fragment thereof, comprises or consists of an amino acid sequence substantially as set out in SEQ ID No: 7, or a variant or fragment thereof.

In a yet further embodiment, the pore-forming protein is a B. anthracis PA83 K245G; R252N [16] mutant and has an amino acid sequence, which is provided herein as SEQ ID No: 8, as follows:

[SEQ ID No: 8]
MRGSHHHHHHGSEVKQENRLLNESESSSQGLLGYYFSDLNFQAPMVVTSST
TGDLSIPSSELENIPSENQYFQSAIWSGFIKVKKSDEYTFATSADNHVTMW
VDDQEVINKASNSNKIRLEKGRLYQIKIQYQRENPTEKGLDFKLYWTDSQN
KKEVISSDNLQLPELKQKSSNSRKKRSTSAGPTVPDRDNDGIPDSLEVEGY
TVDVKNKRTFLSPWISNIHEKKGLTKYKSSPEKWSTASDPYSDFEKVTGRI
DGNVSPEANHPLVAAYPIVHVDMENIILSKNEDQSTQNTDSQTRTISKNTS
TSRTHTSEVHGNAEVHASFEDIGGSVSAGFSNSNSSTVAIDHSLSLAGERT
WAETMGLNTADTARLNANIRYVNTGTAPIYNVLPTTSLVLGKNQTLATIKA
KENQLSQILAPNNYYPSKNLAPIALNAQDDFSSTPITMNYNQFLELEKTKQ
LRLDTDQVYGNIATYNFENGRVRVDTGSNWSEVLPQIQETTARIIFNGKDL

NLVERRIAAVNPSDPLETTKPDMTLKEALKIAFGFNEPNGNLQYQGKDITE

FDFNFDQQTSQNIKNQLAELNATNIYTVLDKIKLNAKMNILIRDKRFHYDR

NNIAVGADESVVKEAHREVINSSTEGLLLNIDKDIRKILSGYIVEIEDTEG

LKEVINDRYDMLNISSLRQDGKTFIDFKKYNDKLPLYISNPNYKVNVYAVT

KENTIINPSENGDTSTNGIKKILIFSKKGYEIG

Thus, preferably the pore-forming protein, or the pore-forming domain or the variant or fragment thereof, comprises or consists of an amino acid sequence substantially as set out in SEQ ID No: 8, or a variant or fragment thereof.

In a still further embodiment, the pore-forming protein is a *B. anthracis* PA83 K245N; R252S [16] mutant and has an amino acid sequence, which is provided herein as SEQ ID No: 9, as follows:

[SEQ ID No: 9]
MRGSHHHHHHGSEVKQENRLLNESESSSQGLLGYYFSDLNFQAPMVVTSST

TGDLSIPSSELENIPSENQYFQSAIWSGFIKVKKSDEYTFATSADNHVTMW

VDDQEVINKASNSNKIRLEKGRLYQIKIQYQRENPTEKGLDFKLYWTDSQN

KKEVISSDNLQLPELKQKSSNSRKKRSTSAGPTVPDRDNDGIPDSLEVEGY

TVDVKNKRTFLSPWISNIHEKKGLTKYKSSPEKWSTASDPYSDFEKVTGRI

DNNVSPEASHPLVAAYPIVHVDMENIILSKNEDQSTQNTDSQTRTISKNTS

TSRTHTSEVHGNAEVHASFFDIGGSVSAGFSNSNSSTVAIDHSLSLAGERT

WAETMGLNTADTARLNANIRYVNTGTAPIYNVLPTTSLVLGKNQTLATIKA

KENQLSQILAPNNYYPSKNLAPIALNAQDDFSSTPITMNYNQFLELEKTKQ

LRLDTDQVYGNIATYNFENGRVRVDTGSNWSEVLPQIQETTARIIFNGKDL

NLVERRIAAVNPSDPLETTKPDMTLKEALKIAFGFNEPNGNLQYQGKDITE

FDFNFDQQTSQNIKNQLAELNATNIYTVLDKIKLNAKMNILIRDKRFHYDR

NNIAVGADESVVKEAHREVINSSTEGLLLNIDKDIRKILSGYIVEIEDTEG

LKEVINDRYDMLNISSLRQDGKTFIDFKKYNDKLPLYISNPNYKVNVYAVT

KENTIINPSENGDTSTNGIKKILIFSKKGYEIG.

Thus, preferably the pore-forming protein, or the pore-forming domain or the variant or fragment thereof, comprises or consists of an amino acid sequence substantially as set out in SEQ ID No: 9, or a variant or fragment thereof.

In another embodiment, the pore-forming protein comprises a *B. anthracis* PA83-HL hybrid molecule incorporating the trans-membrane domain of haemolysin [17] replacing the PA63 trans-membrane domain having an amino acid sequence, which is provided herein as SEQ ID No: 10, as follows:

[SEQ ID No: 10]
GSEVKQENRLLNESESSSQGLLGYYFSDLNFQAPMVVTSSTTGDLSIPSSE

LENIPSENQYFQSAIWSGFIKVKKSDEYTFATSADNHVTMWVDDQEVINKA

SNSNKIRLEKGRLYQIKIQYQRENPTEKGLDFKLYWTDSQNKKEVISSDNL

QLPELKQKSSNSRKKRSTSAGPTVPDRDNDGIPDSLEVEGYTVDVKNKRTF

LSPWISNIHEKKGLTKYKSSPEKWSTASDPYSDFEKVTGRIDKNVSPEARH

PLVAAYPIVHVDMENIILSKNEDQSTQNTDSQTRTISKNTSKEYMSTLTYG

ENGNVTGDDTGKIGGLIGANVSIGHTLKYAIDHSLSLAGERTWAETMGLNT

ADTARLNANIRYVNTGTAPIYNVLPTTSLVLGKNQTLATIKAKENQLSQIL

APNNYYPSKNLAPIALNAQDDFSSTPITMNYNQFLELEKTKQLRLDTDQVY

GNIATYNFENGRVRVDTGSNWSEVLPQIQETTARIIFNGKDLNLVERRIAA

VNPSDPLETTKPDMTLKEALKIAFGFNEPNGNLQYQGKDITEFDFNFDQQT

SQNIKNQLAELNATNIYTVLDKIKLNAKMNILIRDKRFHYDRNNIAVGADE

SVVKEAHREVINSSTEGLLLNIDKDIRKILSGYIVEIEDTEGLKEVINDRY

DMLNISSLRQDGKTFIDFKKYNDKLPLYISNPNYKVNVYAVTKENTIINPS

ENGDTSTNGIKKILIFSKKGYEIG

Thus, preferably the pore-forming protein, or the pore-forming domain or the variant or fragment thereof, comprises or consists of an amino acid sequence substantially as set out in SEQ ID No: 10, or a variant or fragment thereof.

It will be appreciated by the skilled person that the above embodiments represent examples of pore forming proteins and are by no means limiting or exclusive. It will be further appreciated that any other fragments, variants, or mutants of the pore forming protein will also fall within the scope of this invention.

Other examples of preferred pore forming proteins include PA83 or PA63 components of Atx, mutants of PA83 or PA63, such as the octamer forming mutants described [16], or PA hybrids such as the PA-alpha haemolysin hybrid described or non-Atx pore forming proteins modified to mediate translocation over a lipid bilayer, such as recombinant streptolysin O (SLO) or alpha-haemolysin.

The term "shuttle protein" can refer to any protein or peptide which is configured to facilitate transport through the pore of the preforming protein. In a preferred embodiment, the shuttle protein is configured to facilitate transport of a bioactive payload molecule through the pore. Hence, the shuttle protein is preferably a vehicle that can traverse the limiting membrane of an endosome through a pore, taking a payload or cargo with it. The payload may be covalently or non-covalently associated with the shuttle protein. FIG. 7 illustrates the interaction between the shuttle protein, optionally carrying the payload, and the pore forming protein.

Preferably, the shuttle protein comprises an attenuated toxin protein. In particular, the shuttle protein may be *B. anthracis* derived lethal factor (LF) or oedema factor (EF). In one embodiment, the lethal factor domain I (LFn) has an amino acid sequence, which is provided herein as SEQ ID No: 11, as follows:

[SEQ ID No: 11]
MERNKTQEEHLKEIMKHIVKIEVKGEEAVKKEAAEKLLEKVPSDVLEMYKA

IGGKIYIVDGDITKHISLEALSEDKKKIKDIYGKDALLHEHYVYAKEGYEP

VLVIQSSEDYVENTEKALNVYYEIGKILSRDILSKINQPYQKFLDVLNTIK

NASDSDGQDLLFTNQLKEHPTDFSVEFLEQNSNEVQEVFAKAFAYYIEPQH

RDVLQLYAPEAFNYMDKFNEQEINLS

Thus, preferably the shuttle protein comprises or consists of an amino acid sequence substantially as set out in SEQ ID No: 11, or a variant or fragment thereof.

In a preferred embodiment, the shuttle protein also comprises a linker protein. Preferably, in the attenuated toxin, at least one toxin domain, e.g., one or more of toxic domains II-IV of the *B. anthracis* lethal factor protein toxin, is replaced by the linker protein. In a more preferred embodiment, the linker protein comprises a nucleic-acid-binding domain. For example, the nucleic-acid-binding domain may be *Saccharomyces cerevisiae* GAL4 (fused with LFn) having an amino acid sequence, which is provided herein as SEQ ID No: 12, as follows:

```
                                              [SEQ ID No: 12]
MGKPIPNPLLGLDSTMERNKTQEEHLKEIMKHIVKIEVKGEEAVKKEAAEK

LLEKVPSDVLEMYKAIGGKIYIVDGDITKHISLEALSEDKKKIKDIYGKDA

LLHEHYVYAKEGYEPVLVIQSSEDYVENTEKALNVYYEIGKILSRDILSKI

NQPYQKFLDVLNTIKNASDSDGQDLLFTNQLKEHPTDFSVEFLEQNSNEVQ

EVFAKAFAYYIEPQHRDVLQLYAPEAFNYMDKFNEQEINLSMKLLSSIEQA

CDICRLKKLKCSKEKPKCAKCLKNNWECRYSPKTKRSPLTRAHLTEVESRL

ERLEQLFLLIFPREDLDMILKMDSLQDIKALLTGLFVQDNVNKDAVTDRLA

SVETDMPLTLRQHRISATSSSEESSNKGQRQLTVSHHHHHH
```

Thus, preferably the shuttle protein comprises or consists of an amino acid sequence substantially as set out in SEQ ID No: 12, or a variant or fragment thereof.

However, the inventors have found that LFn-GAL4 was sometimes difficult to use, as it tends to non-specifically aggregate in a non-regulated way. The use of LFn-Protein Kinase R (PKR) to bind to ASOs (which are essentially DNA based rather than RNA based) is novel and is also reported here for the first time. It should be noted that LFn-PKR has not been shown to facilitate the translocation of plasmid DNA into the cytosol in the same way as LFn-GAL4 [9&10]. Therefore, the inventors have also developed a novel and improved construct whereby PKR replaces GAL4 in the above construct.

The inventors believe that PKR forms a more stable linker protein than GAL4 and that it binds to both RNA and to the double stranded part of ASOs. Therefore, in a preferred embodiment, the linker protein comprises Protein Kinase R or a fragment, variant, or mutant thereof, having an amino acid sequence, which is provided herein as SEQ ID No: 13, as follows:

```
                                              [SEQ ID No: 13]
MGKPIPNPLLGLDSTMERNKTQEEHLKEIMKHIVKIEVKGEEAVKKEAAEK

LLEKVPSDVLEMYKAIGGKIYIVDGDITKHISLEALSEDKKKIKDIYGKDA

LLHEHYVYAKEGYEPVLVIQSSEDYVENTEKALNVYYEIGKILSRDILSKI

NQPYQKFLDVLNTIKNASDSDGQDLLFTNQLKEHPTDFSVEFLEQNSNEVQ

EVFAKAFAYYIEPQHRDVLQLYAPEAFNYMDKFNEQEINLSMAGDLSAGFF

MEELNTYRQKQGVVLKYQELPNSGPPHDRRFTFQVIIDGREFPEGEGRSKK

EAKNAAAKLAVEILNKEHHHHHH
```

Thus, preferably the shuttle protein comprises or consists of an amino acid sequence substantially as set out in SEQ ID No: 13, or a variant or fragment thereof.

The inventors believe that this is an important aspect of the invention.

Hence, according to a ninth aspect of the invention, there is provided a shuttle protein comprising an attenuated toxin protein attached to Protein Kinase R (PKR).

Preferably, the shuttle protein according to the ninth aspect comprises or consists of an amino acid sequence substantially as set out in SEQ ID No: 11, or a fragment or variant thereof.

In a most preferred embodiment, the shuttle protein is coupled to a bioactive payload molecule. In some embodiments, the coupling may comprise a covalent bond. In an alternative embodiment, the coupling may comprise a non-covalent bond. In other words, the payload may be covalently or non-covalently associated with the shuttle protein. The bioactive payload molecule may be, but not limited to, a therapeutically active molecule which may be active within the cell cytosol, within the nucleus, within an organelle or intracellular structure such as a vesicle or a vacuole, within a cell surface lipid membrane or an intracellular lipid membrane. The bioactive payload molecule may further be, but not exclusively, active in of itself, or it may be inactive until it is activated within the cell. The bioactive payload molecule may also be, but is not exclusively, broken down within the cell to form active or inactive components.

The bioactive molecule may be, but limited to, a small molecule, a protein, an RNA molecule or fragment, or a DNA construct. The molecular weight of the bioactive compound may be between 1 Da and 10 MDa.

The inventors have found that the liposomes may be effectively loaded with a small molecule which is preferably therapeutically active. Therefore, in one embodiment, the bioactive payload molecule comprises a small molecule. The molecular weight of the small molecule may be 1-900 Da. Alternatively, the molecular weight of the small molecule may be 100-800 Da, 200-700 Da, 300-600 Da, or 400-500 Da. The small molecule may be, but not limited to, a pharmacological agent or a drug, which has agonistic or antagonistic properties, or may be a dye or fluorescent molecule.

The inventors have also found that the liposomes may be effectively loaded with a large molecule, such as a therapeutically active or bioactive protein. In an alternate embodiment, therefore, the bioactive payload molecule comprises a large molecule, such as a protein or enzyme. In a preferred embodiment, the protein comprises an enzyme or a fragment thereof. In a further embodiment, the protein comprises an antibody or antigen-binding fragment thereof, preferably a monoclonal antibody, or antigen-binding fragment thereof, or an antibody mimetic, or aptamer. In one embodiment, the bioactive payload molecule comprises Fab or vNAR.

In another preferred embodiment, the bioactive payload molecule comprises Diphtheria toxin A (DTA) chain linked to LFn having an amino acid sequence, which is provided herein as SEQ ID No: 15, as follows:

```
                                              [SEQ ID No: 15]
MGSSHHHHHHSSGLVPRGSHMAGGHGDVGMHVKEKEKNKDENKRKDEERNK

TQEEHLKEIMKHIVKIEVKGEEAVKKEAAEKLLEKVPSDVLEMYKAIGGKI

YIVDGDITKHISLEALSEDKKKIKDIYGKDALLHEHYVYAKEGYEPVLVIQ

SSEDYVENTEKALNVYYEIGKILSRDILSKINQPYQKFLDVLNTIKNASDS

DGQDLLFTNQLKEHPTDFSVEFLEQNSNEVQEVFAKAFAYYIEPQHRDVLQ

LYAPEAFNYMDKFNEQEINLSAMGSSHHHHHHSSGLVPRGADDVVDSSKSF

VMENFSSYHGTKPGYVDSIQKGIQKPKSGTQGNYDDDWKGFYSTDNKYDAA

GYSVDNENPLSGKAGGVVKVTYPGLTKVLALKVDNAETIKKELGLSLTEPL
```

-continued

MEQVGTEEFIKRFGDGASRVVLSLPFAEGSSSVEYINNWEQAKALSVELEI

NFETRGKRGQDAMYEYMAQACAGNR

Thus, preferably the bioactive payload molecule comprises or consists of an amino acid sequence substantially as set out in SEQ ID No: 15, or a variant or fragment thereof.

In an embodiment, the bioactive payload molecule is encoded by a nucleic acid sequence, which is provided herein as SEQ ID No: 16, as follows:

[SEQ ID No: 16]
atgggcagcagccatcatcatcatcatcacagcagcggcctggtgccgcgc ggcagccatatggcgggcggtcatggtgatgtaggtatgcacgtaaaagag aaagagaaaaataaagatgagaataagagaaaagatgaagaacgaaataaa acacaggaagagcatttaaaggaaatcatgaaacacattgtaaaaatagaa gtaaaaggggaggaagctgttaaaaaagaggcagcagaaaagctacttgag aaagtaccatctgatgttttagagatgtataaagcaattggaggaaagata tatattgtggatggtgatattacaaaacatatatctttagaagcattatct gaagataagaaaaaaataaaagacatttatgggaaagatgctttattacat gaacattatgtatatgcaaaagaaggatatgaacccgtacttgtaatccaa tcttcggaagattatgtagaaaatactgaaaaggcactgaacgtttattat gaaataggtaagatattatcaagggatattttaagtaaaattaatcaacca tatcagaaattttagatgtattaaataccattaaaaatgcatctgattca gatggacaagatctttatttactaatcagcttaaggaacatcccacagac ttttctgtagaattcttggaacaaaatagcaatgaggtacaagaagtattt gcgaaagcttttgcatattatctcgagccacagcatcgtgatgttttacag ctttatgcaccggaagcttttaattacatggataaatttaacgaacaagaa ataaatctatccgccatgggcagctctcaccaccaccaccaccactcttcc ggcctggttccacgtggtgctgacgacgttgttgactcttctaaatctttc gttatggaaaacttctcttcttaccacggtaccaaaccgggttacgtcgac tctatccagaaaggtatccagaagccgaaatctggtacccagggtaactac gacgacgactggaaaggtttctactctaccgacaacaaatacgacgccgcg ggttactctgttgacaacgaaaacccgctgtctggtaaagctggtggtgtt gttaaagttacctaccgggtctgaccaaagttctggctctgaaagttgac aacgctgaaaccatcaaaaaagaactgggtctctctctgaccgaaccgctg atggaacaggttggtaccgaagaattcatcaaacgtttcggtgacggtgct tctcgtgttgttctgtctctgccgttcgctgagggctcttcttctgttgaa tacatcaacaactgggaacaggctaaagctctgtctgttgaactggaaatc aacttcgaaacccgtggtaaacgtggccaggacgctatgtacgaatacatg gctcaggcttgtgcaggtaaccgttaa Thus, preferably the bioactive payload molecule is encoded by a nucleic acid comprising a nucleotide sequence substantially as set out in SEQ ID No: 16, or a variant or fragment thereof. Use of DTA as a payload is especially useful for treatment of cancer, such as cervical carcinoma.

The inventors have further found that the liposomes can be loaded with diagnostics such as dyes and fluorescent molecules e.g. Texas Red (example 4). Therefore, in another embodiment, the bioactive molecule is a diagnostic label. The bioactive molecule, as a diagnostic, may comprise a dye or a fluorescent molecule. The bioactive molecule, as a diagnostic, may comprise a protein (e.g. GFP), or a small molecule (e.g. Texas Red).

In some embodiments, the bioactive payload molecule or a component also may be useful in theranostics (i.e. combined therapeutic and diagnostic applications).

The bioactive payload molecule may comprise a nucleotide, which may be DNA or RNA.

The inventors have found that the liposomes (such as exosomes) may be effectively loaded with an Antisense oligonucleotide (ASO). Therefore, in one embodiment, the bioactive payload molecule comprises an ASO.

In an embodiment, the ASO may comprise an anti-Tandem dimeric tomato ASO sequence, which is provided herein as SEQ ID No: 17, as follows:

[SEQ ID No: 17]
ZZE OZE ZOO FOE ZFE ZFE ZFE GCA TGC CGG CAT CAG AGC

AGC CGG CAT

In another embodiment, the ASO may comprise an anti-Tandem dimeric tomato ASO sequence, which is provided herein as SEQ ID No: 18, as follows:

[SEQ ID No: 18]
ZZE OZE ZOO FOE ZFE ZFE ZFE GCA TGC CGG CTG CTC TGA

TGC CGG CAT

Thus, preferably the ASO comprises or consists of nucleic acid sequence substantially as set out in SEQ ID No: 17 or 18, or a variant or fragment thereof. The Table in Example 10 explains the above phosphorothioate codes.

The inventors have also found that the liposomes (such as exosomes) may be effectively loaded with an RNA molecule. Therefore, in one embodiment, the bioactive payload molecule comprises RNA. Preferably, the bioactive payload molecule comprises mRNA, miRNA, a guide RNA (for use in genome editing), or snRNA. Most preferably, the bioactive payload molecule comprises siRNA.

In another embodiment, the bioactive payload molecule comprises DNA, such as a plasmid.

As demonstrated in example 3, the inventors have shown how the liposomes of the invention can be used to successfully carry a gene-editing nuclease, such as Cas9, for use in gene editing methods. As discussed above, the inventors have demonstrated that it is possible to encapsulate the genome editing nuclease, Cas9, within the liposome of the invention, and so the liposome can be used in a genome editing technique. As also demonstrated (see example 4, 5 and 6), it is possible to trap or load both RNA analogues as well as an RNA binding protein (LFn-PKR) inside a liposome (e.g. an exosome). Consequently, the delivery of RNA or RNA analogues is possible. This means that the trapping or loading of both Cas9 and RNA inside liposomes has been shown. As Cas9 requires a guide RNA (gRNA) for target sequence specificity, both of these aspects are important for the utility of Cas9.

According to a tenth aspect, therefore, there is provided the liposome according to either the second or third aspect, for use in a genome editing technique.

According to an eleventh aspect, there is provided a genome editing method comprising loading a liposome according to the second or third aspect with (i) a guide RNA; and/or (ii) a nuclease or genetic construct encoding a nuclease, and using the loaded liposomes in a gene editing therapy.

It will be appreciated that the genome editing method can be carried out in vitro, in vivo, or ex vivo.

In one embodiment, therefore, the bioactive payload molecule comprises a genome editing tool, such as a nuclease. In a preferred embodiment, the bioactive payload molecule comprises Cas9 or Cpf1 or a TALEN or a zinc finger nuclease. Hence, the bioactive payload molecule may be used in transcription interference or transcription activation within the cells of a patient.

In one embodiment, the genome editing method may comprise loading the liposome according to the second or third aspect with a construct encoding a nuclease, such as Cas9. The construct may be a plasmid or expression vector comprising the nucleic acid sequence encoding the nuclease. In a preferred embodiment, the plasmid encodes Cas9.

According to another embodiment, there is provided a genome editing method comprising loading a liposome according to the second or third aspect with guide RNA, which targets the genetic sequence to be edited.

In one preferred embodiment, the bioactive molecule comprises Cas9 and is coupled to LFn having an amino acid sequence, which is provided herein as SEQ ID No: 14, as follows:

[SEQ ID No: 14]
MGKPIPNPLLGLDSTMERNKTQEEHLKEIMKHIVKIEVKGEEAVKKEAAEK

LLEKVPSDVLEMYKAIGGKIYIVDGDITKHISLEALSEDKKKIKDIYGKDA

LLHEHYVYAKEGYEPVLVIQSSEDYVENTEKALNVYYEIGKILSRDILSKI

NQPYQKFLDVLNTIKNASDSDGQDLLFTNQLKEHPTDFSVEFLEQNSNEVQ

EVFAKAFAYYIEPQHRDVLQLYAPEAFNYMDKFNEQEINLSLEVLFQGPMK

RNYILGLDIGITSVGYGIIDYETRDVIDAGVRLFKEANVENNEGRRSKRGA

RRLKRRRRHRIQRVKKLLFDYNLLTDHSELSGINPYEARVKGLSQKLSEEE

FSAALLHLAKRRGVHNVNEVEEDTGNELSTKEQISRNSKALEEKYVAELQL

ERLKKDGEVRGSINRFKTSDYVKEAKQLLKVQKAYHQLDQSFIDTYIDLLE

TRRTYYEGPGEGSPFGWKDIKEWYEMLMGHCTYFPEELRSVKYAYNADLYN

ALNDLNNLVITRDENEKLEYYEKFQIIENVFKQKKKPTLKQIAKEILVNEE

DIKGYRVTSTGKPEFTNLKVYHDIKDITARKEIIENAELLDQIAKILTIYQ

SSEDIQEELTNLNSELTQEEIEQISNLKGYTGTHNLSLKAINLILDELWHT

NDNQIAIFNRLKLVPKKVDLSQQKEIPTTLVDDFILSPVVKRSFIQSIKVI

NAIIKKYGLPNDIIIELAREKNSKDAQKMINEMQKRNRQTNERIEEIIRTT

GKENAKYLIEKIKLHDMQEGKCLYSLEAIPLEDLLNNPFNYEVDHIIPRSV

SFDNSFNNKVLVKQEENSKKGNRTPFQYLSSSDSKISYETFKKHILNLAKG

KGRISKTKKEYLLEERDINRFSVQKDFINRNLVDTRYATRGLMNLLRSYFR

VNNLDVKVKSINGGFTSFLRRKWKFKKERNKGYKHHAEDALIIANADFIFK

EWKKLDKAKKVMENQMFEEKQAESMPEIETEQEYKEIFITPHQIKHIKDFK

DYKYSHRVDKKPNRELINDTLYSTRKDDKGNTLIVNNLNGLYDKDNDKLKK

LINKSPEKLLMYHHDPQTYQKLKLIMEQYGDEKNPLYKYYEETGNYLTKYS

KKDNGPVIKKIKYYGNKLNAHLDITDDYPNSRNKVVKLSLKPYRFDVYLDN

-continued

GVYKFVTVKNLDVIKKENYYEVNSKCYEEAKKLKKISNQAEFIASFYNNDL

IKINGELYRVIGVNNDLLNRIEVNMIDITYREYLENMNDKRPPRIIKTIAS

KTQSIKKYSTDILGNLYEVKSKKHPQIIKKGYPYDVPDYAENLYFQGHHHH

HH.

Thus, preferably the bioactive molecule comprises or consists of an amino acid sequence substantially as set out in SEQ ID No: 14, or a variant or fragment thereof.

It will be appreciated that the liposomes and the bioactive payload molecule encapsulated within the liposome may be used in a medicament, which may be used as a monotherapy, for treating, ameliorating, or preventing a disorder (e.g. FMO5-regulated obesity, prostaglandin-D2-regulated diseases, such as androgenetic alopecia, acne, rosacea, prostate cancer, Zika fever, Ebola virus disease, acquired immunodeficiency syndrome, Stat3-responsive cancer, P53-deficient cancer, virally mediated cervical cancer, familial hypercholesterolemia, Duchene muscular dystrophy, spinal muscular atrophy, Crone's disease, and various inflammatory diseases), or for genome editing using nucleases (e.g. Cas9). Alternatively, the liposomes according to the invention may be used as an adjunct to, or in combination with, known therapies for treating, ameliorating, or preventing a disorder or the symptoms of the disorders.

The liposomes according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given.

The liposomes according to the invention may also be incorporated within a slow- or delayed-release device. Such devices may, for example, be inserted on or under the skin, and the medicament may be released over hours, days, weeks or even months. The device may be located at least adjacent the treatment site. Such devices may be particularly advantageous when long-term treatment with the liposomes is required and which would normally require frequent administration (e.g. at least daily injection).

Medicaments of liposomes may be administered to a subject by injection into the blood stream, a nerve or directly into a site requiring treatment. Injections may be intravenous (bolus or infusion) or subcutaneous (bolus or infusion), intradermal (bolus or infusion), intrathecal (bolus or infusion) or into cerebral spinal fluid (CSF) via an epidural or spinal tap (bolus or infusion).

It will be appreciated that the amount the liposomes that is required is determined by its the bioactive payload molecule encapsulated within, and its biological activity and bioavailability, which in turn depends on the mode of administration, the physiochemical properties of the liposomes and the bioactive payload molecule encapsulated within and whether it is being used as a monotherapy or in a combined therapy. The frequency of administration will also be influenced by the half-life of the payload molecule as well as the half life of the target molecule (i.e. a protein), within the subject being treated. Optimal dosages to be administered may be determined by those skilled in the art and will vary with the particular liposomes and the particular bioactive payload molecule in use, the strength of the pharmaceutical composition, the mode of administration, and the advancement of disorder or symptoms to be treated. Additional factors depending on the particular subject being treated will result in a need to adjust dosages, including subject age, weight, gender, diet, and time of administration.

Generally, a daily dose of between 0.001 μg/kg of body weight and 10 mg/kg of body weight, or between 0.01 μg/kg of body weight and 1 mg/kg of body weight, of the payload molecule according to the invention may be used for treating, ameliorating, or preventing a certain disorder or symptoms of a certain disorder, depending upon the liposomes and the bioactive payload molecule used.

The liposomes may be administered before, during or after onset of the disorder or symptoms being treated. Daily doses may be given as a single administration (e.g. a single daily injection or inhalation of a nasal spray). Alternatively, the liposomes may require administration twice or more times during a day.

As an example, the liposomes may be administered as two (or more depending upon the severity of the disorder being treated) daily doses of between 0.07 μg and 700 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of the liposomes according to the invention to a patient without the need to administer repeated doses.

Known procedures, such as those conventionally employed by the pharmaceutical industry (e.g. in vivo experimentation, clinical trials, etc.), may be used to form specific formulations of the liposomes according to the invention, precise therapeutic regimes (such as daily doses of the agents and the frequency of administration), or the amount of the bioactive payload molecule encapsulated within the liposomes. The inventors believe that they are the first to suggest the loading of liposomes by the methods described herein.

According to a thirteenth aspect, there is provided a pharmaceutical composition comprising the liposome according to the second or third aspect, and a pharmaceutically acceptable vehicle.

According to a fourteenth aspect, there is provided a method of preparing the pharmaceutical composition according to the thirteenth aspect, the method comprising contacting the liposome according to either the second or third aspect, with a pharmaceutically acceptable vehicle.

A "subject" may be a vertebrate, mammal, or domestic animal. Hence, compositions and medicaments according to the invention may be used to treat any mammal, for example livestock (e.g. a horse), pets, or may be used in other veterinary applications. Most preferably, however, the subject is a human being.

A "therapeutically effective amount" of the liposomes and the bioactive payload molecule encapsulated within, is any amount which, when administered to a subject, is the amount of the aforementioned that is needed to treat any disorders or symptoms of disorders.

For example, the therapeutically effective amount of the liposomes and the bioactive payload molecule encapsulated within used may be from about 0.01 mg to about 800 mg, and preferably from about 0.01 mg to about 500 mg. It is preferred that the amount of the liposomes and the bioactive payload molecule encapsulated within is an amount from about 0.1 mg to about 250 mg, and most preferably from about 0.1 mg to about 20 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. The pharmaceutically acceptable vehicle may also be configured for controlled release within the body, e.g. in the stomach, blood or other internal organs and structures by using appropriate encapsulations e.g. enteric encapsulation. In powders, the vehicle is a finely divided solid that is in admixture with the finely divided active agents according to the invention. In tablets, the active agent (e.g. the liposomes and the bioactive payload molecule encapsulated within according to the invention) may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The liposomes according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The liposomes may be prepared as a sterile solid composition that may be dissolved or suspended at the time of administration using sterile water, saline, or other appropriate sterile injectable medium.

The liposomes of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The liposomes according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions. Alternatively, the liposomes could be administered rectally e.g. via an enema.

It will be appreciated that the invention extends to any nucleic acid or peptide or variant, derivative or analogue thereof, which comprises substantially the amino acid or nucleic acid sequences of any of the sequences referred to herein, including variants or fragments thereof. The terms "substantially the amino acid/nucleotide/peptide sequence", "variant" and "fragment", can be a sequence that has at least 40% sequence identity with the amino acid/nucleotide/peptide sequences of any one of the sequences referred to herein, for example 40% identity with the sequence identified as SEQ ID Nos: 1-14.

Amino acid/polynucleotide/polypeptide sequences with a sequence identity which is greater than 65%, more preferably greater than 70%, even more preferably greater than 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gappenalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (v) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as $(N/T)*100$, where N is the number of positions at which the sequences share an identical residue, and T is the total number of positions compared including gaps and either including or excluding overhangs. Preferably, overhangs are included in the calculation. Hence, a most preferred method for calculating percentage identity between two sequences comprises (i) preparing a sequence alignment using the ClustalW program using a suitable set of parameters, for example, as set out above; and (ii) inserting the values of N and T into the following formula:—Sequence Identity=$(N/T)*100$.

Alternative methods for identifying similar sequences will be known to those skilled in the art. For example, a substantially similar nucleotide sequence will be encoded by a sequence which hybridizes to DNA sequences or their complements under stringent conditions. By stringent conditions, the inventors mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in, for example, SEQ ID Nos:1 to 14.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent (synonymous) change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figure, in which:

FIG. 1 is an image from an optical microscope (LSM880 via an Airyscan detector (Carl Zeiss Ltd) showing the localisation of Texas red-labelled cargo (i.e. Texas Red labelled LFn-PKR) to intraluminal structures within HeLa cells stained with α-CD63 (3 h chase). The panels show Texas Red labelled LFn-PKR (centre); α-CD63 (right); and the merged image (left);

EXAMPLES

The inventors have developed a novel method of producing liposomes (e.g. exosomes) and a novel cellular delivery system comprising these liposomes for stealth delivery of biologically and therapeutically active payload molecules, such as small molecules, antisense oligonucleotides (ASOs), RNA molecules (e.g. siRNA), bioactive proteins, genome editing tools (e.g. cas9) and drugs into cells for treating a range of disorders.

Figure 7:
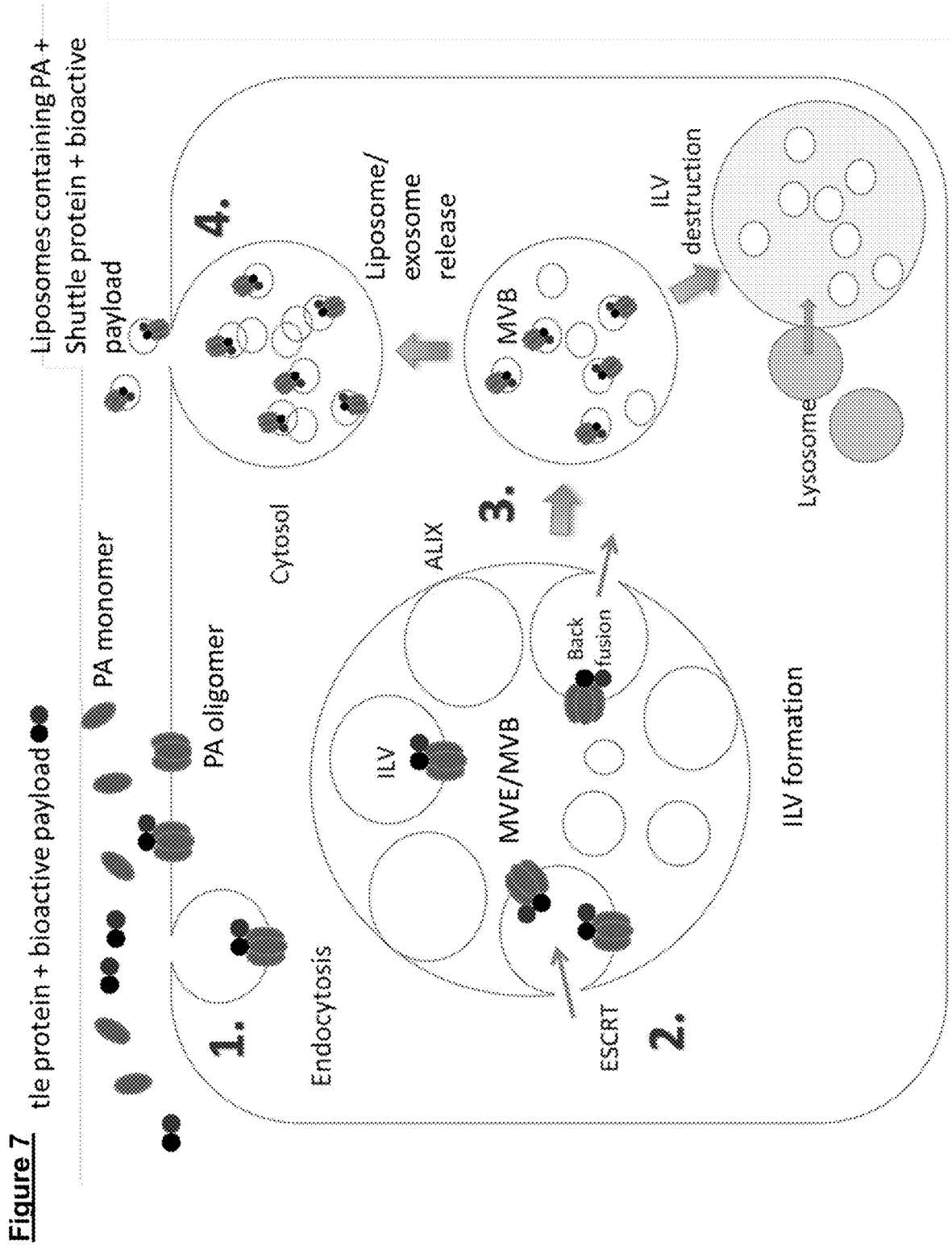
FIG. 7 is a schematic diagram showing the cellular production of liposomes (i.e. exosomes) of the invention.

Referring to FIG. 7, there is shown a schematic drawing summarising the four stages (explained below) by which the liposomes of the invention are produced:
1. The pore-forming protein (e.g. PA83) oligomerises in the membrane of the cell, thereby creating a pore, and the shuttle protein (e.g. LFn or PKR), which is optionally attached to a bioactive payload molecule (e.g. siRNA or Cas9 or an ASO etc.), interacts with the pore-forming protein and is internalised into the cell by endocytosis thereby forming an endocytic vesicle.
2. Endosomal sorting complexes required for transport (ESCRT) machinery transports the endocytic vesicle, which is loaded with the pore-forming protein and the shuttle protein, which is optionally attached to a bioactive payload molecule, to multivesicular bodies (MVBs) where the endocytic vesicles form intraluminal vesicles (ILVs).
3. Back-fusion events between ILVs, within a MVB, and the limiting membrane of the MVB during an apoptosis-linked gene 2-interacting protein X (ALIX) dependent process subvert the endomembrane system (which would usually result in fusion to lysosomes and destruction of the ILVs) to access the cytosol.
4. The MVB, comprising ILVs loaded with the pore-forming protein and the shuttle protein, which is optionally attached to a bioactive payload molecule, are then released from liposomes/exosomes containing the pore-forming protein and the shuttle protein, which is optionally attached to a bioactive payload molecule.

Materials and Methods

General Chemicals, Fluorescent Probes and Reagents

General laboratory reagents were from Sigma Aldrich (Dorset, UK) unless otherwise stated. Texas Red-N-hydroxysuccinimide ester (TxR-SE) was from Invitrogen (Paisley, UK). Dulbecco's Minimal Essential Medium, Eagles-Minimal Essential Medium, Non-essential amino acids, penicillin, streptomycin and glutamine solutions were all from Gibco (ThermoFisher Scientific, Paisley UK), Blasticidin solution was from Invitrogen (Paisley UK) and Ionomycin was from Sigma Aldrich (Dorset UK). Mouse Monoclonal anti-CD63 was from AbCam and monoclonal anti-Lamp2 was form DHSB (University of Iowa, IA, USA). Alexaflour 488-labeled goat anti-mouse antibody was from Invitrogen (Paisley UK). Goat anti-Texas Red monoclonal antibody and HRP-conjugated donkey anti-goat antibodies were from Vector Labs. The exoEasy Maxi kits (20) (Cat No: 76064) were from QIAgen and Total exosome Isolation reagent (from cell culture media) (Cat No: 4478359) (PEG solution) was from Invitrogen (Paisley UK). Stealth RNAi™ siRNA GFP Reporter Control (Cat No: 12935145) was from Invitrogen (Paisley UK) and was supplied as a 20 μM solution.

Exosome-Free Media

Bovine liposomes/exosomes in FCS were sedimented at 180 000×g for 18 h at 4° C. The supernatant was collected and added to serum free but otherwise complete media (MEM) and filter sterilized (0.2 μm filter, Sartorus) under negative pressure.

Cell Culture

The culture and passage of HeLa (ATCC: CCL2) and HEK293 (AMSBIO: SCO08) cells were performed as described by the supplier. Cells for microscopy were seeded onto sterile coverslips at a density of $1 \times 10^5$ cells/well. Fixation, antibody hybridization and detection were performed as previously described [2]. CD63 immunostained cells were fixed in cold methanol.

Protein Production, Isolation and Enrichment

The DNA sequence coding for the protein PA83 (based upon GenBank accession numbers AAF86457 and AAT98414) has been previously described [2]. LFn-PKR was synthesized by BioBasic Inc., (Ontario, Canada) using the GenBank accession number AAY15237 (for LFn) and NM_002759 (for PKR). The open reading frame coding for LFn-PKR was sub-cloned into the bacterial expression cassette pET151/D (Invitrogen, Paisley, UK) as described previously in [2] and in PCT/GB2014/051918. Plasmids encoding LFn-*Staphylococcus aureus* (Sa) Cas9 and GST-PA63 were synthesized by Invitrogen using the pET151 bacterial expression system as the parent plasmid. The GST sequence used was from pGEX3x and the SaCAS9 sequence was codon optimised (i.e. SEQ ID No:14) from Genbank accession number CCK74173.1. The addition of a V5 epitope tag and a 6× histidine affinity tag allowed immunodetection and affinity purification of the protein from bacterial lysate.

LFn-PKR and PA83 were enriched from cultures of *E. coli* with a yield of approximately 2 mg/L (LFn-SaCas9 was approximately 0.5 mg/L). Using chemically competent *E. coli* BL21*DE3pLys (Invitrogen, Paisley, UK) transformed with 10 ng of plasmid and cultured overnight in 2×YT containing 200 µg/mL ampicillin (Sigma, Dorset, UK) and then grown in 1000 mL of 2×YT at 37° C. and 200 rpm for 3 h. Subsequently, isopropylthio-β-galactoside (IPTG) (Sigma, Dorset, UK) was added to a final concentration of 1 mM and incubated for a further 3 h. Bacterial pellets prepared by centrifugation (6 000×g for 6 min at 4° C.) were lysed using a French Press (Thermo Scientific, Paisley, UK) set to 15 000 psi. Lysates were cleared (20 000×g for 20 min at 4° C.) and the supernatant passed over a 6× histidine affinity chromatography column (Talon® resin; Clontech, Saint-Germain-en-Laye, France). The 6×His containing proteins were eluted using 150 mM imidazole (Sigma, Dorset, UK) in PBS, in fractions of 1 mL. Protein fractions were analyzed for purity and concentration, pooled, dialyzed to exhaustion against PBS and finally filter sterilized (0.2 µm filter, Sartorus). The final protein preparation was evaluated by SDS-PAGE and subjected to Coomassie staining (to determine purity) and Western blot analysis using the antibodies described.

Synthesis and Characterization of Probes

LFn-PKR-TxR and LFn-SaCas9-TxR were prepared using methods previously described [14]. Briefly, TxR-SE (5 mg) was dissolved in DMSO (5 mL). To 2.5 mL of PBS, 100 µL of the TxR solution was added to approximately 5 mg of recombinant protein and left in the dark at 25° C. for 1 h. The product was purified using PD-10 columns (GE Healthcare, Chalfont St Giles, UK) and PBS as eluent to collect 0.5 mL fractions. The most optically dense fractions were then selected and pooled to give either the LFn-PKR-TxR or the LFn-SaCas9-TxR conjugates. Fluorescent conjugates were then filter sterilized (0.2 m filter, Sartorus) and frozen at −80° C.

Cell Culture for Exosome Loading

Cells were seeded in 175 cm$^2$ TC treated dishes and left to grow under standard incubation conditions i.e. 37° C. in 5% (v/v) $CO_2$. At 90% confluence, the cell monolayer was washed three times in PBS prior to exosome loading.

Loading Liposomes/Exosomes with LFn-PKR-TxR or LFn-SaCas9-TxR

Cells were incubated with PA83 (50 µg/mL) and LFn-PKR-TxR (50 µg/mL) or LFn-SaCas9-TxR (50 µg/mL) in 3 mL of serum free DMEM at 37° C. for 1 hour. After 1 h, 5 mL of exosome free DMEM with 10% (v/v) FCS was added to a final volume of 8 mL and plates were left to incubate at 37° C. for 3 h.

Loading Liposomes/Exosomes with LFn-PKR::siRNA

LFn-PKR (50 µg/mL) was left to incubate with GFP siRNA (50 nM) in serum free DMEM for 5 minutes previous to adding PA83 (50 µg/mL). The mixture was then added to the cell monolayer and cells were incubated at 37° C. for 1 hour. After 1 h, 5 mL of exosome free DMEM with 10% (v/v) FCS was added to a final volume of 8 mL and plates were left to incubate at 37° C. for 3 h.

Liposome/Exosome Isolation

Ionomycin (50 µM) was added to the media and left to incubate for 30 minutes under standard conditions. The media was then collected and cell debris sedimented after centrifugation at 1,500×g for 2 min at 4° C. The resulting supernatant was filter sterilized (0.8 µm, Sartorous) prior to freezing or exosome isolation. Exosome isolation was performed using one of three methodologies:

1. Differential Centrifugation

This was modified from [15]. Briefly, frozen filtered conditioned media was thawed on ice, and subject to 10 000×g for 30 min to sediment EVs. The supernatant was then subject to 110 000×g at 4° C. for 70 min and the pellet collected in 1 mL of PBS. The re-suspended pellet was then subject to a second round of sedimentation at 100 000×g for 70 min 4° C. The resulting pellet was then suspended in 1000 µL of exosome-free media, filtered through a 0.2 m filter (Sartorus) and stored frozen at −20° C. until required.

2. Isolation by Polyethylene Glycol Precipitation

Briefly, the volume of the cleared and filtered cell culture media was estimated and to this, 0.5 volumes of the Isolation reagent was added. This preparation was left overnight at 4° C. The mix was then centrifuged at 10,000×g for 1 h at 4° C. The resulting pellet was then suspended in a final volume of 1000 µL of exosome-free media and stored frozen at −20° C. until required.

3. Isolation by Membrane Adsorption

This was performed using the QIAgen exoEasy Kit according to manufacturer's specifications. Briefly, 8 mL of XPB buffer was mixed with the cell culture reagent and after the isolation, an additional step was added to remove the elution (XE) buffer from the exosome preparation. This was achieved by centrifuging the eluate at 110 000×g for 70 min at 4° C. The resulting pellet was then suspended in 1000 µL of exosome-free media and stored frozen at −20° C. until required.

Protein Quantification

The bicinchoninic acid assay (BCA) assay was performed according to the Bicinchoninic Acid Kit (BCA-1) (Sigma Aldrich, Dorset UK) specification to determine protein concentrations of final exosome samples previous to storage. Additionally, a ulite (BioDrop Inc.) apparatus was used to determine DNA and protein concentrations at $OD_{260}$ and $OD_{280}$, respectively, following the manufacturer's recommended protocols.

Microscopy

Microscopic visualisation of liposomes/exosomes was performed by mixing an equal volume of the exosome preparation with an equal volume of cell mask reagent which incorporated a Cy5 fluorophore (Cat. No. C10046; Invitrogen, Paisley, UK). This allowed the imaging of liposomes/exosomes under fluorescence using a LSM880 laser scanning confocal microscope fitted with an Airyscan unit (Carl Zeiss Ltd, Germany). The super-resolution capabilities of the Airyscan unit made the resolution of liposomes/exosomes possible. For liposomes/exosomes loaded with Texas-red labelled proteins, the liposomes/exosomes were visualised directly using the super resolution capabilities of the LSM880's Airyscan unit (Carl Zeiss Ltd, Germany). In both instances a Plan-Apochromat 63×/1.40 numerical aperture Oil DIC f/ELYRA objective was used. Immunostaining was performed on either paraformaldehyde fixed or cold (20° C.) methanol fixed cells grown on coverslips as previously described.

Assaying siRNA Activity

To assess the delivery of siRNA, control siRNA specific for GFP was purchased. This was directed against a stably expressed transgene expressed in the HEK293 (SCOO8) cells and used as a standard to report on gene activity. HEK293 cells overexpressed GFP fused in frame to beta-galactosidase, an enzyme responsible for the hydrolysis of x-gal from a colourless precursor to an insoluble blue compound, was detected spectrophotometrically at 620 nm. Consequently, it was possible to monitor GFP siRNA activity by measuring beta-galactosidase mediated X-gal conversion. Finally, beta-galactosidase activity was expressed as a percentage of the untreated control, after normalising it ($OD_{620}$) to protein concentration.

Cell Culture for Gene Modulation Assay

Activity was assessed using 6-well plates. Cells were seeded at $5\times10^5$ cells/well (HEK293, AMSBIO) and left to incubate at 37° C. in 5% (v/v) $CO_2$ for 24 h prior to treatment.

Dosing with Liposomes/Exosomes

Cells were treated with 200 µL of exosome preparation, diluted in 2 mL of complete media. This preparation was filter sterilised (0.2 µm filter, Sartorus) prior to being incubated with the cells for the desired time (24 h, 48 h, 72 h).

Assaying Gene Modulation

Media was discarded, and cell monolayer was carefully washed 3 times in chilled PBS, prior to adding 500 µL of RIPA buffer (R0278-50ML, Sigma Aldrich) to each well. Following a 15 min incubation period on ice, the cell lysate from each well was aspirated 10 times and decanted into a labelled Eppendorf. After centrifugation at 21,000×g for 10 min at 4° C., the supernatant was transferred into a new Eppendorf and the pellet discarded. Then, 10 µL of lysate were added to 100 µL of 2% BCA reagent in a 96-well plate and incubated at 37° C. The remaining 400 µL of supernatant were mixed with 12 µl of X-gal (50 mM in DMSO) (R0404, ThermoFisher) and transferred into a 96-well plate at 100 µL/well. X-Gal conversion was assayed over time (readings taken every 15 min over 5 hours) at 620 nm using the spectrophotometer set to 37° C.

Western Blotting and TCA Precipitation

Western blotting and immunodetection was performed using the mini-tetracell apparatus (BioRad) following the manufacturer's instructions. For protein separation, a 10% (w/v) acrylamide gel was used and run for 60 min at 200 V. Transfer onto nitrocellulose membrane was performed at 400 mM for 60 min. Blocking was performed for 45 min using 5% (w/v) non-fat dried milk solution in PBS containing 0.1% (v/v) tween 20 reagent. Antibody hybridisations were performed in 3 mL at 37° C. for 60 min under shaking conditions using the antibody dilutions suggested by the manufacturer. The detection of HRP-labelled secondary antibodies was performed using enhanced ECL reagent (Pierce, ThermoFisher Scientific) following the manufacturer's instructions. Gels and blots were calibrated by running broad range pre-stained protein markers (Invitrogen). TCA precipitation of exosome proteins was performed by adding 0.6 volumes of TCA to the exosome preparation. This was then left to incubate at 4° C. for 30 min. The preparation was then sedimented at 21 000×g for 10 min at 4° C. and the pellet washed twice in acetone, also at 4° C. The resulting pellet was dissolved in Laemmli buffer, subject to western immunoblotting and probed with either an anti-LAMP2 specific primary antibody (DHSB, University of Iowa, IA, USA) under non-reducing conditions; or a Texas Red specific primary antibody (Vector labs) using dilutions suggested by the manufacturers.

Example 1—Liposomes are Taken Up by Cells

Figure 1:
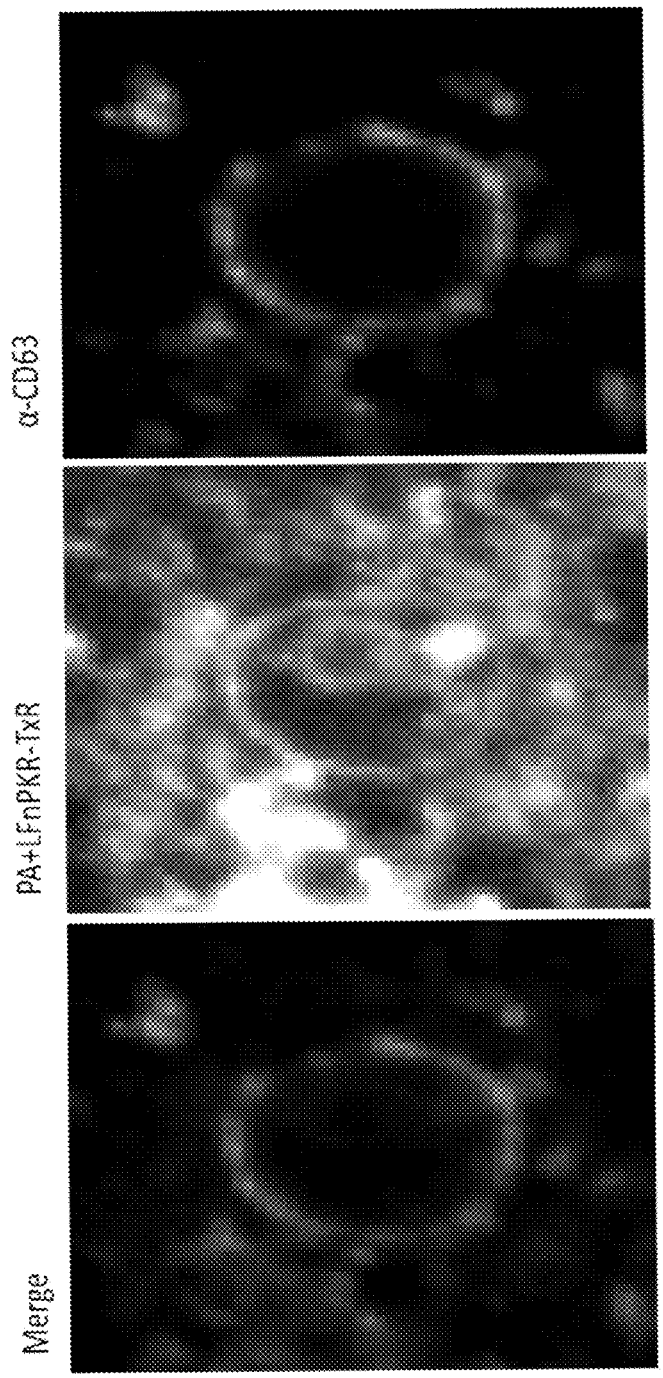

As shown in FIG. 1, Texas red-labelled cargo (i.e. Texas Red labelled LFn-PKR) localises to intraluminal structures within HeLa cells. As these intraluminal structures are positive for the exosome immunomarker CD63 (also known as LAMP3), it is likely that this intraluminal signal is within multivesicular endosomes, i.e. late endosomes. This shows that Texas Red labelled LFn-PKR is, when added to cells with PA83, able to preferentially label intraluminal membrane within MVE/MVBs 3 h after being added to cells.

Example 2—Liposomes are a Similar Size to Physiological Exosomes

Figure 2:
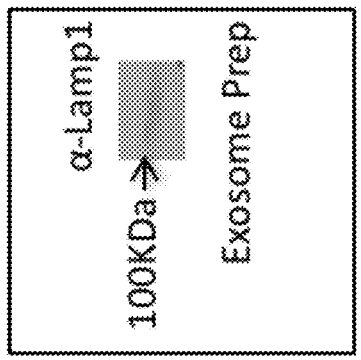
FIG. 2 is an image of liposomes/exosomes isolated form HeLa cells stained with (Cy5) cell mask.
Figure 2:
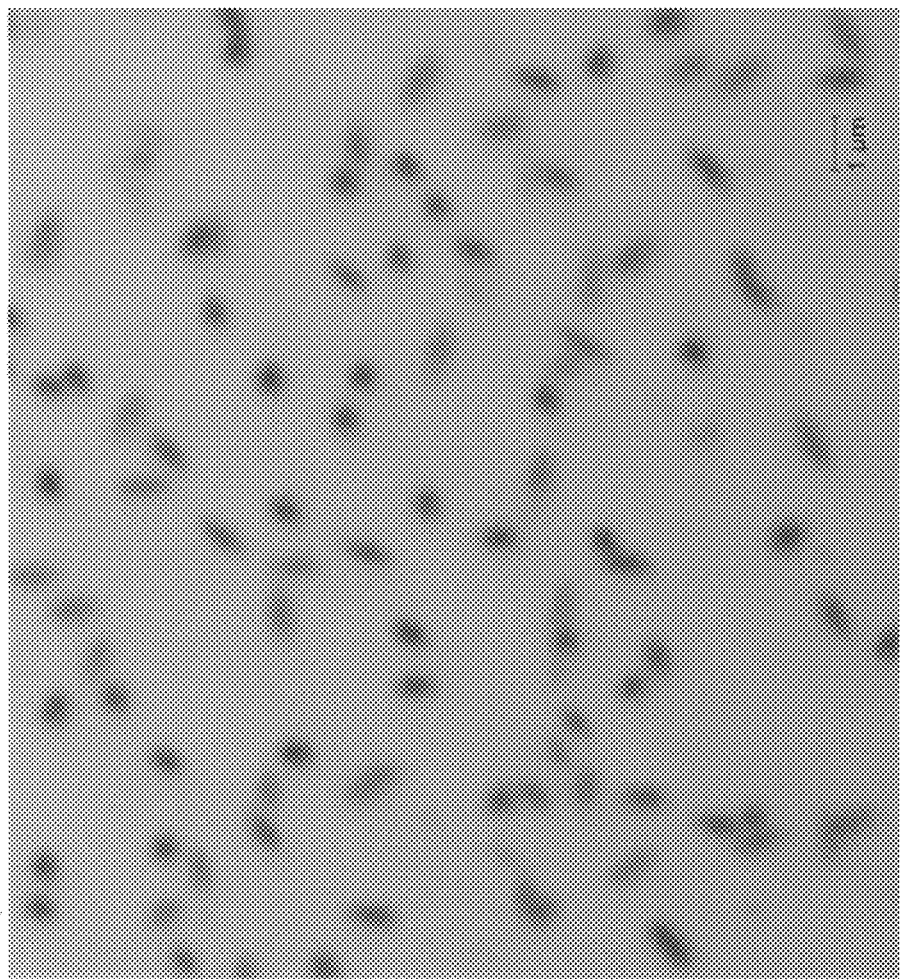

FIG. 2 shows the inventor's findings which demonstrate that liposomes/exosomes isolated from Hela conditioned media, stained with Cy5-Cell Mask, and visualised using an Airyscan detector were approximately the right size for exosomes (60-120 nm). It should be noted that the limits of this system's resolution are 120 nM in the x-y plain. Liposomes/exosomes isolated from the exoEasy kit were also subject to immunoblotting analysis using LAMP2 as a probe and, as would be predicted, a band is visible within the exosome preparation at approximately the right molecular weight. This means that the liposomes/exosomes isolated using the exoEasy kit were not only approximately the correct size but also contained well characterised exosome immunomarkers as would be predicted.

Example 3—Liposomes can be Loaded with Cas9

Figure 3:
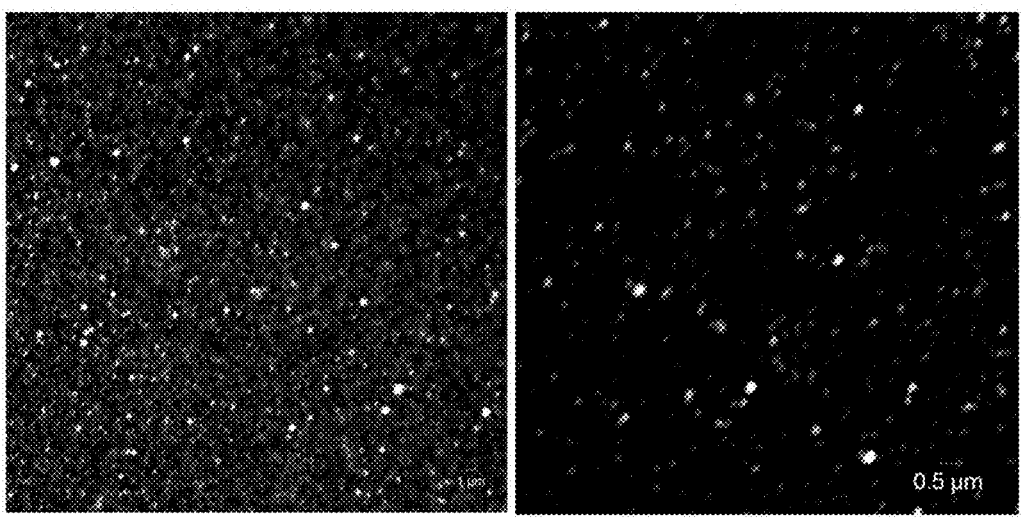
FIG. 3 is an image from an optical microscope showing exosome preparations from HeLa cells exposed to PA83 and Texas Red-labelled LFn-SaCAS9 using two different magnifications.
Figure 3:
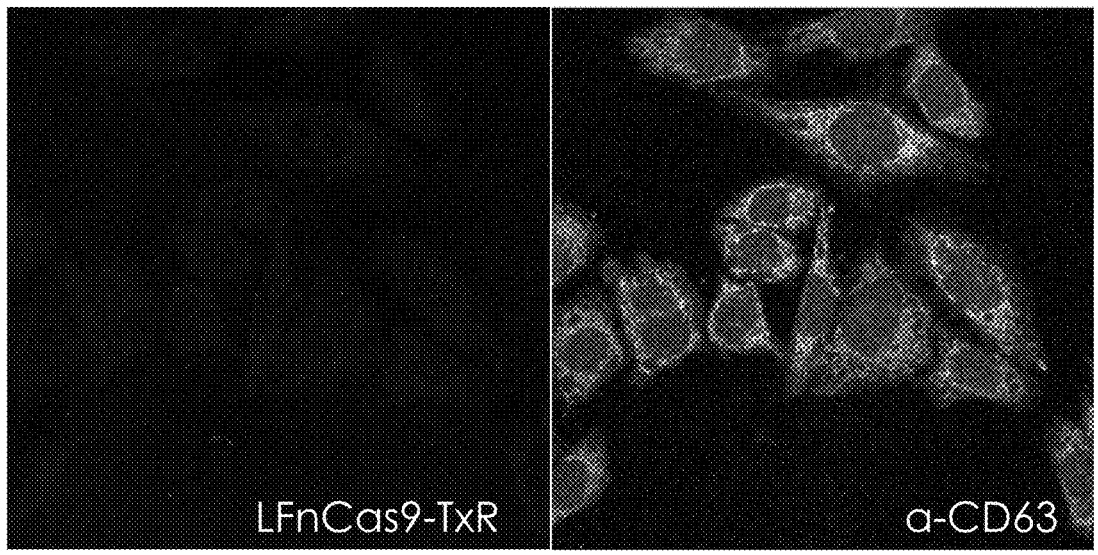

Liposomes/exosomes have been effectively loaded with *Staphylococcus aureus* Cas9, i.e. SaCAS9. In FIG. 3, the red signal from the LFn-SaCAS9 can be clearly seen in exosome preparations from Hela cells exposed to PA83 and Texas Red-labelled LFn-SaCAS9. Control liposomes/exosomes R with: no PA83, no cargo or a non-translocation cargo (BSA-Texas Red) did not produce any red signal even when incubated with cell mask to check the plane of focus (FIG. 3B).

Example 4—Liposomes can be Loaded with Small Molecules

Figure 4:
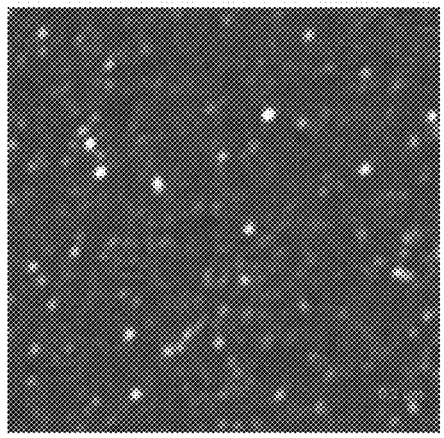
FIG. 4 is an image showing the results of exosome preparations from Hela cells exposed to PA83 and Texas Red-labelled LFn-PKR (Panel A) or PA83 and Texas Red-labelled BSA (Panel B, control) after 3 h.
Figure 4:
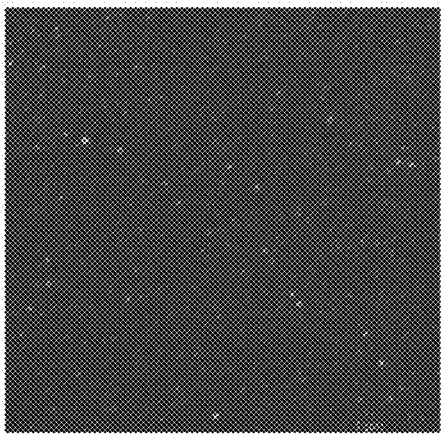
Figure 4:
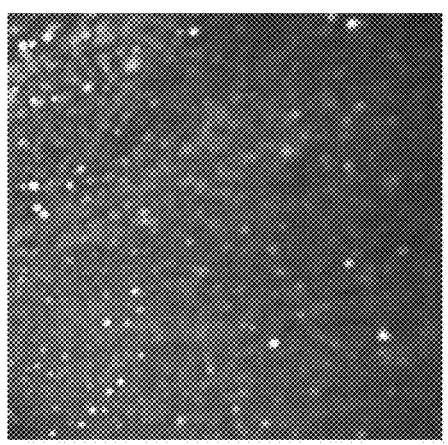
Figure 4:
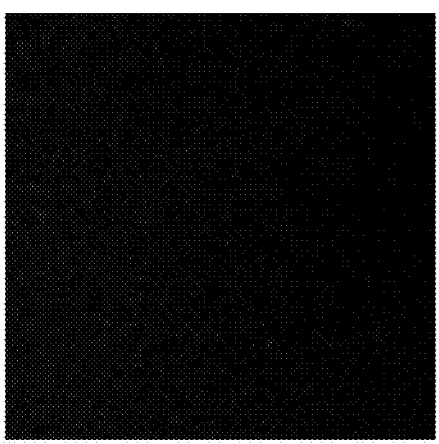

Liposomes/exosomes have been further shown to be effectively loaded with small molecules. In FIG. 4, the small molecule, Texas Red, is shown to be taken up by exosome preparations from Hela cells exposed to PA83 and Texas Red-labelled LFn-PKR or PA83 after 3 h. Texas Red-labelled BSA was used as a negative control. Here Texas Red-labelled LFn-PKR can be readily detected within cell mask positive populations of liposomes/exosomes whereas Texas Red-labelled BSA cannot.

Example 5—Loaded Protein is Present in Isolated Liposomes

Figure 5:
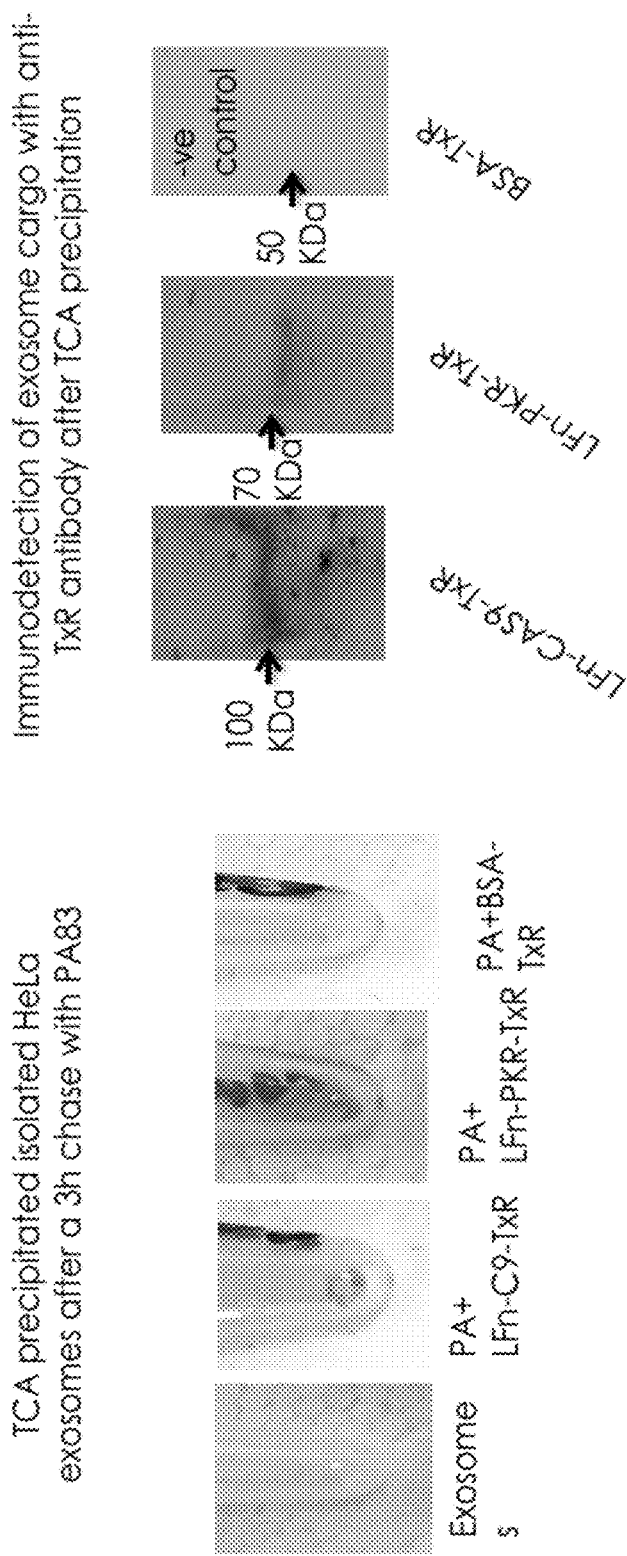
FIG. 5 is the result of TCA precipitating liposomes/exosomes prepared with PA83 and either: Texas Red-labelled LFn-SaCAS9, Texas Red-labelled LFn-PKR, or Texas Red-labelled BSA.

FIG. 5 shows the result of TCA precipitating liposomes/exosomes prepared with PA83 and either: Texas Red-labelled LFn-SaCAS9, Texas Red-labelled LFn-PKR, or Texas Red-labelled BSA. From the PA83 Texas Red labelled LFn-SaCAS9 and PA83 Texas Red labelled LFn-PKR preparations, Texas Red is clearly visible in the pellet. Texas Red is not readily detectable for the "no treatment" or PA83 and BSA-Texas Red "treated" controls. Similarly, after immunoblotting and detection using a Texas Red specific primary antibody, Texas Red was detected labelling proteins of the predicted molecular weight from the same TCA precipitate as before.

Example 6—Liposomes Loaded with siRNA are Effective at Down-Regulating Proteins

Figure 6:
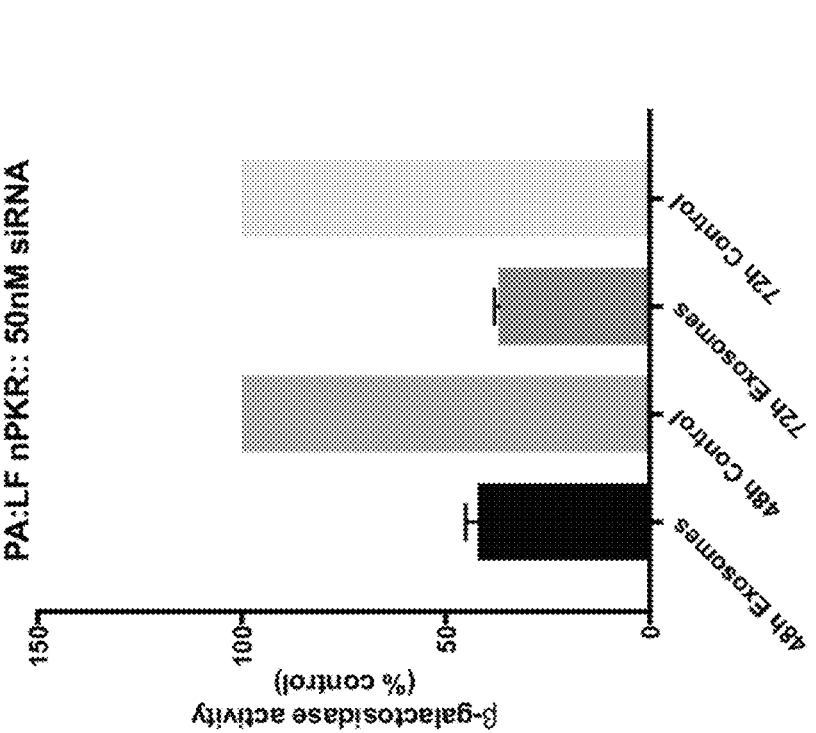
FIG. 6 is the biological activity of β-galactosidase in cells treated with control liposomes/exosomes, and cells treated with liposomes/exosomes loaded with siRNA targeting β-galactosidase translation.
Figure 6:
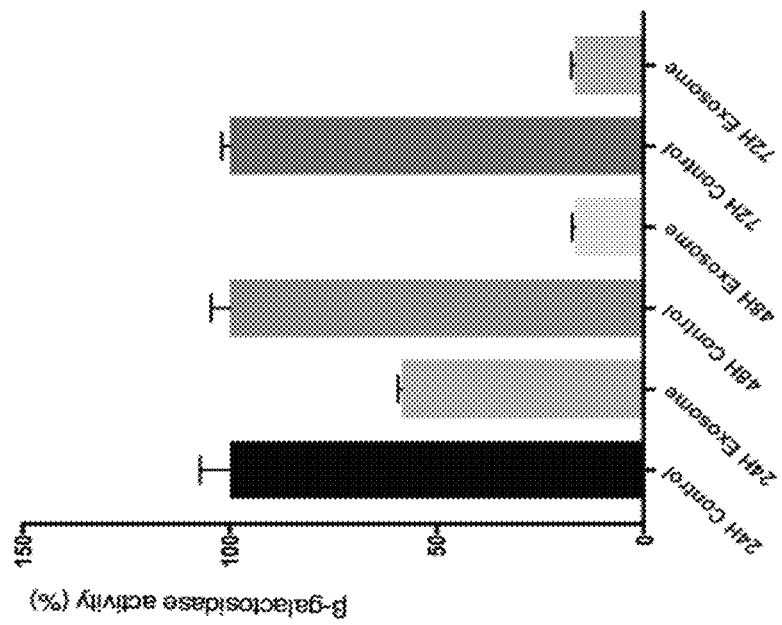

The biological activity of liposomes/exosomes isolated form cell culture media using the exoEasy kit and differential centrifugation is shown in FIG. 6. Here a reduction of beta-galactosidase activity per unit cell protein was recorded demonstrating 1) the inventors' ability to load siRNA into liposomes/exosomes and 2) the biological activity of the siRNA loaded liposomes/exosomes i.e. their ability to deliver siRNA into the cytosol of a second population of cells.

Example 7—Treatment of Zika Virus Infection

As a theoretical example, the liposomes produced by the method of the first aspect are used to treat a patient who has contracted the Zika virus. Firstly, a biopsy is carried out on the patient, and a number of the patient's cells are isolated. Liposomes are then produced from the cells using the method of the first aspect, and loaded with anti-Zika virus siRNA. The liposomes containing the anti-Zika virus siRNA are then administered to the patient and are up-taken by the patents cells via endocytosis. The anti-Zika virus siRNA is therefore present in the patient's cells and the ability of the Zika virus to multiply in the patient's body is inhibited.

Example 8—Treatment of Obesity

As another theoretical example, the liposomes produced by the method of the first aspect are used to treat a patient who is suffering from FMO5-regulated obesity. In this example, liposomes are then derived from cultured mesenchymal stem cells using the method of the first aspect, and loaded with anti-FMO5 siRNA. The liposomes containing the anti-FMO5 siRNA are then administered to the patient and are up-taken by the patient's cells via endocytosis. The anti-FMO5 siRNA is therefore present in the patient's cells and the FMO5 enzyme is down-regulated and the patient no longer presents obesity-related symptoms.

Discussion

The materials which the inventors have loaded into liposomes/exosomes using PA83::LFn fusions include: low molecular weight covalent conjugates (i.e. Texas Red), LFn-PKR::siRNA, LFn-PKR conjugated-Texas Red, LFn-Gal4::eGFP-Rab5 and LFn-SaCAS9 conjugated-Texas Red. Consequently, the data presented here supports the novel idea that LFn fusion proteins can deliver selective cargo (rather than just LF or EF) into a biologically derived, stealth delivery system termed an exosome. Here, for the first time, a methodology that can achieve exosome loading without cargo overexpression or exosome disruption is disclosed and the evidence to support this conclusion discussed.

FIG. 1 demonstrates that Texas Red-labelled LFn-PKR can, in the presence of PA83, associate with intraluminal vesicles within a CD63 positive, membrane-delimited structure. These data support the hypothesis that LFn-PKR uses a similar cytosolic translocation pathway to wild type LF [3]. FIG. 2 validates the isolation of liposomes/exosomes using the QIAgen exoEasy kit through both microscopy (measuring vesical size) and immunoblotting detection of the exosome marker LAMP2 within a population of isolated liposomes/exosomes. This data indicates that liposomes/exosomes have indeed been isolated. FIG. 3 provides evidence that the isolated liposomes/exosomes contain cargo protein labelled with the fluorophore Texas Red. In this instance the cargo protein is LFn-SaCAS9, which has previously been reported to be unlikely to act as a PA translocase substrate. Here LFn-SaCas9 has been documented within populations of isolated liposomes/exosomes. FIG. 4 (panel a) duplicates this methodology showing reproducibility only this time using different cargo protein: Texas Red-labelled LFn-PKR. This further demonstrates the ability of this system to move selected small molecules, covalently conjugated to PA pore substrates like LFn-fusion proteins, into populations of liposomes/exosomes. FIG. 4 (panel B) serves as a negative control showing that: 1) BSA labelled-Texas Red doesn't act as a PA translocase substrate, 2) that the signal documented is specific to Texas Red and not attributable to either autofluorescence of bleed from the Cy5 cell mask channel.

FIG. 5 demonstrates that the Texas Red signal from isolated liposomes/exosomes was able to be precipitated using trichloroacetic acid (TCA) (i.e. attached to a protein) and that after Western analysis, it was of the predicted molecular weight. This indicates that the protein was intact and remained associated with the Texas Red fluorophore after PA pore translocation. FIG. 6 demonstrates that PA and LFn-PKR can be used to load liposomes/exosomes with siRNA and that these liposomes/exosomes can be isolated by either the exoEasy kit or by differential centrifugation. It also shows that the liposomes/exosomes were active, recipient cell fusion competent, and capable of delivering pharmacologically active siRNA. This was proof of concept, i.e. the described exosome loading methodology can be used to load and deliver cargo into liposomes/exosomes and that the liposomes/exosomes can be isolated and used to transfer biologically active cargo from one population of cells to another. This would support the idea that this methodology could be used to load drugs into an exosome derived from a patient's cells grown ex vivo in order to facilitate the third order targeting and stealth delivery of personalised, precision medicine such as siRNA, gene editing proteins and gRNA, shRNA, miRNA, genes and therapeutic proteins.

In an attempt to optimise the loading of material into liposomes/exosomes, both PA63 (produced as PA63-TEV recognition site-GST), PA83, PA83 $D^{512}K$, PA83 G to N and PA83 N to S [16] were also investigated for their capacity to load liposomes/exosomes. Finally, a PA83 hybrid molecule incorporating the trans-membrane domain of haemolysin [17] replacing the PA63 trans-membrane domain was encoded into a bacterial expression cassette (pET151), also constructed to investigate the roll of the PA83 trans-membrane assembly in regard to the rate limits associated with the phenomena of Brownian ratchetting [6] during cargo pore transit.

Example 9

The inventors loaded exosomes with the conditionally lethal cargo LFn-Diphtheria toxin A chain (DTA) using PA83 as described above, with the exception of the plasmid used, i.e. the plasmid was from Addgene (pET-15b LFn-DTA, Addgene number 11075) (https://www.addgene.org/11075/)

Loading Exosomes

The exosomes were loaded by incubating LFnDTA—SEQ ID No: 15 (protein) and SEQ ID No: 16 (DNA)—with HeLa cells at a concentration of 10 µg/ml and 50 µg/ml of SEQ ID No. 2 (PA83) for 4 hours at 37° C. in humidified atmosphere containing 5% (v/v) $CO_2$. After this time the cells were washed with PBS and incubated with 5 µM Ionomycin (Sigma chemical company catalogue number I9657-1MG) in serum free media. Exosomes were then isolated from the now conditioned media using differential centrifugation as previously described.

Trypsin Digestion

To half of the exosome preparation, 5 µl of cell culture trypsin/EDTA (TE) buffer (ThermoFisher Scientific catalogue number 25200056) was added to the exosomes and the volume adjusted to 100 µl with PBS. To the other half of the preparation, PBS was added to 100 µl. The exosome preparations were then incubated for 60 min under conditions that had already been demonstrated to be sufficient to digest 5 µg of LFnDTA, vastly in excess of the amount of LFnDTA contained within the exosome preparation. The exosomes were then added to a culture of HeLa cells with a trypsin control (found to be non-toxic) and cell viability assayed after 24 h. Results were expressed as DTA activity (%) normalized to the untreated control (LFnDTA containing exosomes killed about 45% of the cells).

Results

Figure 8:
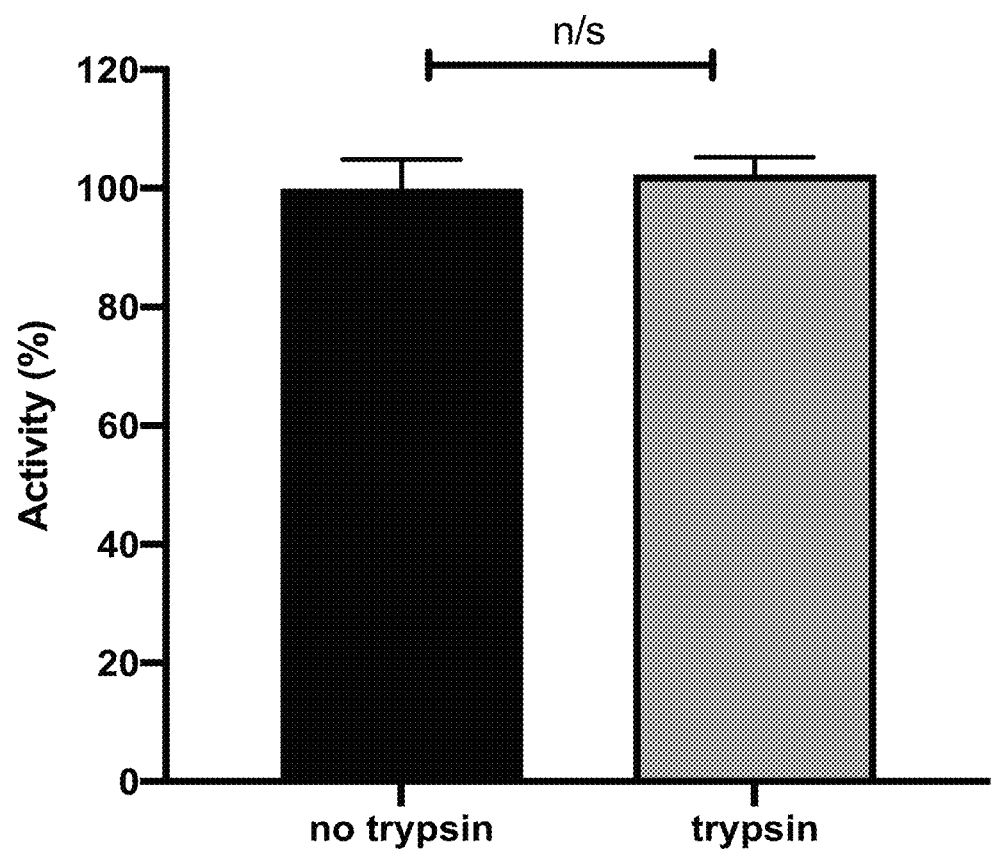
FIG. 8 shows the activity of exosomes loaded with LFn-diphtheria toxin A chain (DTA) after incubation for 60 min at 37° C. with excess trypsin (n=3±SEM) prior to incubation with HeLa cells. Cell viability was approximately 55% of an untreated control in both instances.

Referring to FIG. 8, exosomes initially loaded with the cargo (i.e. LFn-diphtheria toxin A chain (DTA)—SEQ ID No: 15 and 16) using PA83 (i.e. SEQ ID No:2) were subsequently characterised to show that they were protected from the activity of external enzymes (i.e. trypsin). These data show that the exosomes can be successfully loaded with LFnDTA, which could be used for treating cancer, such as cervical carcinoma.

Example 10

In this Example, the inventors used dynamic light scattering AKA photon correlation spectroscopy to characterize the size of exosomes and extracellular vesicles (EVs) isolated using differential centrifugation.

Loading Exosomes

Exosomes from HeLa cells were loaded with prehybridized phosphorothioate-phosphodiester hybrid antisense oligonucleotides (ASOs) specific for tandem dimeric tomato at a concentration of 200 pMol/ml (total ASO)—SEQ ID No: 17 and 18. The following table explains the phosphorothioate codes (taken from Thermofisher website).

media removed and the cells washed with PBS prior to being incubated with 5 µM ionomycin in serum free media for 30 min.

Exosome Isolation

The conditioned media was first cleared by centrifugation at 1.5 k×g for 2 min and filtered through a 0.8 micron filter. The flow through was subject to centrifugation at 10 000×g for 30 min at 4° C. Finally exosomes were isolated by sedimentation at 110 000×g for 70 min at 4° C., resuspended in PBS and then re-sedimented at 110,000×g for 70 min at 4° C. Exosomes were stored at 4° C. until then were used. When used for cell culture the exosomes were diluted in the desired amount of serum free media and again filtered through a 0.8µ filter prior to incubation with cells.

Results

Figure 9:
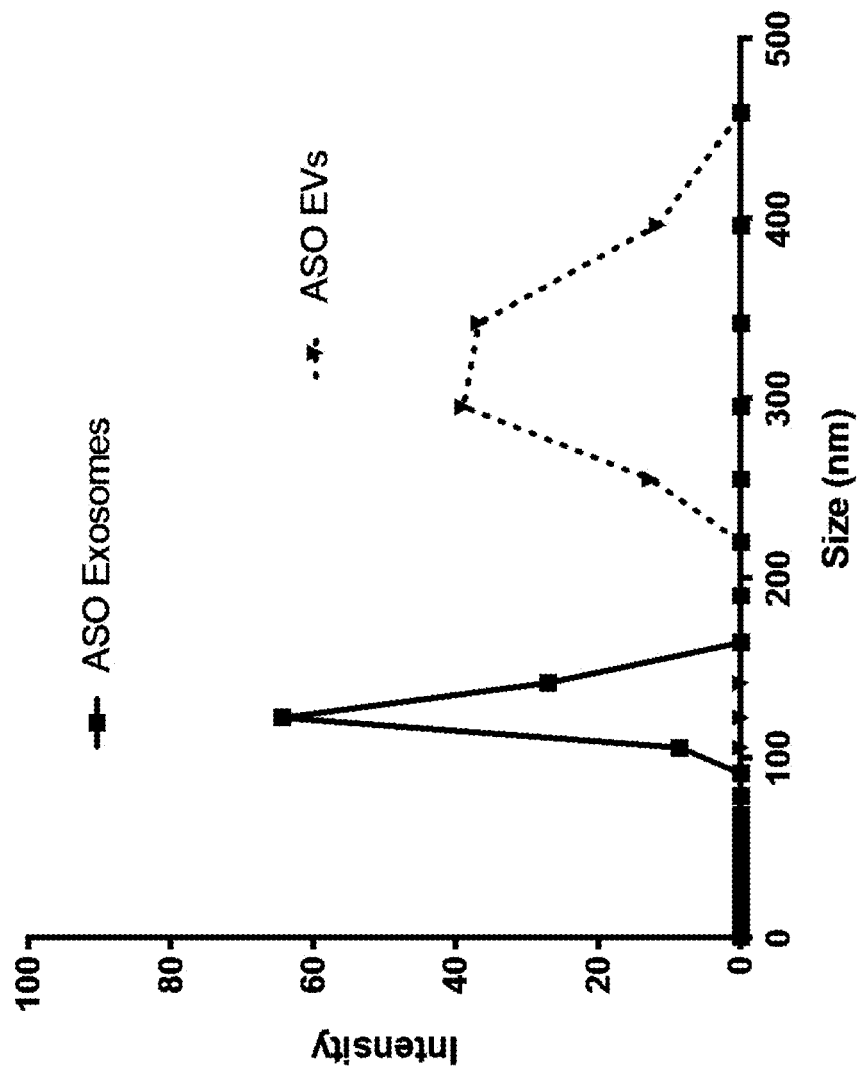
FIG. 9 shows the photon correlation spectroscopic analysis of HeLA exosome and extracellular vesicle fractions loaded with wild type PA83, LFnPKR and anti-TdTom antisense oligonucleotides (ASOs)

Referring to FIG. 9, exosomes were shown to have the predicted size when loaded with 200 pMol/ml anti-tandem dimeric tomato (TdTom) antisense oligonucleotides (ASOs) using 50 µg/ml PA83 (SEQ ID No:2) and 50 µg/ml LFnPKR (SEQ ID No:13).

Figure 10:
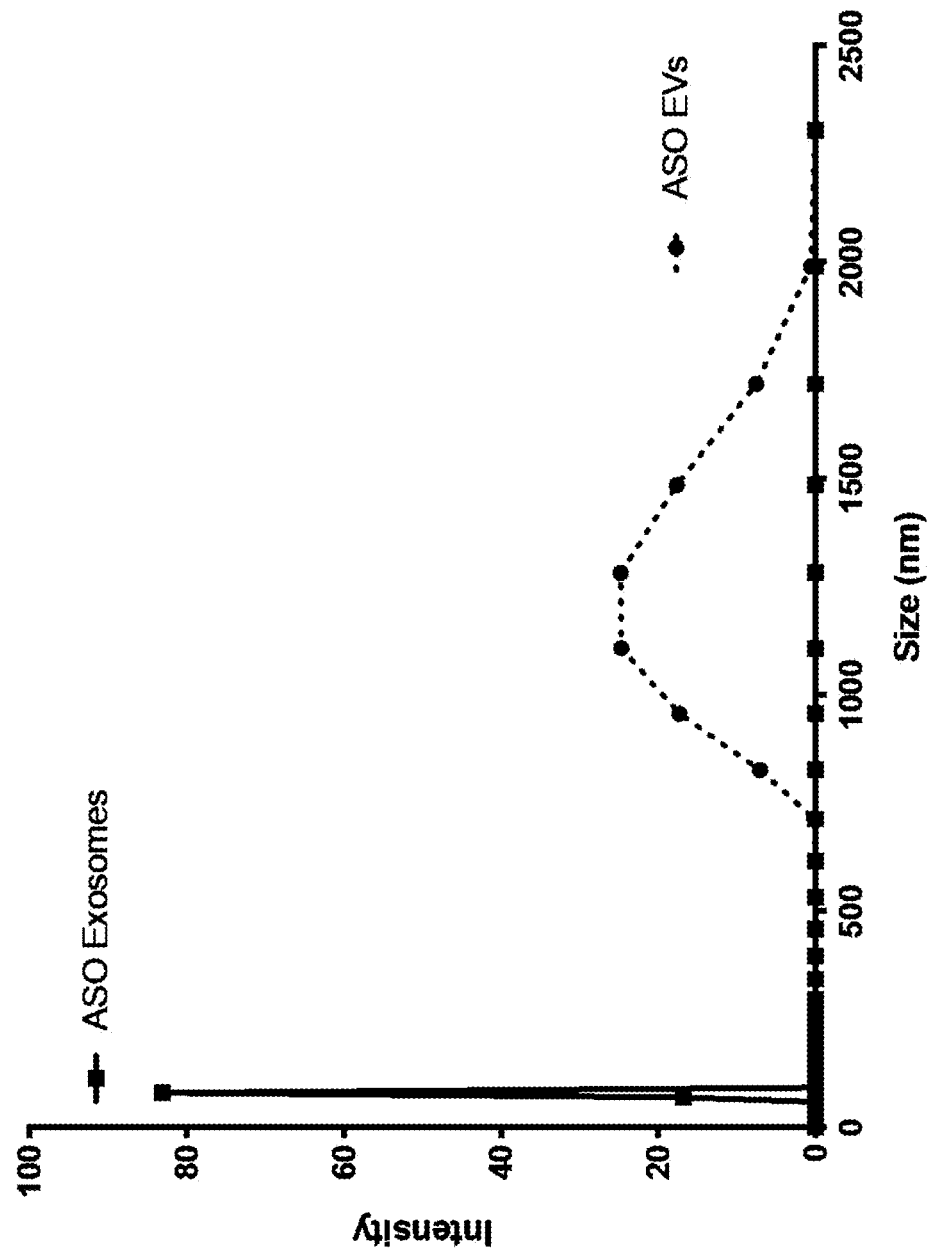
FIG. 10 shows the photon correlation spectroscopic analysis of HeLA exosome and extracellular vesicle fractions loaded with forced octamer PA83 mutants, LFnPKR and anti-TdTom antisense oligonucleotides (ASOs)

Referring to FIG. 10, exosomes were also shown to have the predicted size when loaded with 200 pMol/ml anti-TdTom ASOs using forced octamer PA83 mutants, i.e. 25 µg/ml PA83$D^{512}K$ (SEQ ID No:7) and 25 µg/ml PA83 K245G; R252N (SEQ ID No:8) with 50 µg/ml LFnPKR (SEQ ID No:13). These data demonstrate that the membrane fractions that are generated are of the predicted size for exosomes and EVs.

Example 11

The inventors tested if exosomes loaded with active ASOs retain their pharmacological activity.

Loading Exosomes

Exosomes were loaded by incubating HeLa cells with 200 pMol/ml anti-TdTom ASOs (SEQ ID No: 17 and 18) and either 50 µg/ml heptameric (PA83—SEQ ID No:2), or forced octamer PA83 mutants (i.e. 25 µg/ml—SEQ ID No: 7, (PA83 $D^{512}K$) and 25 µg/ml SEQ ID No: 8, (PA83 $K^{245}G$; $R^{252}N$)) and 50 µg/ml SEQ ID No: 13 (LFnPKR). After Isolation, these ASO loaded exosomes demonstrated antisense activity against an mRNA target encoding GFP fused beta-galactosidase and bicistronically expressing tandem dimeric tomato overexpressed in HEK293 cells (Catalogue number SC008 from ASMBIO) HEK cells (~1×10$^6$ per well) were treated with: 57 µg [total protein measured at $OD_{280}$] of the heptamer::ASO exosome prep or 42 µg [total protein measured at $OD_{280}$] of the octamer::ASO.

Results

Figure 11:
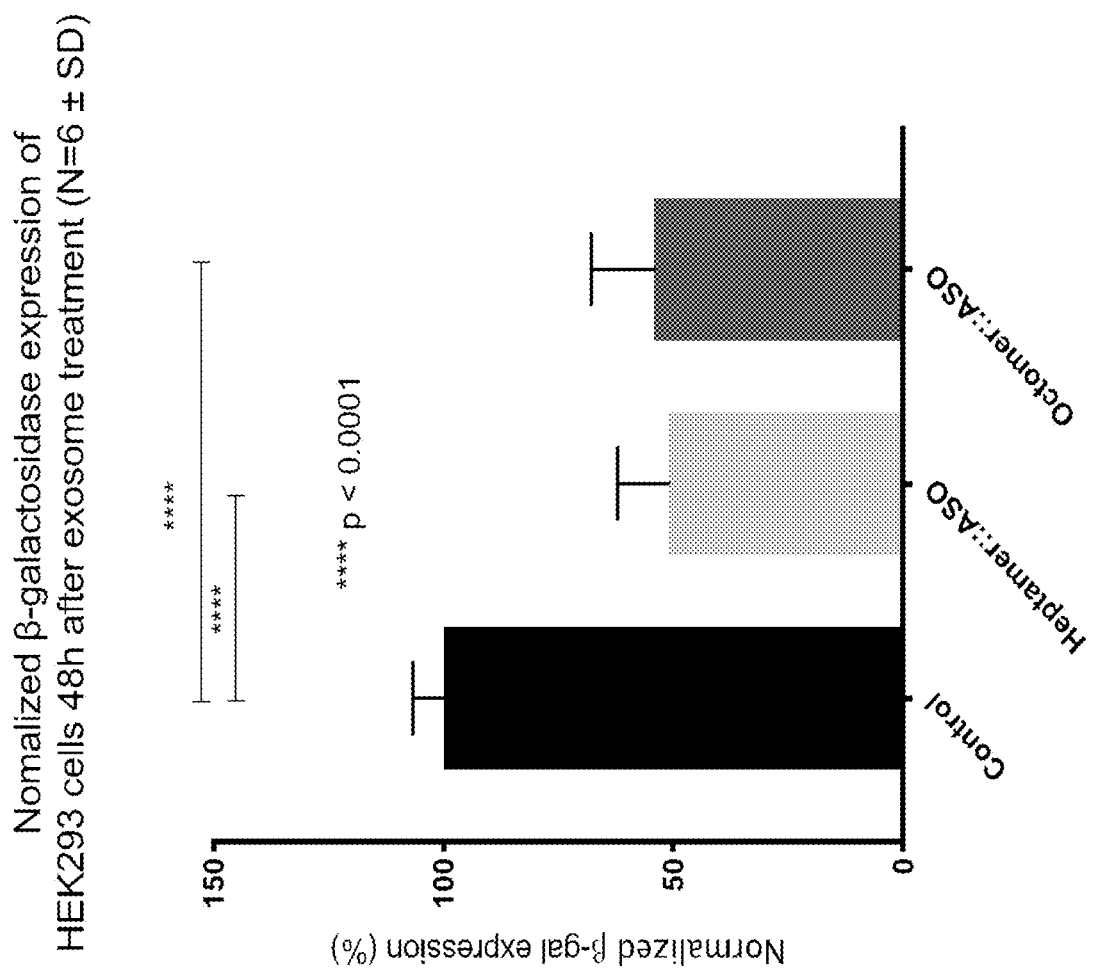
FIG. 11 shows normalized β-galactosidase expression of HEK293 cells 48 hours after exosome treatment.

Referring to FIG. 11, the exosomes loaded with ASOs are shown to have pharmacological activity. These data dem-

| Phosphorothioates | See below | A sulphur is substituted for one of the oxygens in the phosphodiester bonds between the nucleotides. This linkage is to the 3' side of the designated base. |
|---|---|---|
| A-Phosphorothioate | F | |
| C-Phosphorothioate | O | |
| G-Phosphorothioate | E | |
| T-Phosphorothioate | Z | |

These ASOs were loaded into exosomes using 50 µg/ml LFnPKR and 50 µg/ml SEQ ID No: 2, (PA83) or 50 µg/ml PA forced octamer mutants. This mixture was incubated with the HeLa cells in serum free media for 4 hours at 37° C. in a humidified atmosphere containing 5% (v/v) $CO_2$. The onstrates that the methodology can be used to load ASOs into exosomes, and that the exosomes: (i) are fusion competent; (ii) contain ASOs; (iii) the ASOs are active; and (iv) the exosomes can be used to deliver ASOs. These data also show that variants of PA can be used to load exosomes.

Example 12

Exosomes were loaded using 50 nM stealth reporter anti-GFP siRNA (Invitrogen catalogue number 12935-145), 50 µg/ml PA83 (SEQ ID No: 2) and 50 µg/ml LFnPKR (SEQ ID No: 13) resuspended in serum free media. Exosomes were isolated as before i.e. after a 4 hour incubation with the protein::siRNA mixture and a 30 min incubation with 5 µM Ionomycin in serum free media. All incubations were carried out at 37° C. and the cells were washed with PBS between incubations as before. Exosomes were isolated using the exoEasy kit from Qiagen (catalogue number 76064). Exosomes were washed in PBS and sedimented as before (i.e. 110 000×g for 70 min at 4° C.) prior to being resuspended in 500 µl of PBS. Exosomes were diluted using complete media and added to HEK293 cells stably expressing GFP fused beta-galactosidase and tandem dimeric tomato (Catalogue number SC008 from ASMBIO). Beta-galactosidase activity in cell lysate was then assayed by measuring X-gal conversion at $OD_{620}$ over time and normalising conversion to total cell lysate protein concentration.

Figure 12:
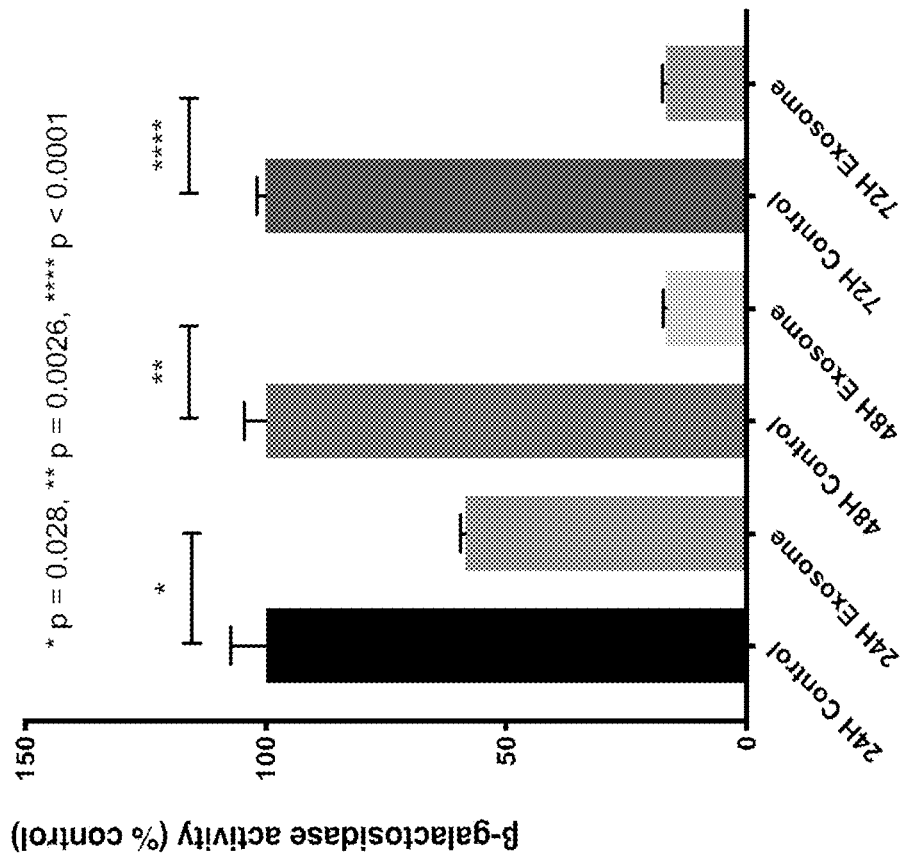
FIG. 12 shows β-galactosidase activity after transfection of HEK293 cells with HeLa exosomes loaded with α-GFP siRNA and isolated using the ExoEasy Kit. Feeder cells treated with PA:LF nPKR::50 nM si RNA overtime.

Referring to FIG. 12, it can be seen that anti-GFP siRNA loaded into HeLa derived exosomes using PA83 and LFnPKR have pharmacological activity. These data demonstrate that, as with the ASOs of Example 11, siRNA retains its activity in the exosomes.

Summary

Advantages of the aspects and embodiments of the liposomes described herein reside in seeking to address one or more problems inherent in the prior art by sequestering ILVs loaded with Atx associated cargo as liposomes (e.g. exosomes) prior to ILV back-fusion. In addition, the use of membrane spanning sequences that perform the same function as Atx PA63 but contain recombinant trans-membrane sequence is also addressed.

Liposomes/exosomes can shield intraluminal content from enzymatic destruction and the immune response and are often referred to as a naturally occurring, paracrine transport system that protects antigenic or enzymatically labile material in transit. Given that wild type LF has been documented within both ILVs and liposomes (e.g. exosomes), and it is known that ILVs can be secreted from cells as liposomes (e.g. exosomes) after the release of ER stored calcium [5], it has been reasoned by the inventors that recombinant LF could also be trapped or loaded into liposomes (e.g. exosomes). Further, the use of an ionophore (e.g. ionomycin) results in the release of ER calcium on demand, triggering the exocytosis of ILVs, as liposomes (e.g. exosomes). Consequently, ionomycin was used to temporally capture ILVs containing cargo, from cells that were previously treated with the Atx derived delivery system. This then allowed for the isolation of cargo loaded exosomes secreted into the cell culture media. Although Atx components protective antigen (PA) 83 or PA63, lethal factor (LF) and oedema factor (EF) have been reported to localise to liposomes/exosomes [4], the loading of associated molecules (i.e. LFn-GAL4, LFn-PKR, LFn-PKR-Texas Red, siRNA, CAS9 or Cas9-Texas Red) within liposomes/exosomes using pore-forming recombinant proteins has not been previously reported.

REFERENCES

[1] Tyagi P., Subramony J. A. (2018) Nanotherapeutics in oral and parenteral drug delivery: Key learnings and future outlooks as we think small. J. Control Release. 272:159-168.

[2] S. C. Richardson, S. C. Winistorfer, V. Poupon, J. P. Luzio, R. C. Piper. (2004) Mammalian late vacuole protein sorting orthologues participate in early endosomal fusion and interact with the cytoskeleton, Mol Biol Cell. 15, 1197-1210.

[3] Abrami, L., Lindsay, M., Parton, R. G., Leppla, S. H., & van der Goot, F. G. (2004). Membrane insertion of anthrax protective antigen and cytoplasmic delivery of lethal factor occur at different stages of the endocytic pathway. The Journal of Cell Biology, 166(5), 645-651.

[4] Abrami, L., Brandi, L., Moayeri, M., Brown, M. J., Krantz, B. A., Leppla, S. H., & van der Goot, F. G. (2013). Hijacking Multivesicular Bodies Enables Long-Term and Exosome-Mediated Long-Distance Action of Anthrax Toxin, 5(4), 986-996.

[5] Kuznetsov G., Brostrom M. A., and Brostrom C. (1992) Demonstration of a Calcium Requirement for Secretory Protein Processing and Export. The Journal of Biological Chemistry. 267(6); 3932-3939.

[6] Blaustein, R. O., Koehler, T. M., Collier, R. J., and Finkelstein, A. Proc. Natl. Acad. Sci. USA 86, 2209-2213 (1989).

[7] B. A. Krantz, et al., Acid-induced unfolding of the amino-terminal domains of the lethal and edema factors of anthrax toxin, J. Mol. Biol. 344 (3) (2004) 739-756.

[8] Auger A., Park M., Nitschke F., Minassian L. M., Beilhartz G. L., Minassian B. A., and Melnyk R. A. (2105) Efficient Delivery of Structurally Diverse Protein Cargo into Mammalian Cells by a Bacterial Toxin. Mol. Pharmaceutics, 12 (8), pp 2962-2971

[9] Dyer P. D. (2013) Development of a Protein-Based Antisense Delivery Platform Modelled on Anthrax Toxin. PhD Thesis, University of Greenwich.

[10] Gaur, R., Gupta, P., Goyal, A., Wels, W. & Singh, Y. Delivery of nucleic acid into mammalian cells by anthrax toxin. Biochem. Biophys. Res. Commun. 297, 1121-1127 (2002).

[11] Baillie, L W., Huwar, T. B., Moore, S., Mellado-Sanchez, G., Rodriguez, L., Neeson, B. N., et al. (2010). An anthrax subunit vaccine candidate based on protective regions of Bacillus anthracis protective antigen and lethal factor. Vaccine, 28(41), 6740-6748.

[12] Khandia R., Bhatia S., Chanu K. V., Sood R. and Dhama K. (2014). Anthrax Toxin Receptors, Functions and their Possible Use in Therapeutics: A Review. Asian Journal of Animal and Veterinary Advances, 9: 599-609.

[13] Guo S. & Huang L. (2011) Nanoparticles Escaping RES and Endosome: Challenges for siRNA Delivery for Cancer Therapy. Journal of Nanomaterials. Article ID 742895. DoI: 10.1155/2011/742895

[14] S. C. Richardson, S. C. Winistorfer, V. Poupon, J. P. Luzio, R. C. Piper. Mammalian late vacuole protein sorting orthologues participate in early endosomal fusion and interact with the cytoskeleton, Mol Biol Cell. (2004) 15, 1197-1210.

[15] Willms E., Johansson H. J., Mager I., Lee Y., et al., (2015) Cells Release Subpopulations of Exosomes with Distinct Molecular and Biological Properties. Scientific Reports 6: 22519.

[16] Phillips D. D., Fattah R. J., Crown D., et al. (2013) Engineering Anthrax Toxin Variants That Exclusively Form Octamers and Their Application to Targeting Tumors. J. Biol. Chem., 288: 9058-9065.

[17] Karginov, V. A., Nestorovich E. M., Schmidtmann, F. Robinson T. M., Yohannes, A., Fahmi N. E., Bezrukov S. M., and Hecht S. M. (2007) Inhibition of S. aureus α-Hemolysin and B. anthracis Lethal Toxin by β-Cyclo-dextrin Derivatives. Bioorg Med Chem.; 15(16): 5424-5431.

[18] Feld G. K., Brown, M. J. & Krantz B. A. (2012) Ratcheting up protein translocation with anthrax toxin. PROTEIN SCIENCE. 21:606-624.

The invention claimed is:

1. A method of preparing a liposome, the method comprising contacting at least one cell with: (i) a pore-forming protein, or a pore-forming domain or a variant or fragment thereof; and (ii) a shuttle protein attached to a bioactive payload molecule, wherein the pore-forming protein, or the pore-forming domain or the variant or fragment thereof creates a pore through a phospholipid bilayer of the at least one cell, and the shuttle protein interacts with the pore-forming protein, or the pore-forming domain or the variant or fragment thereof, and is internalised into the cell to thereby produce a liposome loaded with a bioactive payload molecule, wherein the method further comprises isolating the liposome from the cell.

2. The method according to claim 1, wherein the liposome comprises a vesicle, wherein said vesicle is selected from the group comprising a vesicle, an extracellular vesicle (EV), an intracellular vesicle, an intraluminal vesicle (ILV), and an exosome, optionally wherein said liposome has an average diameter of between 10 nm and 500 nm.

3. The method according to claim 1, wherein said cell comprises a mammalian or human cell.

4. The method according to claim 1, wherein the pore-forming protein, or the pore-forming domain or the variant or fragment thereof comprises, or is derived from, a non-toxic protein, optionally wherein said pore-forming protein, pore-forming domain or the variant or fragment thereof is derived from the group consisting of *B. anthracis*, *B. anthracis* virulence factor Protective Antigen (PA), *B. anthracis* PA83 and *B. anthracis* PA63.

5. The method according to claim 1, wherein the pore-forming protein, or the pore-forming domain or the variant or fragment thereof, comprises or consists of an amino acid sequence substantially as set out in any one of SEQ ID No: 1, 2, 5-10, or a variant or fragment thereof.

6. The method according to claim 1, wherein the shuttle protein is configured to facilitate transport of said bioactive payload molecule, through the pore of the pore-forming protein, and wherein the shuttle protein comprises an attenuated toxin protein.

7. The method according claim 6, wherein the shuttle protein comprises a linker protein, and/or wherein, in the attenuated toxin, at least one toxin domain, optionally one or more of toxic domains II-IV of the *B. anthracis* lethal factor protein toxin, is replaced by the linker protein, and optionally wherein the linker protein comprises a nucleic-acid-binding domain, optionally wherein said nucleic-acid-binding domain is *Saccharomyces cerevisiae* GAL4.

8. The method according to claim 6, wherein the attenuated toxin protein is selected from the group consisting of *B. anthracis* derived lethal factor (LF) and oedema factor (EF).

9. The method according to claim 1, wherein the shuttle protein comprises an amino acid sequence substantially as set out in SEQ ID No: 11, or a variant or fragment thereof.

10. The method according to claim 1, wherein the shuttle protein comprises an amino acid sequence selected from the group of amino acid sequences set forth in SEQ ID No: 12, SEQ ID NO: 13, a variant thereof, and a fragment thereof.

11. The method according to claim 1, wherein the bioactive molecule comprises an amino acid sequence substantially as set out in SEQ ID No: 14, or a variant or fragment thereof.

12. The method according to claim 1, wherein (a) the bioactive payload molecule is a therapeutically active molecule which is active within the cell cytosol, within the nucleus, within an organelle or intracellular structure, or within a cell surface lipid membrane or an intracellular lipid membrane; (b) wherein the molecular weight of the bioactive compound is between 1 Da and 10 MDa; and (c) the bioactive molecule is: (i) a small molecule, a protein, a nucleotide, DNA or a DNA construct, plasmid, RNA or an RNA construct, mRNA, miRNA, a guide RNA, snRNA, siRNA, antisense oligonucleotide (ASO), or (ii) a large molecule.

13. The method according to claim 12, wherein the intracellular structure is a vesicle or vacuole.

14. The method according to claim 12, wherein the large molecule is selected from the group consisting of a protein or enzyme or a fragment thereof, a nuclease, and an antibody or antigen-binding fragment thereof.

15. The method according to claim 12, wherein the bioactive payload molecule comprises a genome editing tool.

16. The method according to claim 15, wherein the genome editing tool is a nuclease selected from the group consisting of Cas9, Cpf1, a TALEN, and a zinc finger nuclease.

* * * * *

SEQUENCE LISTING

<160> NUMBER OF SEQ ID NOS: 18

<210> SEQ ID NO 1
<211> LENGTH: 747
<212> TYPE: PRT
<213> ORGANISM: Bacillus anthracis

<400> SEQUENCE: 1

```
Met Arg Gly Ser His His His His His His Gly Ser Glu Val Lys Gln
1               5                   10                  15

Glu Asn Arg Leu Leu Asn Glu Ser Glu Ser Ser Ser Gln Gly Leu Leu
            20                  25                  30

Gly Tyr Tyr Phe Ser Asp Leu Asn Phe Gln Ala Pro Met Val Val Thr
        35                  40                  45

Ser Ser Thr Thr Gly Asp Leu Ser Ile Pro Ser Ser Glu Leu Glu Asn
    50                  55                  60

Ile Pro Ser Glu Asn Gln Tyr Phe Gln Ser Ala Ile Trp Ser Gly Phe
65                  70                  75                  80

Ile Lys Val Lys Lys Ser Asp Glu Tyr Thr Phe Ala Thr Ser Ala Asp
                85                  90                  95

Asn His Val Thr Met Trp Val Asp Asp Gln Glu Val Ile Asn Lys Ala
            100                 105                 110

Ser Asn Ser Asn Lys Ile Arg Leu Glu Lys Gly Arg Leu Tyr Gln Ile
        115                 120                 125

Lys Ile Gln Tyr Gln Arg Glu Asn Pro Thr Glu Lys Gly Leu Asp Phe
    130                 135                 140

Lys Leu Tyr Trp Thr Asp Ser Gln Asn Lys Lys Glu Val Ile Ser Ser
145                 150                 155                 160

Asp Asn Leu Gln Leu Pro Glu Leu Lys Gln Lys Ser Ser Asn Ser Arg
                165                 170                 175

Lys Lys Arg Ser Thr Ser Ala Gly Pro Thr Val Pro Asp Arg Asp Asn
            180                 185                 190

Asp Gly Ile Pro Asp Ser Leu Glu Val Glu Gly Tyr Thr Val Asp Val
        195                 200                 205

Lys Asn Lys Arg Thr Phe Leu Ser Pro Trp Ile Ser Asn Ile His Glu
    210                 215                 220

Lys Lys Gly Leu Thr Lys Tyr Lys Ser Ser Pro Glu Lys Trp Ser Thr
225                 230                 235                 240

Ala Ser Asp Pro Tyr Ser Asp Phe Glu Lys Val Thr Gly Arg Ile Asp
                245                 250                 255

Lys Asn Val Ser Pro Glu Ala Arg His Pro Leu Val Ala Ala Tyr Pro
            260                 265                 270

Ile Val His Val Asp Met Glu Asn Ile Ile Leu Ser Lys Asn Glu Asp
        275                 280                 285

Gln Ser Thr Gln Asn Thr Asp Ser Gln Thr Arg Thr Ile Ser Lys Asn
    290                 295                 300

Thr Ser Thr Ser Arg Thr His Thr Ser Glu Val His Gly Asn Ala Glu
305                 310                 315                 320

Val His Ala Ser Phe Phe Asp Ile Gly Gly Ser Val Ser Ala Gly Phe
                325                 330                 335

Ser Asn Ser Asn Ser Ser Thr Val Ala Ile Asp His Ser Leu Ser Leu
            340                 345                 350

Ala Gly Glu Arg Thr Trp Ala Glu Thr Met Gly Leu Asn Thr Ala Asp
        355                 360                 365
```

```
Thr Ala Arg Leu Asn Ala Asn Ile Arg Tyr Val Asn Thr Gly Thr Ala
        370                 375                 380
Pro Ile Tyr Asn Val Leu Pro Thr Thr Ser Leu Val Leu Gly Lys Asn
385                 390                 395                 400
Gln Thr Leu Ala Thr Ile Lys Ala Lys Glu Asn Gln Leu Ser Gln Ile
                405                 410                 415
Leu Ala Pro Asn Asn Tyr Tyr Pro Ser Lys Asn Leu Ala Pro Ile Ala
            420                 425                 430
Leu Asn Ala Gln Asp Asp Phe Ser Ser Thr Pro Ile Thr Met Asn Tyr
        435                 440                 445
Asn Gln Phe Leu Glu Leu Glu Lys Thr Lys Gln Leu Arg Leu Asp Thr
    450                 455                 460
Asp Gln Val Tyr Gly Asn Ile Ala Thr Tyr Asn Phe Glu Asn Gly Arg
465                 470                 475                 480
Val Arg Val Asp Thr Gly Ser Asn Trp Ser Glu Val Leu Pro Gln Ile
                485                 490                 495
Gln Glu Thr Thr Ala Arg Ile Ile Phe Asn Gly Lys Asp Leu Asn Leu
            500                 505                 510
Val Glu Arg Arg Ile Ala Ala Val Asn Pro Ser Asp Pro Leu Glu Thr
        515                 520                 525
Thr Lys Pro Asp Met Thr Leu Lys Glu Ala Leu Lys Ile Ala Phe Gly
    530                 535                 540
Phe Asn Glu Pro Asn Gly Asn Leu Gln Tyr Gln Gly Lys Asp Ile Thr
545                 550                 555                 560
Glu Phe Asp Phe Asn Phe Asp Gln Gln Thr Ser Gln Asn Ile Lys Asn
                565                 570                 575
Gln Leu Ala Glu Leu Asn Ala Thr Asn Ile Tyr Thr Val Leu Asp Lys
            580                 585                 590
Ile Lys Leu Asn Ala Lys Met Asn Ile Leu Ile Arg Asp Lys Arg Phe
        595                 600                 605
His Tyr Asp Arg Asn Asn Ile Ala Val Gly Ala Asp Glu Ser Val Val
    610                 615                 620
Lys Glu Ala His Arg Glu Val Ile Asn Ser Ser Thr Glu Gly Leu Leu
625                 630                 635                 640
Leu Asn Ile Asp Lys Asp Ile Arg Lys Ile Leu Ser Gly Tyr Ile Val
                645                 650                 655
Glu Ile Glu Asp Thr Glu Gly Leu Lys Glu Val Ile Asn Asp Arg Tyr
            660                 665                 670
Asp Met Leu Asn Ile Ser Ser Leu Arg Gln Asp Gly Lys Thr Phe Ile
        675                 680                 685
Asp Phe Lys Lys Tyr Asn Asp Lys Leu Pro Leu Tyr Ile Ser Asn Pro
    690                 695                 700
Asn Tyr Lys Val Asn Val Tyr Ala Val Thr Lys Glu Asn Thr Ile Ile
705                 710                 715                 720
Asn Pro Ser Glu Asn Gly Asp Thr Ser Thr Asn Gly Ile Lys Lys Ile
                725                 730                 735
Leu Ile Phe Ser Lys Lys Gly Tyr Glu Ile Gly
            740                 745

<210> SEQ ID NO 2
<211> LENGTH: 747
<212> TYPE: PRT
<213> ORGANISM: Artificial Sequence
<220> FEATURE:
<223> OTHER INFORMATION: MRSG-6His-PA83
```

<400> SEQUENCE: 2

```
Met Arg Gly Ser His His His His His His Gly Ser Glu Val Lys Gln
1               5                   10                  15

Glu Asn Arg Leu Leu Asn Glu Ser Glu Ser Ser Gln Gly Leu Leu
            20                  25                  30

Gly Tyr Tyr Phe Ser Asp Leu Asn Phe Gln Ala Pro Met Val Val Thr
                35                  40                  45

Ser Ser Thr Thr Gly Asp Leu Ser Ile Pro Ser Ser Glu Leu Glu Asn
    50                  55                  60

Ile Pro Ser Glu Asn Gln Tyr Phe Gln Ser Ala Ile Trp Ser Gly Phe
65                  70                  75                  80

Ile Lys Val Lys Lys Ser Asp Glu Tyr Thr Phe Ala Thr Ser Ala Asp
                85                  90                  95

Asn His Val Thr Met Trp Val Asp Asp Gln Glu Val Ile Asn Lys Ala
                100                 105                 110

Ser Asn Ser Asn Lys Ile Arg Leu Glu Lys Gly Arg Leu Tyr Gln Ile
            115                 120                 125

Lys Ile Gln Tyr Gln Arg Glu Asn Pro Thr Glu Lys Gly Leu Asp Phe
130                 135                 140

Lys Leu Tyr Trp Thr Asp Ser Gln Asn Lys Lys Glu Val Ile Ser Ser
145                 150                 155                 160

Asp Asn Leu Gln Leu Pro Glu Leu Lys Gln Lys Ser Ser Asn Ser Arg
                165                 170                 175

Lys Lys Arg Ser Thr Ser Ala Gly Pro Thr Val Pro Asp Arg Asp Asn
            180                 185                 190

Asp Gly Ile Pro Asp Ser Leu Glu Val Glu Gly Tyr Thr Val Asp Val
        195                 200                 205

Lys Asn Lys Arg Thr Phe Leu Ser Pro Trp Ile Ser Asn Ile His Glu
210                 215                 220

Lys Lys Gly Leu Thr Lys Tyr Lys Ser Ser Pro Glu Lys Trp Ser Thr
225                 230                 235                 240

Ala Ser Asp Pro Tyr Ser Asp Phe Glu Lys Val Thr Gly Arg Ile Asp
                245                 250                 255

Lys Asn Val Ser Pro Glu Ala Arg His Pro Leu Val Ala Ala Tyr Pro
            260                 265                 270

Ile Val His Val Asp Met Glu Asn Ile Ile Leu Ser Lys Asn Glu Asp
        275                 280                 285

Gln Ser Thr Gln Asn Thr Asp Ser Gln Thr Arg Thr Ile Ser Lys Asn
    290                 295                 300

Thr Ser Thr Ser Arg Thr His Thr Ser Glu Val His Gly Asn Ala Glu
305                 310                 315                 320

Val His Ala Ser Phe Phe Asp Ile Gly Gly Ser Val Ser Ala Gly Phe
                325                 330                 335

Ser Asn Ser Asn Ser Ser Thr Val Ala Ile Asp His Ser Leu Ser Leu
            340                 345                 350

Ala Gly Glu Arg Thr Trp Ala Glu Thr Met Gly Leu Asn Thr Ala Asp
        355                 360                 365

Thr Ala Arg Leu Asn Ala Asn Ile Arg Tyr Val Asn Thr Gly Thr Ala
    370                 375                 380

Pro Ile Tyr Asn Val Leu Pro Thr Thr Ser Leu Val Leu Gly Lys Asn
385                 390                 395                 400

Gln Thr Leu Ala Thr Ile Lys Ala Lys Glu Asn Gln Leu Ser Gln Ile
```

```
                405                 410                 415
Leu Ala Pro Asn Asn Tyr Tyr Pro Ser Lys Asn Leu Ala Pro Ile Ala
            420                 425                 430
Leu Asn Ala Gln Asp Asp Phe Ser Thr Pro Ile Thr Met Asn Tyr
        435                 440                 445
Asn Gln Phe Leu Glu Leu Glu Lys Thr Lys Gln Leu Arg Leu Asp Thr
    450                 455                 460
Asp Gln Val Tyr Gly Asn Ile Ala Thr Tyr Asn Phe Glu Asn Gly Arg
465                 470                 475                 480
Val Arg Val Asp Thr Gly Ser Asn Trp Ser Glu Val Leu Pro Gln Ile
                485                 490                 495
Gln Glu Thr Thr Ala Arg Ile Ile Phe Asn Gly Lys Asp Leu Asn Leu
            500                 505                 510
Val Glu Arg Arg Ile Ala Ala Val Asn Pro Ser Asp Pro Leu Glu Thr
        515                 520                 525
Thr Lys Pro Asp Met Thr Leu Lys Glu Ala Leu Lys Ile Ala Phe Gly
    530                 535                 540
Phe Asn Glu Pro Asn Gly Asn Leu Gln Tyr Gln Gly Lys Asp Ile Thr
545                 550                 555                 560
Glu Phe Asp Phe Asn Phe Asp Gln Gln Thr Ser Gln Asn Ile Lys Asn
                565                 570                 575
Gln Leu Ala Glu Leu Asn Ala Thr Asn Ile Tyr Thr Val Leu Asp Lys
            580                 585                 590
Ile Lys Leu Asn Ala Lys Met Asn Ile Leu Ile Arg Asp Lys Arg Phe
        595                 600                 605
His Tyr Asp Arg Asn Asn Ile Ala Val Gly Ala Asp Glu Ser Val Val
    610                 615                 620
Lys Glu Ala His Arg Glu Val Ile Asn Ser Ser Thr Glu Gly Leu Leu
625                 630                 635                 640
Leu Asn Ile Asp Lys Asp Ile Arg Lys Ile Leu Ser Gly Tyr Ile Val
                645                 650                 655
Glu Ile Glu Asp Thr Glu Gly Leu Lys Glu Val Ile Asn Asp Arg Tyr
            660                 665                 670
Asp Met Leu Asn Ile Ser Ser Leu Arg Gln Asp Gly Lys Thr Phe Ile
        675                 680                 685
Asp Phe Lys Lys Tyr Asn Asp Lys Leu Pro Leu Tyr Ile Ser Asn Pro
    690                 695                 700
Asn Tyr Lys Val Asn Val Tyr Ala Val Thr Lys Glu Asn Thr Ile Ile
705                 710                 715                 720
Asn Pro Ser Glu Asn Gly Asp Thr Ser Thr Asn Gly Ile Lys Lys Ile
                725                 730                 735
Leu Ile Phe Ser Lys Lys Gly Tyr Glu Ile Gly
            740                 745

<210> SEQ ID NO 3
<211> LENGTH: 10
<212> TYPE: PRT
<213> ORGANISM: Artificial Sequence
<220> FEATURE:
<223> OTHER INFORMATION: MRSG-6H

<400> SEQUENCE: 3

Met Arg Gly Ser His His His His His His
1               5                   10
```

```
<210> SEQ ID NO 4
<211> LENGTH: 6
<212> TYPE: PRT
<213> ORGANISM: Artificial Sequence
<220> FEATURE:
<223> OTHER INFORMATION: 6His

<400> SEQUENCE: 4

His His His His His His
1               5

<210> SEQ ID NO 5
<211> LENGTH: 568
<212> TYPE: PRT
<213> ORGANISM: Bacillus anthracis

<400> SEQUENCE: 5

Ser Thr Ser Ala Gly Pro Thr Val Pro Asp Arg Asp Asn Asp Gly Ile
1               5                   10                  15

Pro Asp Ser Leu Glu Val Glu Gly Tyr Thr Val Asp Val Lys Asn Lys
                20                  25                  30

Arg Thr Phe Leu Ser Pro Trp Ile Ser Asn Ile His Glu Lys Lys Gly
            35                  40                  45

Leu Thr Lys Tyr Lys Ser Ser Pro Glu Lys Trp Ser Thr Ala Ser Asp
        50                  55                  60

Pro Tyr Ser Asp Phe Glu Lys Val Thr Gly Arg Ile Asp Lys Asn Val
65                  70                  75                  80

Ser Pro Glu Ala Arg His Pro Leu Val Ala Ala Tyr Pro Ile Val His
                85                  90                  95

Val Asp Met Glu Asn Ile Ile Leu Ser Lys Asn Glu Asp Gln Ser Thr
                100                 105                 110

Gln Asn Thr Asp Ser Gln Thr Arg Thr Ile Ser Lys Asn Thr Ser Thr
            115                 120                 125

Ser Arg Thr His Thr Ser Glu Val His Gly Asn Ala Glu Val His Ala
        130                 135                 140

Ser Phe Phe Asp Ile Gly Gly Ser Val Ser Ala Gly Phe Ser Asn Ser
145                 150                 155                 160

Asn Ser Ser Thr Val Ala Ile Asp His Ser Leu Ser Leu Ala Gly Glu
                165                 170                 175

Arg Thr Trp Ala Glu Thr Met Gly Leu Asn Thr Ala Asp Thr Ala Arg
                180                 185                 190

Leu Asn Ala Asn Ile Arg Tyr Val Asn Thr Gly Thr Ala Pro Ile Tyr
            195                 200                 205

Asn Val Leu Pro Thr Thr Ser Leu Val Leu Gly Lys Asn Gln Thr Leu
        210                 215                 220

Ala Thr Ile Lys Ala Lys Glu Asn Gln Leu Ser Gln Ile Leu Ala Pro
225                 230                 235                 240

Asn Asn Tyr Tyr Pro Ser Lys Asn Leu Ala Pro Ile Ala Leu Asn Ala
                245                 250                 255

Gln Asp Asp Phe Ser Ser Thr Pro Ile Thr Met Asn Tyr Asn Gln Phe
                260                 265                 270

Leu Glu Leu Glu Lys Thr Lys Gln Leu Arg Leu Asp Thr Asp Gln Val
            275                 280                 285

Tyr Gly Asn Ile Ala Thr Tyr Asn Phe Glu Asn Gly Arg Val Arg Val
        290                 295                 300

Asp Thr Gly Ser Asn Trp Ser Glu Val Leu Pro Gln Ile Gln Glu Thr
305                 310                 315                 320
```

```
Thr Ala Arg Ile Ile Phe Asn Gly Lys Asp Leu Asn Leu Val Glu Arg
            325                 330                 335

Arg Ile Ala Ala Val Asn Pro Ser Asp Pro Leu Glu Thr Thr Lys Pro
            340                 345                 350

Asp Met Thr Leu Lys Glu Ala Leu Lys Ile Ala Phe Gly Phe Asn Glu
            355                 360                 365

Pro Asn Gly Asn Leu Gln Tyr Gln Gly Lys Asp Ile Thr Glu Phe Asp
            370                 375                 380

Phe Asn Phe Asp Gln Gln Thr Ser Gln Asn Ile Lys Asn Gln Leu Ala
385                 390                 395                 400

Glu Leu Asn Ala Thr Asn Ile Tyr Thr Val Leu Asp Lys Ile Lys Leu
            405                 410                 415

Asn Ala Lys Met Asn Ile Leu Ile Arg Asp Lys Arg Phe His Tyr Asp
            420                 425                 430

Arg Asn Asn Ile Ala Val Gly Ala Asp Glu Ser Val Val Lys Glu Ala
            435                 440                 445

His Arg Glu Val Ile Asn Ser Ser Thr Glu Gly Leu Leu Leu Asn Ile
            450                 455                 460

Asp Lys Asp Ile Arg Lys Ile Leu Ser Gly Tyr Ile Val Glu Ile Glu
465                 470                 475                 480

Asp Thr Glu Gly Leu Lys Glu Val Ile Asn Asp Arg Tyr Asp Met Leu
            485                 490                 495

Asn Ile Ser Ser Leu Arg Gln Asp Gly Lys Thr Phe Ile Asp Phe Lys
            500                 505                 510

Lys Tyr Asn Asp Lys Leu Pro Leu Tyr Ile Ser Asn Pro Asn Tyr Lys
            515                 520                 525

Val Asn Val Tyr Ala Val Thr Lys Glu Asn Thr Ile Ile Asn Pro Ser
            530                 535                 540

Glu Asn Gly Asp Thr Ser Thr Asn Gly Ile Lys Lys Ile Leu Ile Phe
545                 550                 555                 560

Ser Lys Lys Gly Tyr Glu Ile Gly
            565

<210> SEQ ID NO 6
<211> LENGTH: 108
<212> TYPE: PRT
<213> ORGANISM: Artificial Sequence
<220> FEATURE:
<223> OTHER INFORMATION: fragment of B. anthracis PA63

<400> SEQUENCE: 6

Val His Val Asp Met Glu Asn Ile Ile Leu Ser Lys Asn Glu Asp Gln
1               5                   10                  15

Ser Thr Gln Asn Thr Asp Ser Gln Thr Arg Thr Ile Ser Lys Asn Thr
            20                  25                  30

Ser Thr Ser Arg Thr His Thr Ser Glu Val His Gly Asn Ala Glu Val
            35                  40                  45

His Ala Ser Phe Phe Asp Ile Gly Gly Ser Val Ser Ala Gly Phe Ser
            50                  55                  60

Asn Ser Asn Ser Ser Thr Val Ala Ile Asp His Ser Leu Ser Leu Ala
65                  70                  75                  80

Gly Glu Arg Thr Trp Ala Glu Thr Met Gly Leu Asn Thr Ala Asp Thr
            85                  90                  95

Ala Arg Leu Asn Ala Asn Ile Arg Tyr Val Asn Thr
            100                 105
```

<210> SEQ ID NO 7
<211> LENGTH: 747
<212> TYPE: PRT
<213> ORGANISM: Artificial Sequence
<220> FEATURE:
<223> OTHER INFORMATION: b. anthracis PA83 D512K mutant

<400> SEQUENCE: 7

```
Met Arg Gly Ser His His His His His His Gly Ser Glu Val Lys Gln
1               5                   10                  15

Glu Asn Arg Leu Leu Asn Glu Ser Ser Ser Gln Gly Leu Leu
            20                  25                  30

Gly Tyr Tyr Phe Ser Asp Leu Asn Phe Gln Ala Pro Met Val Val Thr
            35                  40                  45

Ser Ser Thr Thr Gly Asp Leu Ser Ile Pro Ser Ser Glu Leu Glu Asn
50                  55                  60

Ile Pro Ser Glu Asn Gln Tyr Phe Gln Ser Ala Ile Trp Ser Gly Phe
65                  70                  75                  80

Ile Lys Val Lys Lys Ser Asp Glu Tyr Thr Phe Ala Thr Ser Ala Asp
                85                  90                  95

Asn His Val Thr Met Trp Val Asp Asp Gln Glu Val Ile Asn Lys Ala
            100                 105                 110

Ser Asn Ser Asn Lys Ile Arg Leu Glu Lys Gly Arg Leu Tyr Gln Ile
            115                 120                 125

Lys Ile Gln Tyr Gln Arg Glu Asn Pro Thr Glu Lys Gly Leu Asp Phe
        130                 135                 140

Lys Leu Tyr Trp Thr Asp Ser Gln Asn Lys Lys Glu Val Ile Ser Ser
145                 150                 155                 160

Asp Asn Leu Gln Leu Pro Glu Leu Lys Gln Lys Ser Ser Asn Ser Arg
                165                 170                 175

Lys Lys Arg Ser Thr Ser Ala Gly Pro Thr Val Pro Asp Arg Asp Asn
            180                 185                 190

Asp Gly Ile Pro Asp Ser Leu Glu Val Glu Gly Tyr Thr Val Asp Val
        195                 200                 205

Lys Asn Lys Arg Thr Phe Leu Ser Pro Trp Ile Ser Asn Ile His Glu
210                 215                 220

Lys Lys Gly Leu Thr Lys Tyr Lys Ser Ser Pro Glu Lys Trp Ser Thr
225                 230                 235                 240

Ala Ser Asp Pro Tyr Ser Asp Phe Glu Lys Val Thr Gly Arg Ile Asp
                245                 250                 255

Lys Asn Val Ser Pro Glu Ala Arg His Pro Leu Val Ala Ala Tyr Pro
            260                 265                 270

Ile Val His Val Asp Met Glu Asn Ile Ile Leu Ser Lys Asn Glu Asp
        275                 280                 285

Gln Ser Thr Gln Asn Thr Asp Ser Gln Thr Arg Thr Ile Ser Lys Asn
        290                 295                 300

Thr Ser Thr Ser Arg Thr His Thr Ser Glu Val His Gly Asn Ala Glu
305                 310                 315                 320

Val His Ala Ser Phe Phe Asp Ile Gly Gly Ser Val Ser Ala Gly Phe
                325                 330                 335

Ser Asn Ser Asn Ser Ser Thr Val Ala Ile Asp His Ser Leu Ser Leu
            340                 345                 350

Ala Gly Glu Arg Thr Trp Ala Glu Thr Met Gly Leu Asn Thr Ala Asp
        355                 360                 365
```

Thr Ala Arg Leu Asn Ala Asn Ile Arg Tyr Val Asn Thr Gly Thr Ala
            370                 375                 380

Pro Ile Tyr Asn Val Leu Pro Thr Thr Ser Leu Val Leu Gly Lys Asn
385                 390                 395                 400

Gln Thr Leu Ala Thr Ile Lys Ala Lys Glu Asn Gln Leu Ser Gln Ile
            405                 410                 415

Leu Ala Pro Asn Asn Tyr Tyr Pro Ser Lys Asn Leu Ala Pro Ile Ala
            420                 425                 430

Leu Asn Ala Gln Asp Asp Phe Ser Thr Pro Ile Thr Met Asn Tyr
            435                 440                 445

Asn Gln Phe Leu Glu Leu Glu Lys Thr Lys Gln Leu Arg Leu Asp Thr
450                 455                 460

Asp Gln Val Tyr Gly Asn Ile Ala Thr Tyr Asn Phe Glu Asn Gly Arg
465                 470                 475                 480

Val Arg Val Asp Thr Gly Ser Asn Trp Ser Glu Val Leu Pro Gln Ile
            485                 490                 495

Gln Glu Thr Thr Ala Arg Ile Ile Phe Asn Gly Lys Asp Leu Asn Leu
            500                 505                 510

Val Glu Arg Arg Ile Ala Ala Val Asn Pro Ser Lys Pro Leu Glu Thr
            515                 520                 525

Thr Lys Pro Asp Met Thr Leu Lys Glu Ala Leu Lys Ile Ala Phe Gly
            530                 535                 540

Phe Asn Glu Pro Asn Gly Asn Leu Gln Tyr Gln Gly Lys Asp Ile Thr
545                 550                 555                 560

Glu Phe Asp Phe Asn Phe Asp Gln Gln Thr Ser Gln Asn Ile Lys Asn
            565                 570                 575

Gln Leu Ala Glu Leu Asn Ala Thr Asn Ile Tyr Thr Val Leu Asp Lys
            580                 585                 590

Ile Lys Leu Asn Ala Lys Met Asn Ile Leu Ile Arg Asp Lys Arg Phe
            595                 600                 605

His Tyr Asp Arg Asn Asn Ile Ala Val Gly Ala Asp Glu Ser Val Val
            610                 615                 620

Lys Glu Ala His Arg Glu Val Ile Asn Ser Ser Thr Glu Gly Leu Leu
625                 630                 635                 640

Leu Asn Ile Asp Lys Asp Ile Arg Lys Ile Leu Ser Gly Tyr Ile Val
            645                 650                 655

Glu Ile Glu Asp Thr Glu Gly Leu Lys Glu Val Ile Asn Asp Arg Tyr
            660                 665                 670

Asp Met Leu Asn Ile Ser Ser Leu Arg Gln Asp Gly Lys Thr Phe Ile
            675                 680                 685

Asp Phe Lys Lys Tyr Asn Asp Lys Leu Pro Leu Tyr Ile Ser Asn Pro
690                 695                 700

Asn Tyr Lys Val Asn Val Tyr Ala Val Thr Lys Glu Asn Thr Ile Ile
705                 710                 715                 720

Asn Pro Ser Glu Asn Gly Asp Thr Ser Thr Asn Gly Ile Lys Lys Ile
            725                 730                 735

Leu Ile Phe Ser Lys Lys Gly Tyr Glu Ile Gly
            740                 745

<210> SEQ ID NO 8
<211> LENGTH: 747
<212> TYPE: PRT
<213> ORGANISM: Artificial Sequence
<220> FEATURE:

<223> OTHER INFORMATION: B. anthracis PA83 K245G; R252N [16] mutant

<400> SEQUENCE: 8

| | | | | | | | | | | | | | | |
|---|---|---|---|---|---|---|---|---|---|---|---|---|---|---|
| Met | Arg | Gly | Ser | His | His | His | His | His | Gly | Ser | Glu | Val | Lys | Gln |
| 1 | | | | 5 | | | | | 10 | | | | | 15 |
| Glu | Asn | Arg | Leu | Leu | Asn | Glu | Ser | Glu | Ser | Ser | Ser | Gln | Gly | Leu | Leu |
| | | | 20 | | | | | 25 | | | | | 30 | | |
| Gly | Tyr | Tyr | Phe | Ser | Asp | Leu | Asn | Phe | Gln | Ala | Pro | Met | Val | Val | Thr |
| | | 35 | | | | | 40 | | | | | 45 | | | |
| Ser | Ser | Thr | Thr | Gly | Asp | Leu | Ser | Ile | Pro | Ser | Ser | Glu | Leu | Glu | Asn |
| 50 | | | | | 55 | | | | | 60 | | | | | |
| Ile | Pro | Ser | Glu | Asn | Gln | Tyr | Phe | Gln | Ser | Ala | Ile | Trp | Ser | Gly | Phe |
| 65 | | | | | 70 | | | | | 75 | | | | | 80 |
| Ile | Lys | Val | Lys | Lys | Ser | Asp | Glu | Tyr | Thr | Phe | Ala | Thr | Ser | Ala | Asp |
| | | | | 85 | | | | | 90 | | | | | 95 | |
| Asn | His | Val | Thr | Met | Trp | Val | Asp | Asp | Gln | Glu | Val | Ile | Asn | Lys | Ala |
| | | | 100 | | | | | 105 | | | | | 110 | | |
| Ser | Asn | Ser | Asn | Lys | Ile | Arg | Leu | Glu | Lys | Gly | Arg | Leu | Tyr | Gln | Ile |
| | | 115 | | | | | 120 | | | | | 125 | | | |
| Lys | Ile | Gln | Tyr | Gln | Arg | Glu | Asn | Pro | Thr | Glu | Lys | Gly | Leu | Asp | Phe |
| 130 | | | | | 135 | | | | | 140 | | | | | |
| Lys | Leu | Tyr | Trp | Thr | Asp | Ser | Gln | Asn | Lys | Lys | Glu | Val | Ile | Ser | Ser |
| 145 | | | | | 150 | | | | | 155 | | | | | 160 |
| Asp | Asn | Leu | Gln | Leu | Pro | Glu | Leu | Lys | Gln | Lys | Ser | Ser | Asn | Ser | Arg |
| | | | 165 | | | | | 170 | | | | | 175 | | |
| Lys | Lys | Arg | Ser | Thr | Ser | Ala | Gly | Pro | Thr | Val | Pro | Asp | Arg | Asp | Asn |
| | | | 180 | | | | | 185 | | | | | 190 | | |
| Asp | Gly | Ile | Pro | Asp | Ser | Leu | Glu | Val | Glu | Gly | Tyr | Thr | Val | Asp | Val |
| | | 195 | | | | | 200 | | | | | 205 | | | |
| Lys | Asn | Lys | Arg | Thr | Phe | Leu | Ser | Pro | Trp | Ile | Ser | Asn | Ile | His | Glu |
| | 210 | | | | | 215 | | | | | 220 | | | | |
| Lys | Lys | Gly | Leu | Thr | Lys | Tyr | Lys | Ser | Ser | Pro | Glu | Lys | Trp | Ser | Thr |
| 225 | | | | | 230 | | | | | 235 | | | | | 240 |
| Ala | Ser | Asp | Pro | Tyr | Ser | Asp | Phe | Glu | Lys | Val | Thr | Gly | Arg | Ile | Asp |
| | | | 245 | | | | | 250 | | | | | 255 | | |
| Gly | Asn | Val | Ser | Pro | Glu | Ala | Asn | His | Pro | Leu | Val | Ala | Ala | Tyr | Pro |
| | | | 260 | | | | | 265 | | | | | 270 | | |
| Ile | Val | His | Val | Asp | Met | Glu | Asn | Ile | Ile | Leu | Ser | Lys | Asn | Glu | Asp |
| | | 275 | | | | | 280 | | | | | 285 | | | |
| Gln | Ser | Thr | Gln | Asn | Thr | Asp | Ser | Gln | Thr | Arg | Thr | Ile | Ser | Lys | Asn |
| | 290 | | | | | 295 | | | | | 300 | | | | |
| Thr | Ser | Thr | Ser | Arg | Thr | His | Thr | Ser | Glu | Val | His | Gly | Asn | Ala | Glu |
| 305 | | | | | 310 | | | | | 315 | | | | | 320 |
| Val | His | Ala | Ser | Phe | Phe | Asp | Ile | Gly | Gly | Ser | Val | Ser | Ala | Gly | Phe |
| | | | | 325 | | | | | 330 | | | | | 335 | |
| Ser | Asn | Ser | Asn | Ser | Ser | Thr | Val | Ala | Ile | Asp | His | Ser | Leu | Ser | Leu |
| | | | 340 | | | | | 345 | | | | | 350 | | |
| Ala | Gly | Glu | Arg | Thr | Trp | Ala | Glu | Thr | Met | Gly | Leu | Asn | Thr | Ala | Asp |
| | | 355 | | | | | 360 | | | | | 365 | | | |
| Thr | Ala | Arg | Leu | Asn | Ala | Asn | Ile | Arg | Tyr | Val | Asn | Thr | Gly | Thr | Ala |
| | 370 | | | | | 375 | | | | | 380 | | | | |
| Pro | Ile | Tyr | Asn | Val | Leu | Pro | Thr | Thr | Ser | Leu | Val | Leu | Gly | Lys | Asn |
| 385 | | | | | 390 | | | | | 395 | | | | | 400 |

Gln Thr Leu Ala Thr Ile Lys Ala Lys Glu Asn Gln Leu Ser Gln Ile
                405                 410                 415

Leu Ala Pro Asn Tyr Tyr Pro Ser Lys Asn Leu Ala Pro Ile Ala
        420                 425                 430

Leu Asn Ala Gln Asp Asp Phe Ser Ser Thr Pro Ile Thr Met Asn Tyr
        435                 440                 445

Asn Gln Phe Leu Glu Leu Glu Lys Thr Lys Gln Leu Arg Leu Asp Thr
    450                 455                 460

Asp Gln Val Tyr Gly Asn Ile Ala Thr Tyr Asn Phe Glu Asn Gly Arg
465                 470                 475                 480

Val Arg Val Asp Thr Gly Ser Asn Trp Ser Glu Val Leu Pro Gln Ile
                485                 490                 495

Gln Glu Thr Thr Ala Arg Ile Ile Phe Asn Gly Lys Asp Leu Asn Leu
                500                 505                 510

Val Glu Arg Arg Ile Ala Ala Val Asn Pro Ser Asp Pro Leu Glu Thr
            515                 520                 525

Thr Lys Pro Asp Met Thr Leu Lys Glu Ala Leu Lys Ile Ala Phe Gly
    530                 535                 540

Phe Asn Glu Pro Asn Gly Asn Leu Gln Tyr Gln Gly Lys Asp Ile Thr
545                 550                 555                 560

Glu Phe Asp Phe Asn Phe Asp Gln Gln Thr Ser Gln Asn Ile Lys Asn
                565                 570                 575

Gln Leu Ala Glu Leu Asn Ala Thr Asn Ile Tyr Thr Val Leu Asp Lys
            580                 585                 590

Ile Lys Leu Asn Ala Lys Met Asn Ile Leu Ile Arg Asp Lys Arg Phe
595                 600                 605

His Tyr Asp Arg Asn Asn Ile Ala Val Gly Ala Asp Glu Ser Val Val
    610                 615                 620

Lys Glu Ala His Arg Glu Val Ile Asn Ser Ser Thr Glu Gly Leu Leu
625                 630                 635                 640

Leu Asn Ile Asp Lys Asp Ile Arg Lys Ile Leu Ser Gly Tyr Ile Val
                645                 650                 655

Glu Ile Glu Asp Thr Glu Gly Leu Lys Glu Val Ile Asn Asp Arg Tyr
                660                 665                 670

Asp Met Leu Asn Ile Ser Ser Leu Arg Gln Asp Gly Lys Thr Phe Ile
            675                 680                 685

Asp Phe Lys Lys Tyr Asn Asp Lys Leu Pro Leu Tyr Ile Ser Asn Pro
    690                 695                 700

Asn Tyr Lys Val Asn Val Tyr Ala Val Thr Lys Glu Asn Thr Ile Ile
705                 710                 715                 720

Asn Pro Ser Glu Asn Gly Asp Thr Ser Thr Asn Gly Ile Lys Lys Ile
                725                 730                 735

Leu Ile Phe Ser Lys Lys Gly Tyr Glu Ile Gly
                740                 745

<210> SEQ ID NO 9
<211> LENGTH: 747
<212> TYPE: PRT
<213> ORGANISM: Artificial Sequence
<220> FEATURE:
<223> OTHER INFORMATION: B. anthracis PA83 K245N; R252S [16] mutant

<400> SEQUENCE: 9

Met Arg Gly Ser His His His His His His Gly Ser Glu Val Lys Gln
1               5                   10                  15

```
Glu Asn Arg Leu Leu Asn Glu Ser Ser Ser Gln Gly Leu Leu
             20                  25                  30

Gly Tyr Tyr Phe Ser Asp Leu Asn Phe Gln Ala Pro Met Val Val Thr
         35                  40                  45

Ser Ser Thr Thr Gly Asp Leu Ser Ile Pro Ser Ser Glu Leu Glu Asn
     50                  55                  60

Ile Pro Ser Glu Asn Gln Tyr Phe Gln Ser Ala Ile Trp Ser Gly Phe
 65              70                  75                  80

Ile Lys Val Lys Lys Ser Asp Glu Tyr Thr Phe Ala Thr Ser Ala Asp
                 85                  90                  95

Asn His Val Thr Met Trp Val Asp Asp Gln Glu Val Ile Asn Lys Ala
             100                 105                 110

Ser Asn Ser Asn Lys Ile Arg Leu Glu Lys Gly Arg Leu Tyr Gln Ile
         115                 120                 125

Lys Ile Gln Tyr Gln Arg Glu Asn Pro Thr Glu Lys Gly Leu Asp Phe
     130                 135                 140

Lys Leu Tyr Trp Thr Asp Ser Gln Asn Lys Lys Glu Val Ile Ser Ser
145                 150                 155                 160

Asp Asn Leu Gln Leu Pro Glu Leu Lys Gln Lys Ser Ser Asn Ser Arg
                 165                 170                 175

Lys Lys Arg Ser Thr Ser Ala Gly Pro Thr Val Pro Asp Arg Asp Asn
             180                 185                 190

Asp Gly Ile Pro Asp Ser Leu Glu Val Glu Gly Tyr Thr Val Asp Val
         195                 200                 205

Lys Asn Lys Arg Thr Phe Leu Ser Pro Trp Ile Ser Asn Ile His Glu
     210                 215                 220

Lys Lys Gly Leu Thr Lys Tyr Lys Ser Ser Pro Glu Lys Trp Ser Thr
225                 230                 235                 240

Ala Ser Asp Pro Tyr Ser Asp Phe Glu Lys Val Thr Gly Arg Ile Asp
                 245                 250                 255

Asn Asn Val Ser Pro Glu Ala Ser His Pro Leu Val Ala Ala Tyr Pro
             260                 265                 270

Ile Val His Val Asp Met Glu Asn Ile Ile Leu Ser Lys Asn Glu Asp
         275                 280                 285

Gln Ser Thr Gln Asn Thr Asp Ser Gln Thr Arg Thr Ile Ser Lys Asn
     290                 295                 300

Thr Ser Thr Ser Arg Thr His Thr Ser Glu Val His Gly Asn Ala Glu
305                 310                 315                 320

Val His Ala Ser Phe Phe Asp Ile Gly Gly Ser Val Ser Ala Gly Phe
                 325                 330                 335

Ser Asn Ser Asn Ser Ser Thr Val Ala Ile Asp His Ser Leu Ser Leu
             340                 345                 350

Ala Gly Glu Arg Thr Trp Ala Glu Thr Met Gly Leu Asn Thr Ala Asp
         355                 360                 365

Thr Ala Arg Leu Asn Ala Asn Ile Arg Tyr Val Asn Thr Gly Thr Ala
     370                 375                 380

Pro Ile Tyr Asn Val Leu Pro Thr Thr Ser Leu Val Leu Gly Lys Asn
385                 390                 395                 400

Gln Thr Leu Ala Thr Ile Lys Ala Lys Glu Asn Gln Leu Ser Gln Ile
                 405                 410                 415

Leu Ala Pro Asn Asn Tyr Tyr Pro Ser Lys Asn Leu Ala Pro Ile Ala
             420                 425                 430

Leu Asn Ala Gln Asp Asp Phe Ser Ser Thr Pro Ile Thr Met Asn Tyr
```

```
                435                 440                 445
Asn Gln Phe Leu Glu Leu Glu Lys Thr Lys Gln Leu Arg Leu Asp Thr
450                 455                 460

Asp Gln Val Tyr Gly Asn Ile Ala Thr Tyr Asn Phe Glu Asn Gly Arg
465                 470                 475                 480

Val Arg Val Asp Thr Gly Ser Asn Trp Ser Glu Val Leu Pro Gln Ile
                485                 490                 495

Gln Glu Thr Thr Ala Arg Ile Ile Phe Asn Gly Lys Asp Leu Asn Leu
                500                 505                 510

Val Glu Arg Arg Ile Ala Ala Val Asn Pro Ser Asp Pro Leu Glu Thr
                515                 520                 525

Thr Lys Pro Asp Met Thr Leu Lys Glu Ala Leu Lys Ile Ala Phe Gly
530                 535                 540

Phe Asn Glu Pro Asn Gly Asn Leu Gln Tyr Gln Gly Lys Asp Ile Thr
545                 550                 555                 560

Glu Phe Asp Phe Asn Phe Asp Gln Gln Thr Ser Gln Asn Ile Lys Asn
                565                 570                 575

Gln Leu Ala Glu Leu Asn Ala Thr Asn Ile Tyr Thr Val Leu Asp Lys
                580                 585                 590

Ile Lys Leu Asn Ala Lys Met Asn Ile Leu Ile Arg Asp Lys Arg Phe
                595                 600                 605

His Tyr Asp Arg Asn Asn Ile Ala Val Gly Ala Asp Glu Ser Val Val
                610                 615                 620

Lys Glu Ala His Arg Glu Val Ile Asn Ser Ser Thr Glu Gly Leu Leu
625                 630                 635                 640

Leu Asn Ile Asp Lys Asp Ile Arg Lys Ile Leu Ser Gly Tyr Ile Val
                645                 650                 655

Glu Ile Glu Asp Thr Glu Gly Leu Lys Glu Val Ile Asn Asp Arg Tyr
                660                 665                 670

Asp Met Leu Asn Ile Ser Ser Leu Arg Gln Asp Gly Lys Thr Phe Ile
                675                 680                 685

Asp Phe Lys Lys Tyr Asn Asp Lys Leu Pro Leu Tyr Ile Ser Asn Pro
690                 695                 700

Asn Tyr Lys Val Asn Val Tyr Ala Val Thr Lys Glu Asn Thr Ile Ile
705                 710                 715                 720

Asn Pro Ser Glu Asn Gly Asp Thr Ser Thr Asn Gly Ile Lys Lys Ile
                725                 730                 735

Leu Ile Phe Ser Lys Lys Gly Tyr Glu Ile Gly
                740                 745

<210> SEQ ID NO 10
<211> LENGTH: 738
<212> TYPE: PRT
<213> ORGANISM: Artificial Sequence
<220> FEATURE:
<223> OTHER INFORMATION: B. anthracis PA83-HL hybrid molecule

<400> SEQUENCE: 10

Gly Ser Glu Val Lys Gln Glu Asn Arg Leu Leu Asn Glu Ser Glu Ser
1               5                   10                  15

Ser Ser Gln Gly Leu Leu Gly Tyr Tyr Phe Ser Asp Leu Asn Phe Gln
                20                  25                  30

Ala Pro Met Val Val Thr Ser Ser Thr Thr Gly Asp Leu Ser Ile Pro
                35                  40                  45

Ser Ser Glu Leu Glu Asn Ile Pro Ser Glu Asn Gln Tyr Phe Gln Ser
```

```
                 50                  55                  60
Ala Ile Trp Ser Gly Phe Ile Lys Val Lys Ser Asp Glu Tyr Thr
 65                  70                  75                  80

Phe Ala Thr Ser Ala Asp Asn His Val Thr Met Trp Val Asp Asp Gln
                 85                  90                  95

Glu Val Ile Asn Lys Ala Ser Asn Ser Asn Lys Ile Arg Leu Glu Lys
                    100                 105                 110

Gly Arg Leu Tyr Gln Ile Lys Ile Gln Tyr Gln Arg Glu Asn Pro Thr
                    115                 120                 125

Glu Lys Gly Leu Asp Phe Lys Leu Tyr Trp Thr Asp Ser Gln Asn Lys
                    130                 135                 140

Lys Glu Val Ile Ser Ser Asp Asn Leu Gln Leu Pro Glu Leu Lys Gln
145                 150                 155                 160

Lys Ser Ser Asn Ser Arg Lys Lys Arg Ser Thr Ser Ala Gly Pro Thr
                    165                 170                 175

Val Pro Asp Arg Asp Asn Asp Gly Ile Pro Asp Ser Leu Glu Val Glu
                    180                 185                 190

Gly Tyr Thr Val Asp Val Lys Asn Lys Arg Thr Phe Leu Ser Pro Trp
                    195                 200                 205

Ile Ser Asn Ile His Glu Lys Lys Gly Leu Thr Lys Tyr Lys Ser Ser
                    210                 215                 220

Pro Glu Lys Trp Ser Thr Ala Ser Asp Pro Tyr Ser Asp Phe Glu Lys
225                 230                 235                 240

Val Thr Gly Arg Ile Asp Lys Asn Val Ser Pro Glu Ala Arg His Pro
                    245                 250                 255

Leu Val Ala Ala Tyr Pro Ile Val His Val Asp Met Glu Asn Ile Ile
                    260                 265                 270

Leu Ser Lys Asn Glu Asp Gln Ser Thr Gln Asn Thr Asp Ser Gln Thr
                    275                 280                 285

Arg Thr Ile Ser Lys Asn Thr Ser Lys Glu Tyr Met Ser Thr Leu Thr
                    290                 295                 300

Tyr Gly Phe Asn Gly Asn Val Thr Gly Asp Asp Thr Gly Lys Ile Gly
305                 310                 315                 320

Gly Leu Ile Gly Ala Asn Val Ser Ile Gly His Thr Leu Lys Tyr Ala
                    325                 330                 335

Ile Asp His Ser Leu Ser Leu Ala Gly Glu Arg Thr Trp Ala Glu Thr
                    340                 345                 350

Met Gly Leu Asn Thr Ala Asp Thr Ala Arg Leu Asn Ala Asn Ile Arg
                    355                 360                 365

Tyr Val Asn Thr Gly Thr Ala Pro Ile Tyr Asn Val Leu Pro Thr Thr
                    370                 375                 380

Ser Leu Val Leu Gly Lys Asn Gln Thr Leu Ala Thr Ile Lys Ala Lys
385                 390                 395                 400

Glu Asn Gln Leu Ser Gln Ile Leu Ala Pro Asn Asn Tyr Tyr Pro Ser
                    405                 410                 415

Lys Asn Leu Ala Pro Ile Ala Leu Asn Ala Gln Asp Asp Phe Ser Ser
                    420                 425                 430

Thr Pro Ile Thr Met Asn Tyr Asn Gln Phe Leu Glu Leu Glu Lys Thr
                    435                 440                 445

Lys Gln Leu Arg Leu Asp Thr Asp Gln Val Tyr Gly Asn Ile Ala Thr
                    450                 455                 460

Tyr Asn Phe Glu Asn Gly Arg Val Arg Val Asp Thr Gly Ser Asn Trp
465                 470                 475                 480
```

```
Ser Glu Val Leu Pro Gln Ile Gln Glu Thr Thr Ala Arg Ile Ile Phe
                485                 490                 495

Asn Gly Lys Asp Leu Asn Leu Val Glu Arg Arg Ile Ala Ala Val Asn
            500                 505                 510

Pro Ser Asp Pro Leu Glu Thr Thr Lys Pro Asp Met Thr Leu Lys Glu
        515                 520                 525

Ala Leu Lys Ile Ala Phe Gly Phe Asn Glu Pro Asn Gly Asn Leu Gln
    530                 535                 540

Tyr Gln Gly Lys Asp Ile Thr Glu Phe Asp Phe Asn Phe Asp Gln Gln
545                 550                 555                 560

Thr Ser Gln Asn Ile Lys Asn Gln Leu Ala Glu Leu Asn Ala Thr Asn
                565                 570                 575

Ile Tyr Thr Val Leu Asp Lys Ile Lys Leu Asn Ala Lys Met Asn Ile
            580                 585                 590

Leu Ile Arg Asp Lys Arg Phe His Tyr Asp Arg Asn Asn Ile Ala Val
        595                 600                 605

Gly Ala Asp Glu Ser Val Val Lys Glu Ala His Arg Glu Val Ile Asn
    610                 615                 620

Ser Ser Thr Glu Gly Leu Leu Leu Asn Ile Asp Lys Asp Ile Arg Lys
625                 630                 635                 640

Ile Leu Ser Gly Tyr Ile Val Glu Ile Glu Asp Thr Glu Gly Leu Lys
                645                 650                 655

Glu Val Ile Asn Asp Arg Tyr Asp Met Leu Asn Ile Ser Ser Leu Arg
            660                 665                 670

Gln Asp Gly Lys Thr Phe Ile Asp Phe Lys Lys Tyr Asn Asp Lys Leu
        675                 680                 685

Pro Leu Tyr Ile Ser Asn Pro Asn Tyr Lys Val Asn Val Tyr Ala Val
    690                 695                 700

Thr Lys Glu Asn Thr Ile Ile Asn Pro Ser Glu Asn Gly Asp Thr Ser
705                 710                 715                 720

Thr Asn Gly Ile Lys Lys Ile Leu Ile Phe Ser Lys Lys Gly Tyr Glu
                725                 730                 735

Ile Gly

<210> SEQ ID NO 11
<211> LENGTH: 230
<212> TYPE: PRT
<213> ORGANISM: Artificial Sequence
<220> FEATURE:
<223> OTHER INFORMATION: lethal factor domain I (LFn)

<400> SEQUENCE: 11

Met Glu Arg Asn Lys Thr Gln Glu Glu His Leu Lys Glu Ile Met Lys
1               5                   10                  15

His Ile Val Lys Ile Glu Val Lys Gly Glu Glu Ala Val Lys Lys Glu
            20                  25                  30

Ala Ala Glu Lys Leu Leu Glu Lys Val Pro Ser Asp Val Leu Glu Met
        35                  40                  45

Tyr Lys Ala Ile Gly Gly Lys Ile Tyr Ile Val Asp Gly Asp Ile Thr
    50                  55                  60

Lys His Ile Ser Leu Glu Ala Leu Ser Glu Asp Lys Lys Lys Ile Lys
65                  70                  75                  80

Asp Ile Tyr Gly Lys Asp Ala Leu Leu His Glu His Tyr Val T

```
Lys Glu Gly Tyr Glu Pro Val Leu Val Ile Gln Ser Ser Glu Asp Tyr
            100                 105                 110

Val Glu Asn Thr Glu Lys Ala Leu Asn Val Tyr Tyr Glu Ile Gly Lys
        115                 120                 125

Ile Leu Ser Arg Asp Ile Leu Ser Lys Ile Asn Gln Pro Tyr Gln Lys
    130                 135                 140

Phe Leu Asp Val Leu Asn Thr Ile Lys Asn Ala Ser Asp Ser Asp Gly
145                 150                 155                 160

Gln Asp Leu Leu Phe Thr Asn Gln Leu Lys Glu His Pro Thr Asp Phe
                165                 170                 175

Ser Val Glu Phe Leu Glu Gln Asn Ser Asn Glu Val Gln Glu Val Phe
            180                 185                 190

Ala Lys Ala Phe Ala Tyr Tyr Ile Glu Pro Gln His Arg Asp Val Leu
        195                 200                 205

Gln Leu Tyr Ala Pro Glu Ala Phe Asn Tyr Met Asp Lys Phe Asn Glu
    210                 215                 220

Gln Glu Ile Asn Leu Ser
225                 230

<210> SEQ ID NO 12
<211> LENGTH: 398
<212> TYPE: PRT
<213> ORGANISM: Artificial Sequence
<220> FEATURE:
<223> OTHER INFORMATION: Saccharomyces cerevisiae GAL4 (fused with LFn)

<400> SEQUENCE: 12

Met Gly Lys Pro Ile Pro Asn Pro Leu Leu Gly Leu Asp Ser Thr Met
1               5                   10                  15

Glu Arg Asn Lys Thr Gln Glu Glu His Leu Lys Glu Ile Met Lys His
            20                  25                  30

Ile Val Lys Ile Glu Val Lys Gly Glu Glu Ala Val Lys Lys Glu Ala
        35                  40                  45

Ala Glu Lys Leu Leu Glu Lys Val Pro Ser Asp Val Leu Glu Met Tyr
    50                  55                  60

Lys Ala Ile Gly Gly Lys Ile Tyr Ile Val Asp Gly Asp Ile Thr Lys
65                  70                  75                  80

His Ile Ser Leu Glu Ala Leu Ser Glu Asp Lys Lys Lys Ile Lys Asp
                85                  90                  95

Ile Tyr Gly Lys Asp Ala Leu Leu His Glu His Tyr Val Tyr Ala Lys
            100                 105                 110

Glu Gly Tyr Glu Pro Val Leu Val Ile Gln Ser Ser Glu Asp Tyr Val
        115                 120                 125

Glu Asn Thr Glu Lys Ala Leu Asn Val Tyr Tyr Glu Ile Gly Lys Ile
    130                 135                 140

Leu Ser Arg Asp Ile Leu Ser Lys Ile Asn Gln Pro Tyr Gln Lys Phe
145                 150                 155                 160

Leu Asp Val Leu Asn Thr Ile Lys Asn Ala Ser Asp Ser Asp Gly Gln
                165                 170                 175

Asp Leu Leu Phe Thr Asn Gln Leu Lys Glu His Pro Thr Asp Phe Ser
            180                 185                 190

Val Glu Phe Leu Glu Gln Asn Ser Asn Glu Val Gln Glu Val Phe Ala
        195                 200                 205

Lys Ala Phe Ala Tyr Tyr Ile Glu Pro Gln His Arg Asp Val Leu Gln
    210                 215                 220
```

```
Leu Tyr Ala Pro Glu Ala Phe Asn Tyr Met Asp Lys Phe Asn Glu Gln
225                 230                 235                 240

Glu Ile Asn Leu Ser Met Lys Leu Leu Ser Ser Ile Glu Gln Ala Cys
            245                 250                 255

Asp Ile Cys Arg Leu Lys Lys Leu Lys Cys Ser Lys Glu Lys Pro Lys
            260                 265                 270

Cys Ala Lys Cys Leu Lys Asn Asn Trp Glu Cys Arg Tyr Ser Pro Lys
        275                 280                 285

Thr Lys Arg Ser Pro Leu Thr Arg Ala His Leu Thr Glu Val Glu Ser
    290                 295                 300

Arg Leu Glu Arg Leu Glu Gln Leu Phe Leu Leu Ile Phe Pro Arg Glu
305                 310                 315                 320

Asp Leu Asp Met Ile Leu Lys Met Asp Ser Leu Gln Asp Ile Lys Ala
            325                 330                 335

Leu Leu Thr Gly Leu Phe Val Gln Asp Asn Val Asn Lys Asp Ala Val
            340                 345                 350

Thr Asp Arg Leu Ala Ser Val Glu Thr Asp Met Pro Leu Thr Leu Arg
            355                 360                 365

Gln His Arg Ile Ser Ala Thr Ser Ser Glu Glu Ser Ser Asn Lys
    370                 375                 380

Gly Gln Arg Gln Leu Thr Val Ser His His His His His
385                 390                 395

<210> SEQ ID NO 13
<211> LENGTH: 329
<212> TYPE: PRT
<213> ORGANISM: Artificial Sequence
<220> FEATURE:
<223> OTHER INFORMATION: Protein Kinase R

<400> SEQUENCE: 13

Met Gly Lys Pro Ile Pro Asn Pro Leu Leu Gly Leu Asp Ser Thr Met
1               5                   10                  15

Glu Arg Asn Lys Thr Gln Glu Glu His Leu Lys Glu Ile Met Lys His
            20                  25                  30

Ile Val Lys Ile Glu Val Lys Gly Glu Glu Ala Val Lys Lys Glu Ala
        35                  40                  45

Ala Glu Lys Leu Leu Glu Lys Val Pro Ser Asp Val Leu Glu Met Tyr
    50                  55                  60

Lys Ala Ile Gly Gly Lys Ile Tyr Ile Val Asp Gly Asp Ile Thr Lys
65                  70                  75                  80

His Ile Ser Leu Glu Ala Leu Ser Glu Asp Lys Lys Lys Ile Lys Asp
                85                  90                  95

Ile Tyr Gly Lys Asp Ala Leu Leu His Glu His Tyr Val Tyr Ala Lys
            100                 105                 110

Glu Gly Tyr Glu Pro Val Leu Val Ile Gln Ser Ser Glu Asp Tyr Val
        115                 120                 125

Glu Asn Thr Glu Lys Ala Leu Asn Val Tyr Tyr Glu Ile Gly Lys Ile
    130                 135                 140

Leu Ser Arg Asp Ile Leu Ser Lys Ile Asn Gln Pro Tyr Gln Lys Phe
145                 150                 155                 160

Leu Asp Val Leu Asn Thr Ile Lys Asn Ala Ser Asp Ser Asp Gly Gln
                165                 170                 175

Asp Leu Leu Phe Thr Asn Gln Leu Lys Glu His Pro Thr Asp Phe Ser
            180                 185                 190
```

```
Val Glu Phe Leu Glu Gln Asn Ser Asn Glu Val Gln Glu Val Phe Ala
            195                 200                 205

Lys Ala Phe Ala Tyr Tyr Ile Glu Pro Gln His Arg Asp Val Leu Gln
210                 215                 220

Leu Tyr Ala Pro Glu Ala Phe Asn Tyr Met Asp Lys Phe Asn Glu Gln
225                 230                 235                 240

Glu Ile Asn Leu Ser Met Ala Gly Asp Leu Ser Ala Gly Phe Phe Met
                245                 250                 255

Glu Glu Leu Asn Thr Tyr Arg Gln Lys Gln Gly Val Val Leu Lys Tyr
                260                 265                 270

Gln Glu Leu Pro Asn Ser Gly Pro Pro His Asp Arg Arg Phe Thr Phe
            275                 280                 285

Gln Val Ile Ile Asp Gly Arg Glu Phe Pro Glu Gly Glu Gly Arg Ser
290                 295                 300

Lys Lys Glu Ala Lys Asn Ala Ala Ala Lys Leu Ala Val Glu Ile Leu
305                 310                 315                 320

Asn Lys Glu His His His His His His
                325

<210> SEQ ID NO 14
<211> LENGTH: 1328
<212> TYPE: PRT
<213> ORGANISM: Artificial Sequence
<220> FEATURE:
<223> OTHER INFORMATION: Cas9 coupled to LFn

<400> SEQUENCE: 14

Met Gly Lys Pro Ile Pro Asn Pro Leu Leu Gly Leu Asp Ser Thr Met
1               5                   10                  15

Glu Arg Asn Lys Thr Gln Glu Glu His Leu Lys Glu Ile Met Lys His
            20                  25                  30

Ile Val Lys Ile Glu Val Lys Gly Glu Glu Ala Val Lys Lys Glu Ala
        35                  40                  45

Ala Glu Lys Leu Leu Glu Lys Val Pro Ser Asp Val Leu Glu Met Tyr
50                  55                  60

Lys Ala Ile Gly Gly Lys Ile Tyr Ile Val Asp Gly Asp Ile Thr Lys
65                  70                  75                  80

His Ile Ser Leu Glu Ala Leu Ser Glu Asp Lys Lys Lys Ile Lys Asp
                85                  90                  95

Ile Tyr Gly Lys Asp Ala Leu Leu His Glu His Tyr Val Tyr Ala Lys
                100                 105                 110

Glu Gly Tyr Glu Pro Val Leu Val Ile Gln Ser Ser Glu Asp Tyr Val
            115                 120                 125

Glu Asn Thr Glu Lys Ala Leu Asn Val Tyr Tyr Glu Ile Gly Lys Ile
130                 135                 140

Leu Ser Arg Asp Ile Leu Ser Lys Ile Asn Gln Pro Tyr Gln Lys Phe
145                 150                 155                 160

Leu Asp Val Leu Asn Thr Ile Lys Asn Ala Ser Asp Ser Asp Gly Gln
                165                 170                 175

Asp Leu Leu Phe Thr Asn Gln Leu Lys Glu His Pro Thr Asp Phe Ser
                180                 185                 190

Val Glu Phe Leu Glu Gln Asn Ser Asn Glu Val Gln Glu Val Phe Ala
            195                 200                 205

Lys Ala Phe Ala Tyr Tyr Ile Glu Pro Gln His Arg Asp Val Leu Gln
210                 215                 220
```

```
Leu Tyr Ala Pro Glu Ala Phe Asn Tyr Met Asp Lys Phe Asn Glu Gln
225                 230                 235                 240

Glu Ile Asn Leu Ser Leu Glu Val Leu Phe Gln Gly Pro Met Lys Arg
            245                 250                 255

Asn Tyr Ile Leu Gly Leu Asp Ile Gly Ile Thr Ser Val Gly Tyr Gly
                260                 265                 270

Ile Ile Asp Tyr Glu Thr Arg Asp Val Ile Asp Ala Gly Val Arg Leu
        275                 280                 285

Phe Lys Glu Ala Asn Val Glu Asn Asn Glu Gly Arg Arg Ser Lys Arg
    290                 295                 300

Gly Ala Arg Arg Leu Lys Arg Arg Arg His Arg Ile Gln Arg Val
305                 310                 315                 320

Lys Lys Leu Leu Phe Asp Tyr Asn Leu Leu Thr Asp His Ser Glu Leu
                325                 330                 335

Ser Gly Ile Asn Pro Tyr Glu Ala Arg Val Lys Gly Leu Ser Gln Lys
                340                 345                 350

Leu Ser Glu Glu Glu Phe Ser Ala Ala Leu Leu His Leu Ala Lys Arg
            355                 360                 365

Arg Gly Val His Asn Val Asn Glu Val Glu Glu Asp Thr Gly Asn Glu
    370                 375                 380

Leu Ser Thr Lys Glu Gln Ile Ser Arg Asn Ser Lys Ala Leu Glu Glu
385                 390                 395                 400

Lys Tyr Val Ala Glu Leu Gln Leu Glu Arg Leu Lys Lys Asp Gly Glu
                405                 410                 415

Val Arg Gly Ser Ile Asn Arg Phe Lys Thr Ser Asp Tyr Val Lys Glu
        420                 425                 430

Ala Lys Gln Leu Leu Lys Val Gln Lys Ala Tyr His Gln Leu Asp Gln
    435                 440                 445

Ser Phe Ile Asp Thr Tyr Ile Asp Leu Leu Glu Thr Arg Arg Thr Tyr
    450                 455                 460

Tyr Glu Gly Pro Gly Glu Gly Ser Pro Phe Gly Trp Lys Asp Ile Lys
465                 470                 475                 480

Glu Trp Tyr Glu Met Leu Met Gly His Cys Thr Tyr Phe Pro Glu Glu
                485                 490                 495

Leu Arg Ser Val Lys Tyr Ala Tyr Asn Ala Asp Leu Tyr Asn Ala Leu
                500                 505                 510

Asn Asp Leu Asn Asn Leu Val Ile Thr Arg Asp Glu Asn Glu Lys Leu
        515                 520                 525

Glu Tyr Tyr Glu Lys Phe Gln Ile Ile Glu Asn Val Phe Lys Gln Lys
    530                 535                 540

Lys Lys Pro Thr Leu Lys Gln Ile Ala Lys Glu Ile Leu Val Asn Glu
545                 550                 555                 560

Glu Asp Ile Lys Gly Tyr Arg Val Thr Ser Thr Gly Lys Pro Glu Phe
                565                 570                 575

Thr Asn Leu Lys Val Tyr His Asp Ile Lys Asp Ile Thr Ala Arg Lys
            580                 585                 590

Glu Ile Ile Glu Asn Ala Glu Leu Leu Asp Gln Ile Ala Lys Ile Leu
        595                 600                 605

Thr Ile Tyr Gln Ser Ser Glu Asp Ile Gln Glu Glu Leu Thr Asn Leu
    610                 615                 620

Asn Ser Glu Leu Thr Gln Glu Glu Ile Glu Gln Ile Ser Asn Leu Lys
625                 630                 635                 640

Gly Tyr Thr Gly Thr His Asn Leu Ser Leu Lys Ala Ile Asn Leu Ile
```

-continued

```
                645                 650                 655
Leu Asp Glu Leu Trp His Thr Asn Asp Asn Gln Ile Ala Ile Phe Asn
                660                 665                 670

Arg Leu Lys Leu Val Pro Lys Val Asp Leu Ser Gln Gln Lys Glu
675                 680                 685

Ile Pro Thr Thr Leu Val Asp Asp Phe Ile Leu Ser Pro Val Val Lys
                690                 695                 700

Arg Ser Phe Ile Gln Ser Ile Lys Val Ile Asn Ala Ile Ile Lys Lys
705                 710                 715                 720

Tyr Gly Leu Pro Asn Asp Ile Ile Glu Leu Ala Arg Glu Lys Asn
                725                 730                 735

Ser Lys Asp Ala Gln Lys Met Ile Asn Glu Met Gln Lys Arg Asn Arg
                740                 745                 750

Gln Thr Asn Glu Arg Ile Glu Glu Ile Ile Arg Thr Thr Gly Lys Glu
                755                 760                 765

Asn Ala Lys Tyr Leu Ile Glu Lys Ile Lys Leu His Asp Met Gln Glu
770                 775                 780

Gly Lys Cys Leu Tyr Ser Leu Glu Ala Ile Pro Leu Glu Asp Leu Leu
785                 790                 795                 800

Asn Asn Pro Phe Asn Tyr Glu Val Asp His Ile Ile Pro Arg Ser Val
                805                 810                 815

Ser Phe Asp Asn Ser Phe Asn Asn Lys Val Leu Val Lys Gln Glu Glu
                820                 825                 830

Asn Ser Lys Lys Gly Asn Arg Thr Pro Phe Gln Tyr Leu Ser Ser Ser
                835                 840                 845

Asp Ser Lys Ile Ser Tyr Glu Thr Phe Lys Lys His Ile Leu Asn Leu
850                 855                 860

Ala Lys Gly Lys Gly Arg Ile Ser Lys Thr Lys Lys Glu Tyr Leu Leu
865                 870                 875                 880

Glu Glu Arg Asp Ile Asn Arg Phe Ser Val Gln Lys Asp Phe Ile Asn
                885                 890                 895

Arg Asn Leu Val Asp Thr Arg Tyr Ala Thr Arg Gly Leu Met Asn Leu
                900                 905                 910

Leu Arg Ser Tyr Phe Arg Val Asn Asn Leu Asp Val Lys Val Lys Ser
                915                 920                 925

Ile Asn Gly Gly Phe Thr Ser Phe Leu Arg Arg Lys Trp Lys Phe Lys
                930                 935                 940

Lys Glu Arg Asn Lys Gly Tyr Lys His His Ala Glu Asp Ala Leu Ile
945                 950                 955                 960

Ile Ala Asn Ala Asp Phe Ile Phe Lys Glu Trp Lys Lys Leu Asp Lys
                965                 970                 975

Ala Lys Lys Val Met Glu Asn Gln Met Phe Glu Glu Lys Gln Ala Glu
                980                 985                 990

Ser Met Pro Glu Ile Glu Thr Glu Gln Glu Tyr Lys Glu Ile Phe Ile
                995                 1000                1005

Thr Pro His Gln Ile Lys His Ile Lys Asp Phe Lys Asp Tyr Lys
                1010                1015                1020

Tyr Ser His Arg Val Asp Lys Lys Pro Asn Arg Glu Leu Ile Asn
                1025                1030                1035

Asp Thr Leu Tyr Ser Thr Arg Lys Asp Asp Lys Gly Asn Thr Leu
                1040                1045                1050

Ile Val Asn Asn Leu Asn Gly Leu Tyr Asp Lys Asp Asn Asp Lys
                1055                1060                1065
```

Leu Lys Lys Leu Ile Asn Lys Ser Pro Glu Lys Leu Leu Met Tyr
    1070            1075                1080

His His Asp Pro Gln Thr Tyr Gln Lys Leu Lys Leu Ile Met Glu
    1085            1090                1095

Gln Tyr Gly Asp Glu Lys Asn Pro Leu Tyr Lys Tyr Tyr Glu Glu
    1100            1105                1110

Thr Gly Asn Tyr Leu Thr Lys Tyr Ser Lys Lys Asp Asn Gly Pro
    1115            1120                1125

Val Ile Lys Lys Ile Lys Tyr Tyr Gly Asn Lys Leu Asn Ala His
    1130            1135                1140

Leu Asp Ile Thr Asp Asp Tyr Pro Asn Ser Arg Asn Lys Val Val
    1145            1150                1155

Lys Leu Ser Leu Lys Pro Tyr Arg Phe Asp Val Tyr Leu Asp Asn
    1160            1165                1170

Gly Val Tyr Lys Phe Val Thr Val Lys Asn Leu Asp Val Ile Lys
    1175            1180                1185

Lys Glu Asn Tyr Tyr Glu Val Asn Ser Lys Cys Tyr Glu Glu Ala
    1190            1195                1200

Lys Lys Leu Lys Lys Ile Ser Asn Gln Ala Glu Phe Ile Ala Ser
    1205            1210                1215

Phe Tyr Asn Asn Asp Leu Ile Lys Ile Asn Gly Glu Leu Tyr Arg
    1220            1225                1230

Val Ile Gly Val Asn Asn Asp Leu Leu Asn Arg Ile Glu Val Asn
    1235            1240                1245

Met Ile Asp Ile Thr Tyr Arg Glu Tyr Leu Glu Asn Met Asn Asp
    1250            1255                1260

Lys Arg Pro Pro Arg Ile Ile Lys Thr Ile Ala Ser Lys Thr Gln
    1265            1270                1275

Ser Ile Lys Lys Tyr Ser Thr Asp Ile Leu Gly Asn Leu Tyr Glu
    1280            1285                1290

Val Lys Ser Lys Lys His Pro Gln Ile Ile Lys Lys Gly Tyr Pro
    1295            1300                1305

Tyr Asp Val Pro Asp Tyr Ala Glu Asn Leu Tyr Phe Gln Gly His
    1310            1315                1320

His His His His His
    1325

<210> SEQ ID NO 15
<211> LENGTH: 484
<212> TYPE: PRT
<213> ORGANISM: Artificial Sequence
<220> FEATURE:
<223> OTHER INFORMATION: Diphtheria toxin A (DTA) coupled to LFn

<400> SEQUENCE: 15

Met Gly Ser Ser His His His His His Ser Ser Gly Leu Val Pro
1               5                   10                  15

Arg Gly Ser His Met Ala Gly Gly His Gly Asp Val Gly Met His Val
                20                  25                  30

Lys Glu Lys Glu Lys Asn Lys Asp Glu Asn Lys Arg Lys Asp Glu Glu
        35                  40                  45

Arg Asn Lys Thr Gln Glu Glu His Leu Lys Glu Ile Met Lys His Ile
    50                  55                  60

Val Lys Ile Glu Val Lys Gly Glu Glu Ala Val Lys Lys Glu Ala Ala
65                  70                  75                  80

```
Glu Lys Leu Leu Glu Lys Val Pro Ser Asp Val Leu Glu Met Tyr Lys
            85                  90                  95

Ala Ile Gly Gly Lys Ile Tyr Ile Val Asp Gly Asp Ile Thr Lys His
            100                 105                 110

Ile Ser Leu Glu Ala Leu Ser Glu Asp Lys Lys Ile Lys Asp Ile
            115                 120                 125

Tyr Gly Lys Asp Ala Leu Leu His Glu His Tyr Val Tyr Ala Lys Glu
            130                 135                 140

Gly Tyr Glu Pro Val Leu Val Ile Gln Ser Ser Glu Asp Tyr Val Glu
145                 150                 155                 160

Asn Thr Glu Lys Ala Leu Asn Val Tyr Tyr Glu Ile Gly Lys Ile Leu
            165                 170                 175

Ser Arg Asp Ile Leu Ser Lys Ile Asn Gln Pro Tyr Gln Lys Phe Leu
            180                 185                 190

Asp Val Leu Asn Thr Ile Lys Asn Ala Ser Asp Ser Asp Gly Gln Asp
            195                 200                 205

Leu Leu Phe Thr Asn Gln Leu Lys Glu His Pro Thr Asp Phe Ser Val
210                 215                 220

Glu Phe Leu Glu Gln Asn Ser Asn Glu Val Gln Glu Val Phe Ala Lys
225                 230                 235                 240

Ala Phe Ala Tyr Tyr Ile Glu Pro Gln His Arg Asp Val Leu Gln Leu
            245                 250                 255

Tyr Ala Pro Glu Ala Phe Asn Tyr Met Asp Lys Phe Asn Glu Gln Glu
            260                 265                 270

Ile Asn Leu Ser Ala Met Gly Ser Ser His His His His His His Ser
            275                 280                 285

Ser Gly Leu Val Pro Arg Gly Ala Asp Asp Val Val Asp Ser Ser Lys
            290                 295                 300

Ser Phe Val Met Glu Asn Phe Ser Ser Tyr His Gly Thr Lys Pro Gly
305                 310                 315                 320

Tyr Val Asp Ser Ile Gln Lys Gly Ile Gln Lys Pro Lys Ser Gly Thr
            325                 330                 335

Gln Gly Asn Tyr Asp Asp Asp Trp Lys Gly Phe Tyr Ser Thr Asp Asn
            340                 345                 350

Lys Tyr Asp Ala Ala Gly Tyr Ser Val Asp Asn Glu Asn Pro Leu Ser
            355                 360                 365

Gly Lys Ala Gly Gly Val Val Lys Val Thr Tyr Pro Gly Leu Thr Lys
            370                 375                 380

Val Leu Ala Leu Lys Val Asp Asn Ala Glu Thr Ile Lys Lys Glu Leu
385                 390                 395                 400

Gly Leu Ser Leu Thr Glu Pro Leu Met Glu Gln Val Gly Thr Glu Glu
            405                 410                 415

Phe Ile Lys Arg Phe Gly Asp Gly Ala Ser Arg Val Val Leu Ser Leu
            420                 425                 430

Pro Phe Ala Glu Gly Ser Ser Ser Val Glu Tyr Ile Asn Asn Trp Glu
            435                 440                 445

Gln Ala Lys Ala Leu Ser Val Glu Leu Glu Ile Asn Phe Glu Thr Arg
450                 455                 460

Gly Lys Arg Gly Gln Asp Ala Met Tyr Glu Tyr Met Ala Gln Ala Cys
465                 470                 475                 480

Ala Gly Asn Arg
```

```
<210> SEQ ID NO 16
<211> LENGTH: 1455
<212> TYPE: DNA
<213> ORGANISM: Artificial Sequence
<220> FEATURE:
<223> OTHER INFORMATION: payload molecule

<400> SEQUENCE: 16
atgggcagca gccatcatca tcatcatcac agcagcggcc tggtgccgcg cggcagccat      60
atggcgggcg gtcatggtga tgtaggtatg cacgtaaaag agaaagagaa aaataaagat     120
gagaataaga gaaaagatga agaacgaaat aaaacacagg aagagcattt aaaggaaatc     180
atgaaacaca ttgtaaaaat agaagtaaaa ggggaggaag ctgttaaaaa agaggcagca     240
gaaaagctac ttgagaaagt accatctgat gttttagaga tgtataaagc aattggagga     300
aagatatata ttgtggatgg tgatattaca aaacatatat ctttagaagc attatctgaa     360
gataagaaaa aaataaaaga catttatggg aaagatgctt tattacatga acattatgta     420
tatgcaaaag aaggatatga acccgtactt gtaatccaat cttcggaaga ttatgtagaa     480
aatactgaaa aggcactgaa cgtttattat gaaataggta agatattatc aagggatatt     540
ttaagtaaaa ttaatcaacc atatcagaaa tttttagatg tattaaatac cattaaaaat     600
gcatctgatt cagatggaca agatctttta tttactaatc agcttaagga acatcccaca     660
gacttttctg tagaattctt ggaacaaaat agcaatgagg tacaagaagt atttgcgaaa     720
gcttttgcat attatatcga gccacagcat cgtgatgttt tacagcttta tgcaccggaa     780
gcttttaatt acatggataa atttaacgaa caagaaataa atctatccgc catgggcagc     840
tctcaccacc accaccacca ctcttccggc ctggttccac gtggtgctga cgacgttgtt     900
gactcttcta atctttcgt tatggaaaac ttctcttctt accacggtac caaaccgggt     960
tacgtcgact ctatccagaa aggtatccag aagccgaaat ctggtaccca gggtaactac    1020
gacgacgact ggaaaggttt ctactctacc gacaacaaat acgacgccgc gggttactct    1080
gttgacaacg aaaacccgct gtctggtaaa gctggtggtg ttgttaaagt tacctacccg    1140
ggtctgacca agttctggc tctgaaagtt gacaacgctg aaaccatcaa aaaagaactg    1200
ggtctctctc tgaccgaacc gctgatggaa caggttggta ccgaagaatt catcaaacgt    1260
ttcggtgacg gtgcttctcg tgttgttctg tctctgccgt tcgctgaggg ctcttcttct    1320
gttgaataca tcaacaactg gaacaggct aaagctctgt ctgttgaact ggaaatcaac    1380
ttcgaacccc gtggtaaacg tggccaggac gctatgtacg aatacatggc tcaggcttgt    1440
gcaggtaacc gttaa                                                     1455

<210> SEQ ID NO 17
<211> LENGTH: 48
<212> TYPE: DNA
<213> ORGANISM: Artificial Sequence
<220> FEATURE:
<223> OTHER INFORMATION: anti-Tandem dimeric tomato ASO sequence
<220> FEATURE:
<221> NAME/KEY: modified_base
<222> LOCATION: (1)..(1)
<223> OTHER INFORMATION: Thymine with 3' Phosphorothioate modification
<220> FEATURE:
<221> NAME/KEY: modified_base
<222> LOCATION: (2)..(2)
<223> OTHER INFORMATION: Thymine with 3' Phosphorothioate modification
<220> FEATURE:
<221> NAME/KEY: modified_base
<222> LOCATION: (3)..(3)
<223> OTHER INFORMATION: Guanine with 3' Phosphorothioate modification
<220> FEATURE:
```

```
<221> NAME/KEY: modified_base
<222> LOCATION: (4)..(4)
<223> OTHER INFORMATION: Cytosine with 3' Phosphorothioate modification
<220> FEATURE:
<221> NAME/KEY: modified_base
<222> LOCATION: (5)..(5)
<223> OTHER INFORMATION: Thymine with 3' Phosphorothioate modification
<220> FEATURE:
<221> NAME/KEY: modified_base
<222> LOCATION: (6)..(6)
<223> OTHER INFORMATION: Guanine with 3' Phosphorothioate modification
<220> FEATURE:
<221> NAME/KEY: modified_base
<222> LOCATION: (7)..(7)
<223> OTHER INFORMATION: Thymine with 3' Phosphorothioate modification
<220> FEATURE:
<221> NAME/KEY: modified_base
<222> LOCATION: (8)..(8)
<223> OTHER INFORMATION: Cytosine with 3' Phosphorothioate modification
<220> FEATURE:
<221> NAME/KEY: modified_base
<222> LOCATION: (9)..(9)
<223> OTHER INFORMATION: Cytosine with 3' Phosphorothioate modification
<220> FEATURE:
<221> NAME/KEY: modified_base
<222> LOCATION: (10)..(10)
<223> OTHER INFORMATION: Adenine with 3' Phosphorothioate modification
<220> FEATURE:
<221> NAME/KEY: modified_base
<222> LOCATION: (11)..(11)
<223> OTHER INFORMATION: Cytosine with 3' Phosphorothioate modification
<220> FEATURE:
<221> NAME/KEY: modified_base
<222> LOCATION: (12)..(12)
<223> OTHER INFORMATION: Guanine with 3' Phosphorothioate modification
<220> FEATURE:
<221> NAME/KEY: modified_base
<222> LOCATION: (13)..(13)
<223> OTHER INFORMATION: Thymine with 3' Phosphorothioate modification
<220> FEATURE:
<221> NAME/KEY: modified_base
<222> LOCATION: (14)..(14)
<223> OTHER INFORMATION: Adenine with 3' Phosphorothioate modification
<220> FEATURE:
<221> NAME/KEY: modified_base
<222> LOCATION: (15)..(15)
<223> OTHER INFORMATION: Guanine with 3' Phosphorothioate modification
<220> FEATURE:
<221> NAME/KEY: modified_base
<222> LOCATION: (16)..(16)
<223> OTHER INFORMATION: Thymine with 3' Phosphorothioate modification
<220> FEATURE:
<221> NAME/KEY: modified_base
<222> LOCATION: (17)..(17)
<223> OTHER INFORMATION: Adenine with 3' Phosphorothioate modification
<220> FEATURE:
<221> NAME/KEY: modified_base
<222> LOCATION: (18)..(18)
<223> OTHER INFORMATION: Guanine with 3' Phosphorothioate modification
<220> FEATURE:
<221> NAME/KEY: modified_base
<222> LOCATION: (19)..(19)
<223> OTHER INFORMATION: Thymine with 3' Phosphorothioate modification
<220> FEATURE:
<221> NAME/KEY: modified_base
<222> LOCATION: (20)..(20)
<223> OTHER INFORMATION: Adenine with 3' Phosphorothioate modification
<220> FEATURE:
<221> NAME/KEY: modified_base
<222> LOCATION: (21)..(21)
<223> OTHER INFORMATION: Guanine with 3' Phosphorothioate modification

<400> SEQUENCE: 17
nnnnnnnnnn nnnnnnnnnn ngcatgccgg catcagagca gccggcat            48

<210> SEQ ID NO 18
<211> LENGTH: 48
```

```
<212> TYPE: DNA
<213> ORGANISM: Artificial Sequence
<220> FEATURE:
<223> OTHER INFORMATION: anti-Tandem dimeric tomato ASO sequence
<220> FEATURE:
<221> NAME/KEY: modified_base
<222> LOCATION: (1)..(1)
<223> OTHER INFORMATION: Thymine with 3' Phosphorothioate modification
<220> FEATURE:
<221> NAME/KEY: modified_base
<222> LOCATION: (2)..(2)
<223> OTHER INFORMATION: Thymine with 3' Phosphorothioate modification
<220> FEATURE:
<221> NAME/KEY: modified_base
<222> LOCATION: (3)..(3)
<223> OTHER INFORMATION: Guanine with 3' Phosphorothioate modification
<220> FEATURE:
<221> NAME/KEY: modified_base
<222> LOCATION: (4)..(4)
<223> OTHER INFORMATION: Cytosine with 3' Phosphorothioate modification
<220> FEATURE:
<221> NAME/KEY: modified_base
<222> LOCATION: (5)..(5)
<223> OTHER INFORMATION: Thymine with 3' Phosphorothioate modification
<220> FEATURE:
<221> NAME/KEY: modified_base
<222> LOCATION: (6)..(6)
<223> OTHER INFORMATION: Guanine with 3' Phosphorothioate modification
<220> FEATURE:
<221> NAME/KEY: modified_base
<222> LOCATION: (7)..(7)
<223> OTHER INFORMATION: Thymine with 3' Phosphorothioate modification
<220> FEATURE:
<221> NAME/KEY: modified_base
<222> LOCATION: (8)..(8)
<223> OTHER INFORMATION: Cytosine with 3' Phosphorothioate modification
<220> FEATURE:
<221> NAME/KEY: modified_base
<222> LOCATION: (9)..(9)
<223> OTHER INFORMATION: Cytosine with 3' Phosphorothioate modification
<220> FEATURE:
<221> NAME/KEY: modified_base
<222> LOCATION: (10)..(10)
<223> OTHER INFORMATION: Adenine with 3' Phosphorothioate modification
<220> FEATURE:
<221> NAME/KEY: modified_base
<222> LOCATION: (11)..(11)
<223> OTHER INFORMATION: Cytosine with 3' Phosphorothioate modification
<220> FEATURE:
<221> NAME/KEY: modified_base
<222> LOCATION: (12)..(12)
<223> OTHER INFORMATION: Guanine with 3' Phosphorothioate modification
<220> FEATURE:
<221> NAME/KEY: modified_base
<222> LOCATION: (13)..(13)
<223> OTHER INFORMATION: Thymine with 3' Phosphorothioate modification
<220> FEATURE:
<221> NAME/KEY: modified_base
<222> LOCATION: (14)..(14)
<223> OTHER INFORMATION: Adenine with 3' Phosphorothioate modification
<220> FEATURE:
<221> NAME/KEY: modified_base
<222> LOCATION: (15)..(15)
<223> OTHER INFORMATION: Guanine with 3' Phosphorothioate modification
<220> FEATURE:
<221> NAME/KEY: modified_base
<222> LOCATION: (16)..(16)
<223> OTHER INFORMATION: Thymine with 3' Phosphorothioate modification
<220> FEATURE:
<221> NAME/KEY: modified_base
<222> LOCATION: (17)..(17)
<223> OTHER INFORMATION: Adenine with 3' Phosphorothioate modification
<220> FEATURE:
<221> NAME/KEY: modified_base
<222> LOCATION: (18)..(18)
<223> OTHER INFORMATION: Guanine with 3' Phosphorothioate modification
<220> FEATURE:
<221> NAME/KEY: modified_base
<222> LOCATION: (19)..(19)
```

```
<223> OTHER INFORMATION: Thymine with 3' Phosphorothioate modification
<220> FEATURE:
<221> NAME/KEY: modified_base
<222> LOCATION: (20)..(20)
<223> OTHER INFORMATION: Adenine with 3' Phosphorothioate modification
<220> FEATURE:
<221> NAME/KEY: modified_base
<222> LOCATION: (21)..(21)
<223> OTHER INFORMATION: Guanine with 3' Phosphorothioate modification

<400> SEQUENCE: 18
nnnnnnnnnn nnnnnnnnnn ngcatgccgg ctgctctgat gccggcat                    48
```